United States Patent
Saris

(10) Patent No.: US 6,627,199 B1
(45) Date of Patent: Sep. 30, 2003

(54) ISOLATION, IDENTIFICATION AND CHARACTERIZATION OF TMST2, A NOVEL MEMBER OF THE TNF-RECEPTOR SUPERGENE FAMILY

(75) Inventor: Chris Saris, Newbury Park, CA (US)

(73) Assignee: Amgen Inc, Thousand Oaks, CA (US)

( * ) Notice: Subject to any disclaimer, the term of this patent is extended or adjusted under 35 U.S.C. 154(b) by 19 days.

(21) Appl. No.: 09/612,033

(22) Filed: Jul. 7, 2000

Related U.S. Application Data

(60) Provisional application No. 60/143,063, filed on Jul. 9, 1999.

(51) Int. Cl.$^7$ .................... A61K 39/395; C07H 21/04; C07K 14/705
(52) U.S. Cl. ................. 424/192.1; 536/23.5; 530/350; 435/252.3; 435/254.1; 435/69.1; 424/178.1; 424/1.73
(58) Field of Search ................... 536/23.5; 530/350; 435/320.1, 252.3, 325, 69.1; 424/192.1

(56) References Cited

U.S. PATENT DOCUMENTS

| | | | |
|---|---|---|---|
| 5,489,743 A | 2/1996 | Robinson et al. | 800/2 |
| 5,843,789 A | 12/1998 | Nomura et al. | 436/164 |
| 5,863,769 A | 1/1999 | Young | 435/69.52 |
| 5,942,385 A * | 8/1999 | Hirth | 435/366 |
| 6,346,382 B1 * | 2/2002 | Summar et al. | 435/6 |

FOREIGN PATENT DOCUMENTS

| | | |
|---|---|---|
| DE | 19809978 | 9/1999 |
| EP | 0861850 | 9/1998 |
| WO | WO 96/14328 | 5/1996 |
| WO | WO 96/37609 | 11/1996 |
| WO | WO 98/30694 | 7/1998 |
| WO | WO9843998 A1 * | 10/1998 |
| WO | WO 99/04001 | 1/1999 |
| WO | WO 99/06426 | 2/1999 |
| WO | WO 99/07738 | 2/1999 |
| WO | WO 99/14330 | 3/1999 |
| WO | WO 99/20758 | 4/1999 |
| WO | WO 99/23105 | 5/1999 |
| WO | WO 99/26977 | 6/1999 |
| WO | WO 99/35268 | 7/1999 |
| WO | WO 99/50413 | 10/1999 |
| WO | WO 99/51744 | 10/1999 |
| WO | WO 00/08139 | 2/2000 |
| WO | WO 00/18800 | 4/2000 |

OTHER PUBLICATIONS

Skolnick et al., From genes to protein structure and function: novel applications of computational approaches in the genomic era. Trends in Biotechnology, pp. 34–39, 2000.*
EST Database Accession No. A1747041, Jun. 22, 1999.*
Locksley et al., The TNF and TNF Receptor Superfamilies: Integrating Mammalian Biology, *Cell*, 104:487–501(2001).
Moult, The Current State of the Art In Protein Structure Prediction, *Curr. Op. in Biotech.*, 7(4):422–427(1996).
Nophar et al., Soluble Forms of Tumor Necrosis Factor Receptors (TNF–Rs). The cDNA for the Type I TNF–R, Cloned Using Amino Acid Sequence Data of its Soluble Form, Encodes Both the Cell Surface and a Soluble Form of the Receptor, *EMBO J.*, 9(10):3269–3278(1990).
Orlinick and Chao, TNF–Related Ligands and Their Receptors, *Cell Signal*, 10(8):543–551(1998).
Ouchterlony and Nilsson, Immunodiffusion and Immunoelectrophoresis in: *Handbook of Experimental Immunology* ed. D. Weir, Blackwell, 1973.
Porteu et al., Human Neutrophil Elastase Releases a Ligand–binding Fragment from the 75–kDa Tumor Necrosis Factor (TNF) Receptor, *J. Biol. Chem.*, 266:18846–18853(1991).
Smith et al., Four New Members Expand the Interleukin–1 Superfamily, *J. Bio. Chem.*, 275(2):1169–1175(2000).
Vaitukaitis et al., A Method For Producing Specific Antisera With Small Doses of Immunogen, *J. Clin. Endocrinol.*, 33:988–991(1971).
Wallach et al., Soluble and Cell Surface Receptors for Tumor Necrosis Factor, *Agents Actions Suppl.*, 35:51–57(1991).
Baker and Reddy, Transducers of Life and Death: TNF Receptor Superfamily and Associated Proteins, *Oncogene*, 12(1):1–9(1996).
Beyaert and Fiers, *Tumor Necrosis Factor and Lymphokines* in: Cytokines eds. Anthony Mire–Sluis and Robin Thorpe, Academic Press San Diego CA, 1998.
Browning et al., Lymphotoxin β, a Novel Member of the TNF Family That Forms a Heteromeric Complex with Lymphotoxin on the Cell Surface, *Cell*, 72:847–856, (1993).
Fernandez–Botran, Soluble Cytokine Receptors: Their Role In Immunoregulation, *FASB J.*, 5:2567–2574(1991).
Fisher, Production of Antibody in Radioimmunoassay in; *Manual of Clinical Immunology*, 2d Ed. (Rose and Friedman, eds.) Amer. Soc. For Microbiol., Washington, D.C., 1980.
Genebank accession No. aa155701, "zo70e05.r1 Stratagene pancreas (#937208( ) Homo sapiens cDNA clone IMAGE:592256 5', mRNA sequence", Hillier el al., 1997.
Genbank accession No.: AAC50332, TNF–related Apoptosis Inducing Ligand Trail, Wiley et al., Jan. 6, 1996.
Genbank accession No.: NP033451, TNF–Related Apoptosis Inducing Ligand [*Mus musculus*], Wiley et al., 2000.
Genbank accession No.: CAA26669, TNF–alpha [*Homo sapiens*], Nedwin et al., Feb. 17, 1997.

(List continued on next page.)

*Primary Examiner*—Lorraine Spector
*Assistant Examiner*—Eileen B. O'Hara
(74) *Attorney, Agent, or Firm*—Marshall, Gerstein & Borun

(57) ABSTRACT

Novel TNF receptor polypeptides are disclosed, along with polynucleotides encoding the polypeptides and uses thereof.

20 Claims, No Drawings

OTHER PUBLICATIONS

Genbank accension No.: CAA68530, TNF–alpha [*Mus musculus*], Jongeneel, May 11, 1993.

Aderka et al., The Potential Biological and Chemical Significance of the Soluble Tumor Necrosis Factor Receptors, *Cytokine & Growth Factor Reviews*, 7(3):231–240(1996).

Aggarwal et al., Characterization of Receptors for Tumor Necrosis Factor and their Regulation By γ–Interferon, *Nature*, 318:665–667(1985).

Ausubel et al., eds., *Current Protocols in Molecular Biology*, 1, Section 9.1.1–9.1.3, John Wiley & Sons, New York 1996.

\* cited by examiner

ISOLATION, IDENTIFICATION AND CHARACTERIZATION OF TMST2, A NOVEL MEMBER OF THE TNF-RECEPTOR SUPERGENE FAMILY

RELATED APPLICATIONS

This patent application claims priority from U.S. provisional patent application No. 60/143,063 filed Jul. 9, 1999.

FIELD OF THE INVENTION

The invention is in the field of recombinant genetics. In particular, the present invention relates to a novel transmembrane decoy-receptor, tmst2, and its secreted splice variant, belonging to the TNF-receptor super genie family and nucleic acid molecules encoding same. The invention also relates to vectors, host cells, antibodies and recombinant methods for producing both the membrane associated and the soluble forms of the receptor polypeptides. The invention also relates to the use of the recombinant tmst2 receptor polypeptide to identify putative binding proteins. In addition, methods and reagents are provided for the diagnosis of diseases associated with or resulting from abnormal tmst2 and/or abnormal expression of its putative ligand, and methods and pharmaceutical composition(s) for the treatment, amelioration and/or treatment of diseases associated with abnormal tmst2 or abnormal expression of tmst2 and/or its ligand. The invention also discloses pharmaceutical compositions for use in the treatment of these diseases.

BACKGROUND OF THE INVENTION

Technical advances in the identification, cloning, expression and manipulation of nucleic acid molecules have greatly accelerated the discovery of novel therapeutics based upon deciphering the human genome. Rapid nucleic acid sequencing techniques can now generate sequence information at unprecedented rates, and coupled with computational analyses, allow the assembly of overlapping sequences into the entire genome and the identification of polypeptide-encoding regions. Comparison of a predicted amino acid sequence against a database compilation of known amino acid sequences can allow one to determine the extent of homology to previously identified sequences and/or structure landmarks. Cloning and expression of a polypeptide-encoding region of a nucleic acid molecule provides a polypeptide product for structural and functional analysis. Manipulation of a nucleic acid molecule(s) and encoded polypeptide(s) to give variants and derivatives thereof may confer advantageous properties on a product for use as a therapeutic.

However, in spite of the significant technical advances in genome research over the past decade, the potential for development of novel therapeutics based on the human genome is still largely unrealized. While a number of genes encoding potentially beneficial protein therapeutics, or those encoding polypeptides which may act as "targets" for therapeutic molecules, have been identified using recombinant DNA technology, the structure and function of a vast number of genes in the genome of mammals are yet unknown.

Using the above mentioned recombinant DNA technology, we have recently identified a new member of the tumor necrosis factor (TNF)-receptor supergene family, hereinafter referred to as "tmst2", and secreted splice variant of tmst2-receptor polypeptide, hereinafter referred to as tmst2 which may elicit its effects by binding a member of the TNF-family of ligands.

Identification and Characterization of TNF-Family of Ligands and Receptors

Tumor necrosis factor (TNF) was first identified in the serum of mice and rabbits which had been infected with bacillus of Calmette and Guerin(BCG) and which had been injected with endotoxin. TNF activity in the serum of these animals was recognized on the basis of its cytotoxic and anti-tumor activities. This TNF activity, referred to as TNF-α, is produced particularly by activated monocytes and macrophages, and has been implicated in normal growth processes as well as in a variety of diseases.

Following the discovery of TNF-α, independent research led to the identification of another cytokine associated with inflammatory responses lymphotoxin-α (LT-α) which was shown to be produced exclusively by lymphocytes. LT-α was subsequently shown to be 30% homologous with TNF-α, and was renamed TNF-β. It is now clear that TNF-α and TNF-β are members of a gene family that includes yet another member termed LT-β (Browning et al., *Cell* 72:847–856 (1993)). The three genes are tightly linked within the MHC complex and show similar organization. Moreover, the biologically active forms of TNF-α and TNF-β are homotrimers and share many of the same biological activities including competing for the same cell-surface receptors (Agarwal et al., *Nature* 318:665–667 (1985)). Two distinct but structurally homologous receptors have been identified, and each has been shown to bind both the ligands and mediate their effects.

However, it has been recognized that TNFs are only representative members of the rapidly expanding supergene family that includes TNF-α, TNF-β/lymphotoxin-α (LT-α), lynphotoxin-β (LT-β), FasL, CD40L, CD30L, CD27L, 4-IBBL, and TNF-related apoptosis-inducing ligand (TRAIL), RANKL, GITRL and TNF-2. The distinctive but overlapping cellular responses induced by members of the TNF family of ligands following their interaction(s) with their cognate cell-surface receptors result in clearly defined developmental and regulatory changes in cells of the lymphoid, hematopoietic, and other lineages. For example, TNF family of ligands are involved in growth regulation and differentiation of cells which are involved in inflammation, immune processes and hematopoiesis (Bayert, R. and Fiers, W., *Tumor Necrosis Factor and Lymphokines* in: Cytokines eds. Anthony Mire-Sluis and Robin Thorpe, Academic Press San Diego Calif. (1998)). TNF family of ligands activate the immune defenses against parasites, and acts directly and/or indirectly as a mediator in immune reactions and inflammatory processes. However, administration of TNF and/or other members of the TNF family can also be accompanied by harmful phenomena such as shock and tissue damage (Bayert, R. and Fiers, W., supra). The main physiological role of TNF family of ligands is likely the activation of first-line reaction of an organism to microbial, parasitic, viral, or to mechanical stress and cancer. For example, TNF-related apoptosis-inducing ligand (TRAIL) has been demonstrated to induce apoptosis of a number of different types of cancer cells as well as virally infected cells.

Furthermore, a number of observations have also led to the conclusion that TNF family of ligands are also involved in a variety of pathological conditions including cachexia, toxic shock syndrome, inflammatory diseases such as rheumatoid and osteoarthritis, in death resulting from graft-versus- host reaction (GVHR)(Bayert, R. and Fiers, W., supra), rapid necrosis of tumors, apoptosis, immunostimulation and resistance to parasites and viruses.

Like other cytokines, the TNF family of ligands binds to specific cell surface receptors. Based upon sequence similarities, the TNF receptors belong to a receptor gene super-family that includes the low-affinity nerve growth factor (NGF) receptor, the FAS antigen, the human B-lynphocyte activation molecule CD40, CD27, 4-1BB, PV-T2, CD30, TNF R-RP, TRAIL-R, PV-A53R, RANK, GITR and OX40 antigen found on activated T cells (Smith et al., *Cell*, 76: 959–62 (1994): Baker and Reddy, *Oncogene*, 12: 1–9 (1996)). Sequence similarities between any two family members may exist throughout the molecule, or be confined to the extracellular or intracellular domain. The intracellular domain of some of the receptors contains a so-called death domain (DD), which mediates ligand-induced programmed cell death (apoptosis). The pathways employed to induce death differ among death domains of individual TNF receptors. For example, the FAS antigen DD signals through FADD, RIP and caspase-8; the TNFR-1 signals through FADD, TRADD and caspase-8; and the death domain of the TRAIL-receptor DR4 induces apoptosis without interacting with any of the above adapter molecules. The sequence diversity among extracellular domains of the TNF receptor family is reflected in their binding specificities: some bind TNF, others do not.

In addition to the membrane associated receptor molecules described above, a number the receptors belonging to the TNF-receptor supergene family exist as soluble binding proteins. Many of the soluble forms of the transmembrane receptors were subsequently identified as containing only the extracellular ligand binding domain(s) of the receptors. For example, a soluble form of TNF receptor has been found in urine and serum (See U.S. Pat. No. : 5,843,789 and Nophar et al. *EMBO J.*, 9(10): 3269–78 (1990)), and have been shown to arise by proteolytic cleavage of cell surface TNF-receptors (Porteu et al., *J. Biol. Chem.*, 266: 18846–53 (1991)). These soluble forms of receptor molecules have been implicated in the modulation of TNF activity by not only interfering with TNF binding to its receptor, but also by stabilizing the structure and preserving its activity, thus prolonging some of its effects (Aderka et al, *Cytokine & Growth Factor Reviews*, 7(3):231–240 (1996)).

The activity of TNF family of ligands are tightly regulated at the levels of secretion and receptor expression. Additional regulatory mechanisms are provided by action of specific inhibitory proteins present on cell surface and in biological fluids. While some of these inhibitory proteins have been identified as soluble forms of receptor molecules, the identity of many of these cytokine regulatory proteins are as yet unknown. However, abnormalities in the production of these substances might contribute to the pathophysiology of a variety of diseases including immune and neoplastic diseases. Besides their role in regulating cytokine activity in vivo, these regulatory molecules hold significant potential for therapeutic use as very specific inhibitors/anti-cytokine agents, and as indicators in diagnosis and assessment of immune function and growth parameters in a variety of autoimmune and malignant diseases (Fernandez-Botran, *FASEB J.*, 5: 2567–74 (1991)).

Accordingly, the invention is directed to novel nucleic acid molecules encoding TNF-receptor(s) related molecule (s) that regulate the activity of TNF family of ligands, and to polypeptides encoded by the nucleic acids, as well as their use as diagnostic and/or therapeutic molecules of diseases.

SUMMARY OF THE INVENTION

The present invention relates to novel tmst2-receptor nucleic acid molecules and encoded polypeptides.

The invention provides for an isolated nucleic acid molecule comprising a nucleotide sequence selected from the group consisting of:

(a) the nucleotide sequence as set forth in SEQ ID NO: 7 or 9;

(b) a nucleotide sequence encoding the polypeptide as set forth in SEQ ID NO: 8 or 10;

(c) a nucleotide sequence which hybridizes under moderately or highly stringent conditions to the complement of (a) or (b), wherein the encoded polypeptide has an activity of the polypeptide as set forth in SEQ ID NO: 8 or 10; and (d) a nucleotide sequence complementary to any of (a)–(c).

The invention also provides for an isolated nucleic acid molecule comprising a nucleotide sequence selected from the group consisting of:

(a) a nucleotide sequence encoding a polypeptide that is at least about 70, 75, 80, 85, 90, 95, 96, 97, 98, or 99 percent identical to the polypeptide as set forth in SEQ ID NO: 8 or 10 as determined using a computer program selected from the group consisting of GAP, BLASTP, BLASTN, FASTA, BLASTA, BLASTX, BestFit, and the Smith-Waterman algorithm, wherein the polypeptide has an activity of the polypeptide as set forth in SEQ ID NO: 8 or 10;

(b) a nucleotide sequence encoding an allelic variant or splice variant of the nucleotide sequence as set forth in SEQ ID NO: 7 or 9, wherein the encoded polypeptide has an activity of the polypeptide as set forth in SEQ ID NO: 8 or 10;

(c) a nucleotide sequence of SEQ ID NO: 7 or 9, (a), or (b) encoding a polypeptide fragment of at least about 25 amino acid residues, wherein the polypeptide has an activity of the polypeptide as set forth in SEQ ID NO: 8 or 10;

(d) a nucleotide sequence encoding a polypeptide that has a substitution and/or deletion of 1 to 198 amino acid residues as set forth in any of SEQ ID NOS: 7–8 wherein the encoded polypeptide has an activity of the polypeptide as set forth in SEQ ID NO: 8 or 10;

(d) a nucleotide sequence encoding a polypeptide that has a substitution and/or deletion of 1 to 100 amino acid residues as set forth in any of SEQ ID NOS: 9–10 wherein the encoded polypeptide has an activity of the polypeptide as set forth in SEQ ID NO: 8 or 10;

(f) a nucleotide sequence of SEQ ID NO: 7 or 9, or (a)–(f) comprising a fragment of at least about 16 nucleotides;

(g) a nucleotide sequence which hybridizes under moderately or highly stringent conditions to the complement of any of (a)–(f), wherein the polypeptide has an activity of the polypeptide as set forth in SEQ ID NO: 8 or 10; and (h) a nucleotide sequence complementary to any of (a)–(f).

The invention further provides for an isolated nucleic acid molecule comprising a nucleotide sequence selected from the group consisting of.

(a) a nucleotide sequence encoding a polypeptide as set forth in SEQ ID NO: 8 or 10 with at least one conservative amino acid substitution, wherein the polypeptide has an activity of the polypeptide as set forth in SEQ ID NO: 8 or 10;

(b) a nucleotide sequence encoding a polypeptide as set forth in SEQ ID NO: 8 or 10 with at least one amino acid insertion, wherein the polypeptide has an activity of the polypeptide as set forth in SEQ ID NO: 8 or 10;

(c) a nucleotide sequence encoding a polypeptide as set forth in SEQ ID NO: 8 or 10 with at least one amino acid deletion, wherein the polypeptide has an activity of the polypeptide as set forth in SEQ ID NO: 8 or 10;

(d) a nucleotide sequence encoding a polypeptide as set forth in SEQ ID NO: 8 or 10 which has a C- and/or N-terminal truncation, wherein the polypeptide has an activity of the polypeptide as set forth in SEQ ID NO: 8 or 10;

(e) a nucleotide sequence encoding a polypeptide as set forth in SEQ ID NO: 8 or 10 with at least one modification selected from the group consisting of amino acid substitutions, amino acid insertions, amino acid deletions, C-terminal truncation, and N-terminal truncation, wherein the polypeptide has an activity of the polypeptide as set forth in SEQ ID NO: 8 or 10;

(f) a nucleotide sequence of (a)–(e) comprising a fragment of at least about 16 nucleotides;

(g) a nucleotide sequence which hybridizes under moderately or highly stringent conditions to the complement of any of (a)–(f), wherein the polypeptide has an activity of the polypeptide as set forth in SEQ ID NO: 8 or 10; and (h) a nucleotide sequence complementary to any of (a)–(e).

The invention also provides for an isolated polypeptide comprising the amino acid sequence selected from the group consisting of:

(a) the mature amino acid sequence as set forth in SEQ ID NO: 8 or 10 comprising a mature amino terminus at residue(s) 1, and optionally further comprising an amino-terminal methionine;

(b) an amino acid sequence for an ortholog of SEQ ID NO: 8 or 10, wherein the encoded polypeptide has an activity of the polypeptide as set forth in SEQ ID NO: 8 or 10;

(c) an amino acid sequence that is at least about 70, 80, 85, 90, 95, 96, 97, 98, 5 or 99 percent identical to the amino acid sequence of SEQ ID NO: 8 or 10 as determined using a computer program selected from the group consisting of GAP, BLASTP, BLASTN, FASTA, BLASTA, BLASTX, BestFit, and the Smith-Waterman algorithm;, wherein the polypeptide has an activity of the polypeptide as set forth in SEQ ID NO: 8 or 10;

(d) a fragment of the amino acid sequence set forth in SEQ ID NO: 8 or 10 comprising at least about 25 amino acid residues, wherein the polypeptide has an activity of the polypeptide as set forth in SEQ ID NO: 8 or 10;

(e) an amino acid sequence for an allelic variant or splice variant of either the amino acid sequence as set forth in SEQ ID NO: 8 or 10, or at least one of(a)–(c) wherein the polypeptide has an activity of the polypeptide as set forth in SEQ ID NO: 8 or 10.

The invention further provides for an isolated polypeptide comprising the amino acid sequence selected from the group consisting of:

(a) the amino acid sequence as set forth in SEQ ID NO: 8 or 10 with at least one conservative amino acid substitution, wherein the polypeptide has an activity of the polypeptide as set forth in SEQ ID NO: 8 or 10;

(b) the amino acid sequence as set forth in SEQ ID NO: 8 or 10 with at least one amino acid insertion, wherein the polypeptide has an activity of the polypeptide as set forth in SEQ ID NO: 8 or 10;

(c) the amino acid sequence as set forth in SEQ ID NO: 8 or 10 with at least one amino acid deletion, wherein the polypeptide has an activity of the polypeptide as set forth in SEQ ID NO: 8 or 10;

(d) the amino acid sequence as set forth in SEQ ID NO: 8 or 10 which has a C- and/or N-terminal truncation, wherein the polypeptide has an activity of the polypeptide as set forth in SEQ ID NO: 8 or 10; and (e) the amino acid sequence as set forth in SEQ ID NO: 8 or 10, with at least one modification selected from the group consisting of amino acid substitutions, amino acid insertions, amino acid deletions, C-terminal truncation, and N-terminal truncation, wherein the polypeptide has an activity of the polypeptide as set forth in SEQ ID NO: 8 or 10.

Also provided are fusion polypeptides comprising the amino acid sequences of (a)–(e) above.

The present invention also provides for an expression vector comprising the isolated nucleic acid molecules as set forth herein, recombinant host cells comprising recombinant nucleic acid molecules as set forth herein, and a method of producing a tmst2-receptor polypeptide comprising culturing the host cells and optionally isolating the polypeptide so produced.

A transgenic non-human animal comprising a nucleic acid molecule encoding a tmst2-receptor polypeptide is also encompassed by the invention. The tmst2-receptor nucleic acid molecules are introduced into the animal in a manner that allows expression and increased levels of the tmst2-receptor polypeptide, which may include increased circulating levels. The transgenic non-human animal is preferably a mammal.

Also provided are derivatives of the tmst2-receptor polypeptides of the present invention.

Additionally provided are selective binding agents such as antibodies and peptides capable of specifically binding the tmst2-receptor polypeptides of the invention. Such antibodies and peptides may be agonistic or antagonistic.

Pharmaceutical compositions comprising the nucleotides, polypeptides, or selective binding agents of the present invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents. The invention also provides for devices to administer a tmst2-receptor polypeptide encapsulated in a membrane.

The tmst2-receptor polypeptide(s) of the invention and its biologically active variant(s), analog(s) and fragment(s) maybe used for therapeutic and/or diagnostic purposes to treat, prevent and/or detect conditions resulting from the abnormal expression of tmst2-receptor polypeptide or from the abnormal expression of a putative tmst2-ligand or a member of the TNF family of ligands that bind to tmst2-receptor polypeptide caused by overreaction of the host or deficiency of a natural autoregulatory network such as frequently observed in sepsis, cachexia, auto-immune responses, inflammatory diseases, viral, bacterial and parasitic diseases, and cancer.

The invention encompasses diagnosing a pathological condition or a susceptibility to a pathological condition in a subject caused by or resulting from abnormal levels of tmst2-receptor polypeptide comprising determining the presence or amount of expression of the tmst2-receptor polypeptide in a sample; and comparing the level of said polypeptide in a biological, tissue or cellular sample from either normal subjects or the subject at an earlier time, wherein susceptibility to a pathological condition is based on the presence or amount of expression of the polypeptide.

The present invention also provides a method of assaying test molecules to identify a test molecule which binds to a tmst2-receptor polypeptide. The method comprises contacting a tmst2-receptor polypeptide with a test molecule and determining the extent of binding of the test molecule to the polypeptide. The method further comprises determining whether such test molecules are agonists or antagonists of a tmst2-receptor polypeptide. The present invention further provides a method of testing the impact of molecules on the expression of tmst2-receptor polypeptide or on the activity of tmst2-receptor polypeptide.

Methods of regulating expression and modulating (i.e., increasing or decreasing) levels of a tmst2-receptor polypeptide are also encompassed by the invention. One method comprises administering to an animal a nucleic acid molecule encoding a tmst2-receptor polypeptide. In another method, a nucleic acid molecule comprising elements that regulate or modulate the expression of a tmst2-receptor polypeptide may be administered. Examples of these methods include gene therapy, cell therapy, and anti-sense therapy as further described herein.

The tmst2-receptor polypeptide can be used for identifying ligands thereof. Various forms of "expression cloning" have been used for cloning ligands for receptors. See e.g., Davis et al., Cell 87:1161–1169 (1996). These and other tmst2-receptor ligand cloning experiments are described in greater detail herein. Isolation of the tmst2-receptor ligand (s) allows for the identification or development of novel agonists and/or antagonists of the tmst2-receptor signaling pathway. Such agonists and antagonists include tmst2-receptor ligand(s), anti-tmst2-receptor ligand antibodies and derivatives thereof, small molecules, or antisense oligonucleotides, any of which can be used for potentially treating one or more diseases or disorders, including those recited herein.

DETAILED DESCRIPTION OF THE INVENTION

The section headings herein are for organizational purposes only and are not to be construed as limiting the subject matter described therein.

Definitions:

The term "tmst2 receptor nucleic acid molecule" refers to a nucleic acid molecule comprising or consisting essentially of or comprising a nucleotide sequence as set forth in SEQ ID NO: 7 or 9, comprising or consisting essentially of a nucleotide sequence encoding the polypeptide as set forth in SEQ ID NO: 8 or 10, or nucleic acid molecules related thereto. Related nucleic acid molecules comprise or consist essentially of a nucleotide sequence that is about 70 percent identical to the nucleotide sequence as shown in SEQ ID NO: 7 or 9, or comprise or consist essentially of a nucleotide sequence encoding a polypeptide that is about 70 percent identical to the polypeptide as set forth in SEQ ID NO: 8 or 10. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NOS: 7 or 9, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID NOS: 8 or 10. Related nucleic acid molecules also include fragments of the above tmst2 receptor nucleic acid molecules which are at least about 10 contiguous nucleotides, or about 15, or about 20, or about 25, or about 50, or about 75, or about 100, or greater than about 100 contiguous nucleotides.

Related nucleic acid molecules also include fragments of the above tmst2-receptor nucleic acid molecules which encode a polypeptide of at least about 25 amino acid residues, or about 50, or about 75, or about 100, or greater than about 100 amino acid residues. Related nucleic acid molecules also include a nucleotide sequence encoding a polypeptide comprising or consisting essentially of a substitution and/or a deletion of one or more of the 198 amino acid residues set out in SEQ ID NO: 8. Related nucleic acid molecules also include a nucleotide sequence encoding a polypeptide comprising or consisting essentially of a substitution and/or a deletion of one or more of the amino acid residues set out in SEQ ID NO: 10. Related tmst2-receptor nucleic acid molecules include those molecules which comprise nucleotide sequences which hybridize under moderate or highly stringent conditions as defined herein with any of the above nucleic acid molecules. In preferred embodiments, the related nucleic acid molecules comprise sequences which hybridize under moderate or highly stringent conditions with the sequence as shown in SEQ ID NO: 7 or 9, or with a molecule encoding a polypeptide, which polypeptide comprises the sequence as shown in SEQ ID NO: 8 or 10, or with a nucleic acid fragment as defined above, or with a nucleic acid fragment encoding a polypeptide as defined above. It is also understood that related nucleic acid molecules include allelic or splice variants of any of the above nucleic acids, and include sequences which are complementary to any of the above nucleotide sequences.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosinie, 2,2-dimethyl-guanine, 2-methyladenine, 2-methylguaninie, 3-methylcytosine, 5-methylcytosine, N6-methyladenine, 7-methylguaninic, 5-methylaminomethyluracil, 5-metihoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosile, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosinc, 2-thiocytosine, and 2,6-diaminopurine.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "isolated nucleic acid molecule" refers to a nucleic acid molecule of the invention that (1) has been separated fromat least about 50 percent of proteins, lipids, carbohydrates or other materials with which it is naturally found when total DNA is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "allelic variant" refers to one of several possible naturally occurring alternate forms of a gene occupying a given locus on a chromosome of an organism.

The term "splice variant" refers to nucleic acid molecule, usually RNA, which is generated by alternative processing of introni sequences in an RNA transcript.

The term "expression vector" refers to a vector which is suitable for propagation in a host cell and contains nucleic acid sequences which direct and/or control the expression of inserted heterologous nucleic acid sequences. Expression includes, but is not limited to, processes such as transcription, translation, and RNA splicing, if introns are present.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in Genetic make-up to the original parent, so long as the selected gene is present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "pharmaceutically acceptable carrier" or "physiologically acceptable carrier" as used herein refers to one or more fonnulation materials suitable for accomplishing or enhancing the delivery of the tmst2-receptor-receptor like polypeptide, tmst2-receptor-receptor like nucleic acid molecule or tmst2-receptor-receptor like selective binding agent as a pharmaceutical composition.

The term "selective binding agent" refers to a molecule or molecules having specificity for an tmst2-receptor-receptor like polypeptide. As used herein, the terms, "specific" and "specificity" refer to the ability of the selective binding agents to bind to human tmst2-receptor-receptor like polypeptides and not to bind to human non-tmst2-receptor-receptor like polypeptides. It will be appreciated, however, that the selective binding agents may also bind orthologs of the polypeptide as set forth in SEQ ID NO: 8 or 10, that is, interspecies versions thereof, such as mouse and rat polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Gralham et al., *Virology*, 52:456 (1973); Sambrook et al. *Molecular Cloning, a Laboratory Manual*, Cold Spring Harbor Laboratories (New York, 1989); Davis et al., *Basic Methods in Molecular Biology*, Elsevier, 1986; and Chu et al., *Gene*. 13:197 (1981). Such techniques can be used to introduce one or more exogenous DNA moieties into suitable host cells.

The term "transformation" as used herein refers to a change in a cell's genetic characteristics, and a cell has been transfonred when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "tmst2-receptor polypeptide" refers to a polypeptide comprising the amino acid sequence of SEQ ID NO: 8 or 10, and related polypeptides described herein. Related polypeptides includes allelic variants, splice variants, fragments, derivatives, substitution, deletion, and/or insertion variants, fusion polypeptides, and orthologs. tmst2-receptor-receptor polypeptide(s) may be mature polypeptide(s), as defined herein, and may or may not have an amino terminal methionine residue, depending on the method by which they are prepared.

The term "tmst2-receptor polypeptide fragment" refers to a peptide or polypeptide that comprises less than the full length amino acid sequence of a tmst2-receptor polypeptide as set forth in SEQ ID NO: 8 or 10. Such a fragment may arise, for example, from a truncation at the amino terminus, a truncation at the carboxy terminus, and/or an internal deletion of the amino acid sequence. Tmst2-receptor fragments may result from alternative RNA splicing or from in vivo protease activity. For transmembrane or membrane-bound forms of a tmst2-receptor polypeptide, preferred fragments include soluble forms such as those lacking a transmembrane or membrane-binding domain.

The term "tmst2-receptor polypeptide variants" refers to tmst2-receptor polypeptides comprising amino acid sequences which contain one or more amino acid sequence substitutions, deletions (such as internal deletions and/or tmst2-receptor fragments), and/or additions (Such as internal additions and/or tmst2-receptor like fusion polypeptides) as compared to the tmst2-receptor polypeptide amino acid sequence set forth in SEQ ID NO:8 or 10. Variants may be naturally occurring (e.g., tmst2-receptor allelic variants, tmst2-receptor orthologs, and tmst2-receptor splice variants) or artificially constructed using recombinant DNA technology. Such tmst2-receptor polypeptide variants may be prepared from the corresponding nucleic acid molecules encoding said variants, which have a DNA sequence that varies accordingly from the DNA sequences for wild type tmst2-receptor polypeptides as set forth in SEQ ID NOS: 7 or 9. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "tmst2-receptor like polypeptide fragment" refers to a polypeptide that comprises a truncation at the amino terminus (with or without a leader sequence) and/or a truncation at the carboxy terminus of the polypeptide as set forth in SEQ ID NO: 8 or 10, tmst2-receptor polypeptide allelic variants, tmst2-receptor polypeptide orthologs, tmst2-receptor polypeptide splice variants and/or an tmst2-receptor polypeptide variant having one or more amino acid additions or substitutions or internal deletions (wherein the resulting polypeptide is at least 6 amino acids or more in length) as compared to the tmst2-receptor polypeptide amino acid sequence set forth in SEQ ID NO: 8 or 10, tmst2-receptor-receptor like polypeptide fragments may result from alternative RNA splicing or from in vivo protease activity. In preferred embodiments, truncations comprise about 10 amino acids, or about 20 amino acids or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids or about 100 amino acids, or about 150 amino acids, or about 200 amino acids. Such tmst2-receptor polypeptide fragments may optionally comprise an amino terminal methionine residue. It will be appreciated that such fragments can be used, for example, to generate antibodies to tmst2-receptor polypeptides.

The term "tmst2-receptor fusion polypeptide" refers to a fusion of tmst2-receptor polypeptide, fragment, variant, ortholog and/or derivative thereof, one or more amino acids (such as heterologous peptide or polypeptide), preferably at the amino- or carboxy- terminus of the tmst2-receptor polypeptide as set forth in SEQ ID NO: 8 or 10. A non-limiting example of such a fusion is a fusion between a tmst2 polypeptide of the present invention and the Fc fragment of an immunoglobulin molecule. Fusion polypeptides according to the present invention may have for example improved stability in vivo or in vitro, improved solubility or improved circulatory half-life.

The term "tmst2-receptor polypeptide derivatives" refers to tmst2-receptor polypeptides, variants, or fragments thereof, that have been chemically modified, as for example, by covalent attachment of one or more water soluble polymers, N-linked or O-linked carbohydrates, sugars, phosphates, and/or other such molecules. Such modifications may be introduced into the molecule by reacting targeted amino acid residues of the purified or chide protein with an organic derivatizing agent that is capable of reacting with selected side chains or terminal residues. The resulting covalent derivatives are also useful in programs directed at identifying residues important for biological activity. The derivatives are modified in a manner that is different from naturally occurring tmst2-receptor polypeptide either in the type or location of the molecules attached to the polypeptide. Derivatives further include deletion of one or more chemical groups naturally attached to the tmst2-receptor polypeptide.

The terms "biologically active tmst2-receptor polypeptides", "biologically active tmst2-receptor polypeptide fragments", "biologically active tmst2-receptor polypeptide variants", and "biologically active tmst2-receptor polypeptide derivatives" refer to tmst2-receptor polypeptides having at least one activity characteristic of a tmst2-receptor polypeptide, such as the ability to bind and neutralize TNF-like ligand activity in biological assays. Immunogenic fragments of tmst2-receptor polypeptide(s) are those capable of inducing in a host animal antibodies directed to the tmst2 fragment.

The term "isolated polypeptide" refers to a polypeptide of the present invention that (1) has been separated from at least about 50 percent of polynucleotides, lipids, carbohydrates or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "tmst2-receptor-receptor like polypeptide ortholog" refers to a polypeptide from another species that corresponds to tmst2-receptor polypeptide amino acid sequence as set forth in SEQ ID NO: 8 or 10. For example, mouse and human tmst2-receptor polypeptides are considered ortholog,s of each other.

The term "mature tmst2-receptor polypeptide" refers to a tmst2-receptor polypeptide lacking a leader sequence and may also include other modifications of a polypeptide such as proteolytic processing of the amino terminus (with or without a leader sequence) and/or the carboxy terminus, cleavage of a smaller polypeptide from a larger precursor, N-linked and/or O-linked glycosylation, and the like.

The term"mutein" refers to a mutant protein, polypeptide, variants, analogs or fragments of tmst2-receptor polypeptide. Muteins of tmst2-receptor polypeptide may be prepared by deletion, insertion, substitution, point mutation, truncation, addition, transposition, PCR amplification, site-directed mutagenesis or other methods known in the art.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The terms "effective amount" and "therapeutically effective amount" refer to the amount of a tmst2-receptor polypeptide necessary to support an observable level of one or more biological activities of the decoy TNF-receptor polypeptides as set forth above, to bring about a meaningful patient benefit, i.e. treatment, healing, prevention, or amelioration of a condition. When applied to an individual active ingredient, administered alone, the tenn refers to that ingredient alone. When applied to combinations, the teni refers to combined amounts of active ingredients that result in therapeutic effect, when administered in combination, serially or simultaneously. The tmst2-receptor polypeptides that have use in practicing the present invention may be naturally occurring full length polypeptides, or truncated polypeptides or variant homologs or analogs or derivatives or peptide fragments. Illustrative analogs include those in which one or more divergent amino acids between two species are substituted with the divergent amino acid from another species. Divergent amino acids may also be substituted with any other amino acid whether it be a conservative or a non-conservative amino acid.

Relatedness of Nucleic Acid Molecules and/or Polypeptides

The term "identity", as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypetides as the case may be, as determined by the match between two or more strings of nucleotide or amino acid sequences. "Identity" measures the percent of identical matches between the smaller of two or more sequences with gap alignments if any addressed by a particular mathematical model or computer program (i.e., "algorithms").

The term "similarity" is a related concept, but in contrast to "identity", refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If in the same example, there are 5 more positions where there are conservative substitutions, then the percent identity remains 50%, but the per cent similarity would be 75% (15/20). T herefore, in cases where there are conservative substitutions, the degree of similarity between twvo polypeptide sequences will be higher than the percent identity between those two sequences.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015M sodium chloride, 0.0015M sodium citrate at 65–68° C. or 0.015M sodium chloride, 0.0015M sodium citrate, and 50% formamide at 42° C. See Sambrook, Fritsch & Maniatis, Molecular Cloning: A Laboratory Manual, 2nd Ed., Cold Spring Harbor Laboratory, (Cold Spring Harbor, N.Y. 1989); and Anderson et al., *Nutcleic Acid Hybridisation: a practical approach*, Ch. 4, IRL Press Limited (Oxford, England).

More stringent conditions (such as higher temperature, lower ionic strength, higher formamide, or other denaturing agent) may also be used,used; however, the rate of hybridization will be affected. Other agents may be included in the hybridization and washing buffers for the purpose of reducing non-specific and/or background hybridization. Examples are 0.1% bovine serum albumin, 0.1% polyvinylpyrrolidone, 0.1% sodium pyrophosphate, 0.1% sodium dodecylsulfate (NaDodSO4 or SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8–7.4,6.8–7.4; however, at typical ionic strength conditions, the rate of hybridization is nearly independent of pH. See Anderson et al., *Nucleic Acid Hybridisaition: a Practical Approach*, Ch. 4, IRL Press Limited (Oxford, England).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$Tm(° C.)=81.5+16.6(\log[Na+])+0.41(\%G+C)-600/N-0.72(\%formamide)$$

where N is the length of the duplex formed, [Na+] is the molar concentration of the sodium ion in the hybridization or washing solution, %G+C is the percentage of (guanine+cytosine) bases in the hybrid. For imperfectly matched hybrids, the melting temperature is reduced by approximately 1° C. for each 1% mismatch.

The term "moderately" moderately stringent conditions "conditions" refers to conditions under which a DNA duplex with a greater degree of base pair mismatching than could occur under "highly stringent conditions" is able to form. Examples of typical "moderately" moderately stringent conditions "conditions" are 0.015M sodium chloride, 0.001 5M sodium citrate at 50–65° C. or 0.015M sodium chloride, 0.0015M sodium citrate, and 20% formamide at 37–50° C. By way of example, a "moderately stringent" "moderately stringent" condition of 50° C. in 0.015M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$Tm=2° C. \text{ per A-T base pair}+4° C. \text{ per G-C base pair}$$

*The sodium ion concentration in 6×salt sodium citrate (SSC) is 1M. See Suggs et al., *Developiential Biology Using Purified Genes*, p. 683, Brown and Fox (eds.) (1981). High stringency washing conditions for oligonucleotides arc usually at a temperature of 0–5° C. below the Tm of the oligonucleotide in 6×SSC, 0.1% SDS.

The term "conservative amino acid substitution" refers to a substitution of a native amino acid residue with a nonnative residue such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alaninie, as has been previously described for "alaninie scanning mutagenesis". General rules for conservative amino acid substitutions are set forth in Table I.

TABLE I

| Conservative Amino Acid Substitutions | | | | |
|---|---|---|---|---|
| Basic: | Acidic: | Uncharged Polar: | Non-Polar: | |
| argininc | glutamic acid | glutamine | phenylalanine | valine |
| lysine | aspartic acid | asparagine | tryptophan | proline |
| histidine | | serine | cysteine | methionine |
| | | threonine | glycine | leucine |
| | | tyrosine | alanine | norleucine |
| | | | | soleticine |

Conservative modifications to the amino acid sequence (and the corresponding modifications to the encoding nucleotides) are expected to produce tmst2-receptor having functional and chemical characteristics similar to those of naturally occurring tmst2-receptor. In contrast, substantial modifications in the functional and/or chemical characteristics of tmst2-receptor may be accomplished by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

Naturally occurring residues may be divided into groups based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;

5) residues that influence chain orientation: Gly, Pro; and 6) aromatic: Trp, Tyr, Phe.

Non-conservative substitutions may involve the exchange of a member of one of these classes for a member from another class. Such substituted residues may be introduced into regions of the human tmst2-receptor molecule that arc homologous with non-human tmst2-receptor or into the non-homologous regions of the molecule.

Conservative amino acid substitutions also encompass non naturally occurring amino acid residues which are typically incorporated by chemical peptide synthesis rather than by synthesis in biological systems. These include peptidomimetics and other reversed or inverted forms of amino acid moieties.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparaginc (−3.5); lysine (−3.9); and arginine (−4.5).

The importance of the hydropathic amino acid index in conferring interactive biological function on a protein is understood in the art. Kyte et al., *J. Mol. Biol.*, 157:105–131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property to the protein.

The following hydrophilicity values have been assigned to amino acid residues: argininie (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidinie (−0.5); cysteine (−1.0); methioninie (−1.3); valine (−1.5); leucine (−1.8); isoleucine (−1.8); tyrosine (−2.3); phenylalanine (−2.5); tryptophan.(−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the tmst2-recptor-receptor like polypeptide, or to increase or decrease the affinity of the tmst2-receptor-receptor like polypeptides described herein.

Exemplary amino acid substitutions are set forth in Table II.

TABLE II

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to deteniine suitable variants of the polypeptide as set forth in SEQ ID NO: 8 or 10 using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of an tmst2-receptor polypeptide to such similar polypeptides. With such a comparison, one can identify residues and portions of the molecules that are conserved among similar polypeptides. It will be appreciated that changes in areas of an tmst2-receptor polypeptide that are not conserved relative to such similar polypeptides would be less likely to adversely affect the biological activity and/or structure of the tmst2-receptor polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in an tmst2-reccptor-receptor like polypeptide that correspond to amino acid residues that are important for activity or structure in similar polypeptides. One skilled in the art may opt for chemically similar amino acid substitutions for such predicted important amino acid residues of tmst2-receptor polypeptides.

One skilled in the art can also analyze the three-dimensional structure and amino acid sequence in relation to that structure in similar polypeptides. In view of that information, one skilled in the art may predict the alignment of amino acid residues of an tmst2-receptor polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where luither substitutions should be avoided either alone or in combination with other mutations.

A number of scientific publications have been devoted to the prediction of secondary structure. See Moult J., *Curr. Opin. in Biotech.*, 7(4); 422–427 (1996), Chou et al. *Biochemnistry*, 13(2):222–245 (1974); Chou et al. *Biochemistry*, 113(2):211–222 (1974); Chou et al., *Adv. Enzymol. Relat. Areas Mol. Biol.*, 47:45–148 (1978); Chou et al., *Ann. Rev. Biochem.*, 47:251–276 and Chou et al., *Biophys. J.*, 26:367–384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., *Nucl. Acid. Res.*, 27(1):244–247 (1999). It has been suggested (Brenner et al., *Curr. Opin. Struct. Biol.*, 7(3):369–376 (1997)) that there are a limited number of folds in a given polypeptide or protein and that once a critical number of structures have been resolved, structural prediction will gain dramatically in accuracy.

Additional methods of predicting secondary structure include "threading" (Jones, D., *Curr. Opin. Struct. Biol.*, 7(3):377–87 (1997); Sippl et al, *Structure*, 4(1):15–9 (1996)), "profile analysis" (Bowie et al., *Science*, 253:164–170 (1991); Gribskov et al., *Meth. Enzyn.*, 183:146–159 (1990); Gribskov et al., *Proc. Nat. Acad. Sci. USA*, 84(13):4355–4358 (1987)), and "evolutionary linkage" (See Home, supra, and Brenner, supra).

Preferred tmst2-receptor-receptor like polypeptide variants include glycosylation variants wherein the number and/or type of glycosylation sites has been altered compared to the amino acid sequences set forth in SEQ ID NO: 8 and 10. In one embodiment, tmst2-receptor polypeptide variants comprise a greater or a lesser number of N-linked glycosylation sites than the amino acid sequences set forth in SEQ ID NO: 8 and 10. An N-linked glycosylation site is characterized by the sequence: Asn-X-Ser or Asn-X-Thr vlwhercin the amino acid residue designated as X may be any amino acid residue except proline. The substitution(s) of amino acid residues to create this sequence provides a potential new site for the addition of an N-linked carbohydrate chain. Alternatively, substitutions which eliminate this sequence will remove an existing N-linked carbohydrate chain. Also provided is a rearrangemenit of N-linked carbohydrate chains wherein one or more N-linked glycosylation sites (typically those that are naturally occurting) are eliminated and one or more new N-linkcd sites are created. Additional preferred tmst2-receptor variants include cysteine variants, wherein one or more cysteine residues are deleted from or substituted for another amino acid (e.g., serine) as compared to the amino acid sequences set forth in SEQ ID NO: 8 and 10. Cysteine variants are useful when tmst2-receptor polypeptides must be refolded into a biologically active conformation Such as after the isolation of insoluble inclusion bodies. Cysteine variants generally have fewer cysteine residues than the native protein, and typically have an even number to minimize interactions resulting from unpaired cystcines.

In addition, the polypeptide comprising the amino acid sequence of SEQ ID NO: 8 or 10 or a tmst2-receptor polypeptide variant may be fused to a homologous polypeptide to form a homodimer or to a heterologous polypeptide to form a heterodimer. Heterologous peptides and polypeptides include, but are not limited to: an epitope to allow for the detection and/or isolation of an tmst2-receptor fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in SEQ ID NO: 8 or 10 or an tmst2-receptor-receptor like polypeptide variant.

Fusions can be made either at the amino terminus or at the carboxy terminus of the polypeptide comprising the amino acid sequence set forth in SEQ ID NO: 8 or 1 0 or an tmst2-receptor polypeptide variant. Fusions may be direct with no linker or adapter molecule or indirect Lisin a linker or adapter molecule. A linker or adapter molecule may be one or more amino acid residues, typically up to about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of SEQ ID NO: 8 or 10 or a tmst2-receptor polypeptide variant is fused to one or more domains of an Fc region of human IgG. Antibodies comprise two functionally independent parts, a variable domain known as "Fab", which binds antigen, and a constant domain known as "Fc", which is involved in effector functions such as complement activation and attack by phagocytic cells. An Fc has a long serum half-life, whereas an Fab is short-lived. Capon et al., *Nature*, 337:525–31 (1989). When constructed together with a therapeutic protein, an Fc domain can provide longer half-life or incorporate such functions as Fc receptor binding, protein A binding, complement fixation and perhaps even placental transfer. Id. Table III summarizes the use of certain Fc fusions known in the art.

TABLE III

Fc Fusion with Therapeutic Potential

| Form of Fc | Fusion partner | Therapeutic implications | Reference |
|---|---|---|---|
| IgG1 | N-terminus of CD30-L | Hodgkin's disease; anaplastic lyphoma; T-cell leukemia | U.S. Pat. No. 5,480,981 |
| Murine Fcg2a | IL-10 | anti-inflammatory; transplant rejection | Zheng et al. (1995), J. Immunol. 154: 5590–5600 |
| IgG1 | TNF receptor | septic shock | Fisher et al. (1996), N. Engl. J. Med., 334: 1697–1702; Van Zee et al., (1996), J. Immunol., 156: 2221–2230 |
| IgG, IgA, IgM, or IgE (excluding the first domain) | TNF receptor | inflammation, autoimmune disorders | U.S. Pat. No. 5,808,029, issued Sept. 15, 1998 |
| IgG1 | CD4 receptor | AIDS | Capon et al. (1989), Nature 337: 525–531 |
| IgG1, IgG3 | N-terminus of IL-2 | anti-cancer, antiviral | Harvill et al. (1995), Immunotech., 1: 95–105 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cg1 | CTLA-4 | autoimmune disorders | Linsley (1991), J. Exp. Med., 174: 561–569 |

In one example, all or a portion of the human IgG hinge, CH2 and CH3 regions may be fused at either the N-terminus or C-terminius of the tmst2-receptor-receptor like polypeptides using methods known to the skilled artisan. The resulting tmst2-receptor fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/mutltimerization of the fusion polypeptide. The Fc region may be a naturally occurring Fc region, or may be altered to improve certain qualities, such as therapeutic qualities, circulation time, reduce aggregation, etc.

Identity and similarity of related nucleic acid molecules and polypeptides can be readily calculated by known methods. Such methods include, but are not limited to, those described in *Computational Molecular Biology*, Lesk, A. M., ed., Oxford University Press, (New York, 1988); *Biocomputing: Informatics and Genosme Projects*, Smith, D. W., ed., Academic Press, (New York, 1993); *Computer Analysis of Sequence Data*, Part 1, Griffin, A. M., and Griffin, H. G., eds., Humania Press, (New Jersey, 1994); *Sequence Analysis in Molecular Biology*, von Heinje, G., Academic Press, (1987); *Sequence Analysis Primer*, Gribskov, M. and Devereux, J., eds., M. Stockton Press, (New York, 1991); and Carillo et al., *SIAM J. Applied Math.*, 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux, et al., *Nucleic Acids Research* 12(1):387 (1984); Genetics Computer Group, University of Wisconsin, Madison, Wis.), BLASTP, BLASTN, and FASTA (Atschul, et al., *J. Molec. Biol.* 215:403–410 (1990). The BLAST X program is publicly available from the National Center for Biotechnology Information (NCBI) and other sources (BLAST Manual, Altschul, et al. NCB NLM NIH Bethesda, Md. 20894; Altschul, et al., *J. Mol. Biol.* 215:403–410 (1990). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least 50 contiguous amino acids of the target polypeptide.

For example, Usitlg the computer algorithm GAP (Genetics Computer Group, (University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. A standard comparison matrix (see Dayhoff et al, in: *Atlas of Proteint Sequtence and Structure*, vol. 5, supp.3 (1978) for the PAM 250 comparison matrix; see Henikoff et al., *Proc. Natl. Acad. Sci USA*, 89:10915–10919 (1992) for the BLOSUM 62 comparison matrix) is also used by the algorithm.

Preferred parameters for a polypeptide sequence comparison include the following:

Algorithm: Needleman and Wunsch, *J. Mol. Biol.* 48:443–453 (1970), Comparison matrix: BLOSUM 62 from Henikoff and Hienikoff, *Proc. Natl. Acad. Sci. USA* 89 10915–10919 (1992).

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following:

Algorithm: Needleman and Wunsch, *J. Mol Biol.* 48:443–453 (1970)

Comparison matrix: matches+10, mismatch=0

Gap Penalty: 50

Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version Sep. 9, 1997. The particular choices to be made will depend on the specific comparison to be made, such as DNA-to-DNA, protein-to-protein, protein-to-DNA;

and additionally, whether the comparison is between given pairs of sequences (in which case GAP or BestFit are generally preferred) or between one sequence and a large database of sequences (in which case FASTA or BLASTA are preferred).

Certain alignment schemes for aligning two amino acid sequences may result in matching of only a short region of the two sequences, and this small aligned region may have very high sequence identity even though there is no significant relationship between the two ftill length sequences. Accordingly, in a preferred embodiment, the selected alignment method will result in an alignment that spans at least about 66 contiguous amino acids of the claimed full length polypeptide.

Synthesis

It will be appreciated by those skilled in the art the nucleic acid and polypeptide molecules described herein may be produced by recombinant and other means.

Nucleic Acid Molecules

The nucleic acid molecules encode a polypeptide comprising the amino acid sequence of an tmst2 like polypeptide can readily be obtained in a variety of ways including without limitation, chemical synthesis, cDNA or genomic library screening, expression library screening and/or PCR amplification of cDNA.

Recombinant DNA methods used herein are gYenerally, but not limited to, those set forth in Sambrook et al. (*Molecular Cloning: A Laboratory Manual*, Cold Spring Harbor Laboratory Press, Cold Spring Harbor, N.Y. (1989)) and/or Ausubel et al., eds., (*Current Protocols in Molecular Biology*, Green Publishers Inc. and Wiley and Sons, NY (1994)).

The present invention provides for nucleic acid molecules as described herein and methods for obtaining the molecules. A gene or cDNA encoding a "tmst2 receptor polypeptide" or fragment thereof may be obtained by hybridization screening of a genomic or cDNA library, or by PCR amplification. Probes or primers useful for screening a library by hybridization can be generated based on sequence infornation for other known genes or gene fragments fromt the same or a related family of genes, such as, for example, conserved motifs. In addition, where a gene encoding tmst2-receptor polypeptide has been identified from one species, all or a portion of that gene may be used as a probe to identify corresponding genes from other species (orthologs) or related genes from the same species (homologs). The probes or primers may be used to screen cDNA libraries from various tissue sources believed to express the "tmst2-receptor gene".

In addition, part or all of a nucleic acid molecule having the sequence as set forth in SEQ ID NO: 7 or 9 may be used to screen a genomic library to identify and isolate a gene encoding "tmst2 receptor." Typically, conditions of moderate or high stringency will be employed for screening to minimize the number of false positives obtained from the screen.

The availability of the cDNA coding for the tmst2-receptor or fractions thereof is the prerequisite for obtaining the genomic DNA. Under stringent conditions, a DNA library is screened and the clones obtained are investigated to see whether they contain the regulatory sequence elements needed for gene expression in addition to the coding regions (e.g. checking for promoter function by fusion with coding regions of suitable reporter genes). Methods for screening DNA libraries under stringent conditions are taught, for example, in EPA 0 174 143, incorporated herein by reference. Obtaining, the genomic DNA sequence makes it possible to investigate the regulatory sequences situated in the area which does not code for the "tmst2-receptor", particularly in the 5'-flanking region, for any possible interaction with known substances which modulate gene expression, e.g. transcription factors or steroids, or possibly discover new substances which might have a specific effect on the expression of this gene. The results of such investigations provide the basis for the targeted use of such substances for modulating tmst2-receptor expression and hence for directly influenicing, the ability of the cells to interact with TNF family of ligands. As a result the specific reaction with the ligands and the resulting effects can be suppressed.

The scope of the present invention also includes DNAs which code for subtypes of the tmst2-receptor or its soluble forms, which may have properties different from those of the present tmst2-receptor. These are expression products which are formed by alternative splicing and have modified structures in certain areas, e.g. structures which can bring about a change in the affinity and specificity for the ligand or a change in terms of the nature and efficiency of signal transmission.

With the aid of the cDNA coding for the tmst2-receptor it is possible to obtain nucleic acids which hybridize with the cDNA or fragments thereof under conditions of low stringency and code for a polypeptide capable of binding TNF-related ligands or contain the sequence coding for such a polypeptide.

According to a further aspect, the invention relates to recombinant tmst2-receptor polypeptide(s), preferably in a secretable form, which constitutes the soluble part of the tmst2-receptor. The invention also contemplates the production of a soluble fonn of the tmst2-receptor, which is secreted into the cell supernatant, by recombinant DNA technology wherein the DNA coding for tmst2-receptor with a sequence coding for a signal peptide under the control of a suitable promoter is introduced into suitable host organisms, especially eukaryotic and preferably higher eukaryotic cells.

Nucleic acid molecules encoding tmst2-receptor polypeptides may also be identified by expression cloning which employs the detection ofpositive clones based upon a property of the expressed protein. Typically, nucleic acid libraries are screened by binding of an antibody or other binding partner (e.g., receptor or ligand) to cloned proteins which are expressed and displayed on a host cell surface. The antibody or the binding partner is modified with a detectable label to identify those cells expressing the desired clone.

Two murine TNF receptors, tmst2-receptor described herein, and ymkz5-receptor (cloned by Amgen), have been identified to be closely linked within the murine genome. Both of these novel receptors bind TRAIL in a species specific manner (See Example 9). Therefore. the characterization of the murine genes, tmst2 and ymkz5, may aid in the discovery of human TRAIL decoy receptors based on functionality and not solely based on primary sequence homology. Identification of human tmst2/ymkz5 orthologs of the invention will be facilitated by chromosomal and structural studies to reveal two highly related genes which are closely linked on the chromosome, one which is GPI-linked and the other a transmembrane receptor. Alternatively, the human genome may only harbor one ortholog which may be identified in the region syntenic with the mouse tmst2/ymkz5 locus.

Recombinant expression techniques conducted in accordance with the descriptions set forth below may be followed to produce these polynucleotides and to express the encoded polypeptides. For example, by inserting a nucleic acid sequence which encodes the amino acid sequence of a tmst2-receptor polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a tmst2-receptor polypeptide can be inserted into an expression vector. By introducing the expression vector into an appropriate host, the encoded tmst2-receptor polypeptide may be produced in large amounts.

Another method for obtaining a suitable nucleic acid sequence is the polyierase chain reaction (PCR). In this method, cDNA is prepared from poly(A)+RNA or total RNA using the enzyme reverse transcriptase. Two primers, typically complementary to two separate regions of cDNA (oligonucleotides) encoding the amino acid sequence of an tmst2-receptor polypeptide, are then added to the cDNA along with a polymerase such as Taq polymerase, and the polymerase amplifies the cDNA region between the two primers.

Another means of preparing a nucleic acid molecule encoding a variant tmst2-receptor polypeptide or a biologically active fragment thereof is by chemical synthesis using methods well known to the skilled artisan such as those described by Engels et al.(*Angew. Chem. Intl. Ed.*, 28:716–734 (1989)). These methods include, inter alia, the phosphotriester, phosphoramidite, and H-phosphoniate methods for nucleic acid synthesis. A preferred method for such chemical synthesis is polymer-supported synthesis using standard phosphoramiditc chemistry. Typically. the DNA encoding the tmst2-receptor polypeptide will be several hundred nucleotides in lengtth. Nucleic acids larger than about 100 nucleotides can be synthesized as several fragments using these methods. The fragments can then be ligated together to form the full length tmst2-receptor polypeptide. Usually, the DNA fragment encoding the amino terminus of the polypeptide will have an ATG, which encodes a methionine residue. This methionilne may or may not be present on the mature form of the tmst2-receptor polypeptide, depending on whether the polypeptide produced in the host cell is designed to be secreted from that cell.

In some cases, it may be desirable to prepare nucleic acid molecules encoding tmst2-receptor polypeptide variants or muteins. Nucleic acid molecules encoding variants may be produced using site directed mutagenesis, transposition, deletion, addition, truncation, PCR amplification, or other appropriate methods, where the primer(s) have the desired point mutations (see Sambrook et al., supra, and Ausubel et al., supra, for descriptions of mutagenesis techniques), provided that DNA's modified in this way code for polypeptides capable of binding one or more members of the TNF-family. Chemical synthesis using methods described by Engels et al., supra, may also be used to prepare such variants. Other methods known to the skilled artisan may be used as well.

In certain embodiments, nucleic acid variants contain codons which have been altered for the optimal expression of a tmst2-receptor polypeptide in a given host cell. Particular codon alterations will depend upon the tmst2-receptor polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh. cod" for codon preference of highly expressed bacterial genes may be used and are provided by the University of Wisconsin Package Version 9.0, Genetics Computer Group, Madison, Wis. Other useful codon frequency tables include "Celecans_high.cod", "Celegans_low.cod", "Drosophila_high.cod", "Human_high.cod", "Maize_high.cod", and "Yeast_high.cod".

In other embodiments, nucleic acid molecules encode tmst2-receptor variants with conservative amino acid substitutions as defined above, tmst2 receptor variants comprising an addition and/or a deletion of one or more N-linked or O-linked glycosylationi sites, or tmst2-receptor polypeptide fragments as described above. In addition, nucleic acid molecules may encode any combination of tmst2-receptor variants. fragments, and fusion polypeptides described herein provided that DNA's modified in this way code for polypeptides capable of finding one or more members of TNF super gene family of ligands and receptors.

Expression of tmst2 in Eukaryotic and Prokaryotic Cells

A nucleic acid molecule encoding a tmst2-receptor polypeptide may be inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding a tmst2-reccptor polypeptide may be amplified/expressed in prokaryotic, yeast, insect (baculovirus systems) and/or eukaryotic host cells. Selection of the host cell will depend in part on whether the tmst2-receptor polypeptide is to be post-translationally modified (e.g, glycosylated and/or phosphorylated). lfso, yeast, insect, or mammalian host cells are preferable. For a reveiw of expression vector, see *Meth. Enz.* vol. 185, D.V. Goeddel ed. Academic Press, Inc., San Diego, Calif. (1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one of the following nucleotides: a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag" sequence, i.e., an oligonucleotide molecule located at the 5' or 3' end of the tmst2-receptor polypeptide coding sequence; the oligonucleotide molecule encodes polyHis (such as hexaHis), or other "tag" such as FLAG, HA (hemaglutinin Influenza virus) or myc for which commercially available antibodies exist. Optionally, the tmst2 gene can also be fused in frame at the N-terminal for example to an IgG Fc region. This tag is typically fused to the polypeptide upon expression of the polypeptide, and can serve as means for affinity purification of the tmst2-receptor polypeptide from the host cell althougLh it may also prolong the circulatory half life of a tmst2 polypeptide. Affinity purification can be accomplished, for example, by column chromatography using antibodies or protein-A column against the tag as an affinity matrix. Optionally, the tag can subsequently be removed from the purified tmst2-receptor polypeptide by various means such as using certain peptidases for cleavage.

The 5'-flanking region of a gene contains a nucleic acid sequence to which RNA polymerase binds and initiates transcription. This nucleic sequences, known as the promoter region, determines both the nature of the enzyme that attaches to it and the rate of RNA synthesis. A number of eukaryotic and prokaryotic promoter elements are known in the art and are used to enhance gene transcription. Flanking sequneces may be homologous (i.e., from the same species and/or strain as the host cell), heterologous (i.e, from a species other than the host cell species or strain), hybrid (i.e., a combination of gene flanking sequences from more than one source), or synthetic, or the flanking sequences may be native sequences which normally function to regulate tmst2-receptor expression. As such, the source of a flanking sequence may be any prokaryotie or eukaryotic organism, any vertebrate or invertebrate organism, or any plant, provided that the flanking sequences is functional in, and can be activated by, the host cell machinery.

The flanking sequences useful in the vectors of this invention may be obtained by any of several methods well known in the art. Typically, flanking sequences useful herein other than the endogenoLs tmst2-receptor gene flanking sequence will have been previously identified by mapping and/or by restriction endonuclease digestion and can thus be isolated from the proper tissue source using the appropriate restriction endonucleases. In some cases, the full nucleotide sequence of one or more flanking sequence may be known. Here, the flanking sequence may be synthesized using the methods described above for nucleic acid synthesis or cloning.

Where all or only a portion of the flanking sequence is known, it may be obtained using PCR and/or by screening a genomic library with suitable oligonucleotide and/or flanking sequence fragments from the same or another species.

Where the flanking sequence is not known, a fragmnent of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarosc gel purification, QIAGEN® column chromatography (Chatsworth, Calif.). or other methods known to the skilled artisan. The selection of suitable enzymes to accomplish this purpose will be readily apparent to one of ordinary skill in the art.

An origin of replication is typically a part of those prokaryotic expression vectors purchased commercially, and the origen aids in the amplification of the vector in a host cell. Amplification of the vector to a certain copy number can, in some cases, be important for the optimal expression of the tmst2-receptor polypeptide. If the vector of choice does not contain an origin of replication site, one may be chemically synthesized based on a known sequence, and ligated into the vector. For example, the origin of replication from the plasmid pBR322 (Product No. 303-3s, New England Biolabs, Beverly, Mass.) is suitable for most Gram-negative bacteria and various origins (e.g., SV 40, polyoma, adenovirus, vesicular stomatitus virus (VSV) or papilloma viruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly T sequence. While the sequence is easily cloned from a library or even purchased commercially as part of a vector, it can also be readily synthesized using methods for nucleic acid synthesis such asthose described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may be used for selection in prokaryotic and eukaryotic host cells.

Other selection g,enes may be used to amplify the gcne which will be expressed. Amplification is the process wherein genes which are in greater demand for the production of a protein critical for growth are reiterated in tandem within the chromosomes of successive generations of recombinant cells. Examples of suitable, amplifiable, selectable markers for mammalian cells include dihydrofolate reductase (DHFR) and thymidile kinase. The mammalian cell transformants are placed under selection pressure which only the tranisformants are uniquely adapted to survive by virtue of the marker present in the vector. Selection pressure is imposed by culturing the transformed cells under conditions in which the concentration of selection agent in the medium is successively changed, thereby leading to the amplification of both thes election gene and the DNA that encodes tmst2-receptor. As a result, increased quantities of tmst2-receptor polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the tmst2-receptor polypeptide to be expressed. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

A leader, or signal, sequence may be used to direct the secretion of tmst2-receptor polypeptide out of the host cell where it is synthesized. Typically, the signal sequence is positioned in the coding region of the tmst2-receptor nucleic acid molecule, or directly at the 5' end of the tmst2-receptor polypeptide coding region. Many signal sequences have been identified, and any ofthose that are functional in the selected host cell may be used in conjunction with the tmst2-receptor gene or cDNA. Therefore, a signal sequence may be homologous (naturally occurring) or heterologotis to the tmst2-receptor gene or cDNA, and may be homologous or heterologous to the tmst2-receptor gene or cDNA. Additionally, a signal sequence may be chemically synthesized using methods described herein. In most cases, the secretion of an tmst2-receptor polypeptide from the host cell via the presence of a signal peptide will result in the removal of the signal peptide from the tmst2-receptor polypeptide.

The signal sequnce may be a component of the vector, or it may be a part of tmst2-recceptor DNA that is inserted into the vector. The native tmst2-receptor DNA encodes a signal sequence at the amino terminus of the protein that is cleaved during post-translational processing of the molecule to form the mature tmst2-receptor protein product. Included within the scope of this invention are tmst2-receptor nucleotides with the native signal sequence as well as tmst2-receptor nucleotides wherein the native signal sequence is replaced with, a heterologous signal sequence joined to tmst2-receptor polypeptide coding region. The heterologous signal sequence selected should be one that is recognized and processed, i.e., cleaved by a signal peptidase, by the host cell. For prokaryotic host cells that do not recognize and process the native tmst2-receptor signal sequence, the signal sequence is substituted by a prokaryotic signal sequence selected, for example, from the group of the alkaline phosphatase, penicillinase, or heat-stable enterotoxin II leaders. For yeast secretion, the native tmst2-receptor signal sequence may be substituted by the yeast invertase, alpha factor, or acid phosphatase leaders. In mammalian cell expression the native signal sequence of the tmst2-receptor polypeptide is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add presequences, which also may affect glycosylation. The final protein product may have, in the −1 position (relative to the first amino acid of the mature protein) one or more additional amino acid residues incident to expression, which may not have been totally removed. For example, the final protein product may have one or two amino acids found in the peptidase cleavage site, attached to the N-terminus. Alternatively, use of some enzyme cleavage sites may result in a slightly truncated form of the desired tmst2-receptor polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns may be naturally occurring within the tmst2-receptor uene, especially where the gene used is a full length genomic sequence or a frament thereof. Where the intron is not naturally occurring within the gene (as for most cDNAs), the intron(s) may be obtained from another source. The position of the intron with respect to 5'-flanking sequences and the tmst2-receptor gene is generally important, as the intron must be transcribed to be effective. Thus, when an tmst2-receptor cDNA molecule is being, expressed, the preferred position for the intron is 3' to the transcription start site, and 5' to the polyA transcription termination sequence. Preferably, the intron or introns will be located on one side or the other (i.e., 5' or 3') of the cDNA such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

The expression and cloning vectors of the present invention will typically contain a promoter that is recognized by the host organism and operably linked to the molecule encoding the tmst2-receptor protein.

Promoters are untranslated sequences located upstream (5') to the start codon of a structural gene (generally within about 100 to 1000 bp) that control the transcription and translation of a particular molecule, such as that encoding tmst2-receptor. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding tmst2-receptor by removing the promoter from the source DNA by restriction enzyme digestion and inserting the desired promoter sequence into the vector. The native tmst2-receptor promoter sequence may be used to direct amplification and/or expression of tmst2-receptor encoding DNA. A heterologous promoter is preferred, however, if it permits greater transcription and higher yields of the expressed protein as compared to the native promoter, and if it is compatible with the host cell system that has been selected for use.

Promoters suitable for use with prokaryotic hosts include, but are not limited to the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence (s), using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, herpes virus and most preferably Simian Virus 40 (SV40). Other suitable mammalian promoters include heterologous mammalian promoters, e.g., heat-shock promoters and the actin promoter.

Additional promoters which may be of interest in controlling tmst2 expression include, but are not limited to, the SV40 early promoter region (Bernoist and Chambon, *Nature*, 290:304–310 (1981)); the CMV promoter; the promoter contained in the 3' long terminal repeat (LTR) of Rous sarcoma virus (RSV) (Yamamoto et al., *Cell*, 22:787–797 (1980)); the herpes thymidine kinase promoter (Wagner et al., *Proc. Natl. Acad. Sci. U.S.A.*, 78:144–1445 (1981)); the regulatory sequences of the metallothionine gene (Brinster et al., *Nature*, 296:39–42 (1982)); prokaryotic expression vectors such as the beta -lactamase promoter (Villa-Kamaroff et al., *Proc. Natl. Acad. Sci. U.S.A.*, 75:3727–3731 (1978)); or the tac promoter (DeBoer et al., *Proc. Nati. Acad. Sci. U.S.A.*, 80:21–25 (1983)). Also of interest are the following animal transcriptional control regions, which exhibit tissue specificity and have been utilized in transgenic animals: the elastase I gene control region which is active in pancreatic acinar cells (Swift et al., *Cell*, 38:639–646 (1984); Ornitz et al., *Cold Spring Harbor Symp. Quant. Biol.* 50:399–409, (1986); MacDonald, *Hepatology*, 7:425–515 (1987)); the insulin gene control region which is active in pancreatic beta cells (Hanahan, *Nature*, 315:115–122 (1985)); the immunoglobulin gene control region which is active in lymphoid cells (Grosschedl et al., *Cell*, 38:647–658 (1984); Adames et a., *Nature*, 318:533–538 (1985); Alexander et al., *Mol. Cell. Biol.*, 7:1436–1444 (1987)); the mouse mammary tumor virus control region which is active in testicular, breast, lymphoid and mast cells (Leder et al, Cell, 45:485–495 (1986)), the albumin gene control region which is active in liver (Pinkert et al., Genes and Devel., 1:268–276 (1987)); the alpha-feto-protein gene control region which is active in liver (Krumlauf et al., Mol. Cell. Biol., 5:1639–1648 (1985); Hammer et al., Science, 235:53–58 (1987)); the alpha 1-antitrypsin gene control region which is active in the liver (Kelsey et atl., Genes and Devel., 1:161–171(1987)); the beta-globin gene control region which is active in myeloid cells (Mogram et al., Nature, 315:338–340 (1985); Kollias et al., Cell, 46:89–94 (1986)); the myelin basic protein gene control region which is active in oligodenidrocyte cells in the brain (Readhead et al., Cell, 48:703–712, (1987)); the myosin light chain-2 gene control region which is active in skeletal muscle (Sani, Nature, 314:283–286 (1985)); and the gonadotropic releasing hormone gene control region which is active in the hypothalamus (Mason et al., Science, 234:1372–1378 (1986)).

An enhancer sequence may be inserted into the vector to increase the transcription of a DNA encoding a tmst2-receptor polyepeptide by higher eukaryotes. Enhancers are cis-acting elements of DNA, usually about 10–300 bp in length, that act on the promoter to increase its transcription. Enhancers are relatively orientation and position independent. They have been found 5' and 3' to the transcription unit. Several enhancer sequences available from mammalian genes are known (e.g., globin, clastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation or upregulation of eukaryotic promoters. While an enhancer may be spliced into the vector at a position 5' or 3' to tmst2-receptor DNA, it is typically located at a site 5' from the promoter.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors inilcude, inter alia, pCRII, pCR3, and pcDNA3.1 (Invitrogen Company, Carlsbad, Calif.), pBSII (Stratagene Company, La Jolla, Calif.), pET15 (Novagen, Madison, Wis.), pGEX (Phannacia Biotech, Piscataway, N.J.), pEGFP-N2 (Clontech, Palo Alto, Calif.), pETL (BlueBacII; Invitrogen), pDSR-alpha (PCT Publication No. WO 90/14364) and pFastBacDual (Gibco/BRL, Grand Island, N.Y.).

Additional suitable vectors include, but are not limited to cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogeni, Carlsbad, Calif.), and mammalian , yeast or virus vectors such as a baculovirus expression system (pBacPAK plasmid derivatives, Clontech, Palo Alto, Calif.).

The recombinant molecules can be introduced into host cells via transformation, transfection, infection, electroporation, or other known techniques.

After the vector has been constructed and a nucleic acid molecule encoding an tmst2-receptor polypeptide has been inserted into the proper site of the vector, the completed vector may be inserted into a suitable host cell for amplification and/or polypeptide expression.

Host cells may be prokaryotic host cells (such as E. coli) or eukaryotic host cells (such as a yeast cell, an insect cell, or a vertebrate cell). The host cell, when cultured under appropriate conditions, synthesizes an tmst2-receptor polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity, such as glycosylation or phosphorylation, and case of folding into a biologically active molecule.

Yeast and mammalian cells are preferred hosts of the present invention. The use of such hosts provides substantial advantages in that they can also carry out post-translational peptide modifications including glycosylation. A number of recombinant DNA strategies exist which utilize strong promoter sequences and high copy number of plasmids which can be utilized for production of the desired proteins in these hosts.

Yeast recognize leader sequences on cloned mammalian gene products and secrete peptides bearing leader sequences (i.e., pre-peptides). Mammalian cells provide post-translational modifications to protein molecules including correct folding or glycosylation at correct sites.

Mammalian cells which may be useful as hosts include cells of fibroblast origin such as VERO or CtO-K1, and their derivatives. For a mammalian host, several possible vector systems are available for the expression of the desired tmst2-receptor protein. A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Useful signals are regulatory signals which are temperature-senisitive so that by varying the temperature, expression can be repressed or initiated, or are subject to chemical regulation, e.g., metabolite.

As widely known, translation of eukaryotic mRNA is initiated at the codon which encodes the first methionine. For this reason, it is preferable to ensure that the linkage between a eukaryotic promoter and a DNA sequence which encodes the desired receptor molecule does not contain any intervening codons which are capable of encoding a methionine (i.e., AUG). The presence of such codons results either in the formation to a fusion protein (if the AUG codon is in the same reading frame as the desired receptor molecule encoding DNA sequence) or a frame-shift mutation (if the AUG codon is not in the same reading frame as the desired tmst2-receptor protein encoding sequence).

The expression of the tmst2-receptor proteins can also be accomplished in procaiyotic cells. Preferred prokaryotic hosts include bacteria such as *E. coli*, Bacillus, Streptomyces, Pseudoinonas, Salmonella, SetTatia etc. The most preferred prokaryotic host is *E. coli*. Bacterial hosts of particular interest include *E. coli* K12 strain 294 (ATCC 31446), *E. coli* X1776 (ATCC 31537), *E. coli* W3110 (F$^-$, lambda$^-$, prototrophic (ATCC 27325)), and other enterobacteria (such as *Salmonella typhimurium* or *Serratia mcarcescens*), and various Pseudomonas species. The prokaryotic host must be compatible with the replicon and control sequences in the expression plasmid.

To express the desired tmst2-receptor protein in a prokaryotic cell (such as, for example, *E. coli, B. stibtilis*, Pseudomonias. Streptomyces, etc.), it is necessary to operably link the desired receptor molecule encoding sequence to a functional prokaryotic promoter. Such promoters may be either constitutive or, more preferably, regulatable (i.e., inducible or derepressible). Examples of constitutive promoters include the int promoter of bacteriophage λ, and the bla promoter of the β-lactamase gene of pBR322, etc. Examples of inducible prokaryotic promoters include the major right and left promoters, of bacteriophage λ ($P_L$ and $P_R$), the trp, recA, lacZ, lacI, gal, and tac promoters of *E. coli*, the α-amylase (Ulmanen et al., *J. Bacteriol.* 162:176–182 (1985)), the α-28-specific promoters of *B. subtilis* (Gilman et al., *Gene* 32:11–20 (1984)), the promoters of the bacteriophages of Bacillus (Gryczan, In: *The Molecular Biology of the Bacilli*, Academic Press, Inc., New York (1982)), and Streptomyces promoters (Ward et al., *Mol. Gen. Genet.* 203:468–478 (1986)). Prokaryotic promoters are reviewed by Glick, B. R., (*J. Ind. Microbiol.* 1:277–282 (1987); Cenatiempo, Y. *Biochimie* 68:505–516 (1986)); and Gottesman, S. *Ann. Rev. Genet.* 18:415–442 (1984).

Proper expression in a prokaryotic cell also requires the presence of a ribosome binding site upstream from the gene-encoding sequence. Such ribosome binding sites are disclosed, for example, by Gold, L., et al. (*Ann. Rev. Microbiol.* 35:365–404 (1981)).

The desired tmst2-receptor polypeptide encoding sequence and an operably linked promoter may be introduced into a recipient prokaryotic or eukaryotic cell either as a non-replicating DNA (or RNA) molecule, which may either be linear or, more preferably, a closed covalent circular molecule. Since such molecules are incapable of autonomous replicaitioni, the expression of the desired receptor molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. TIhe marker may complement an auxotrophy in the host (such as leu21, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include, for e.g. the case with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can also be utilized. Examples of such expression vectors include the yeast 2-micron circle, the expression plasmids YEP13, YVP and YRP, etc., or their derivatives. Such plasmids are well known in the art (Botstein et al., *Miami Wntr. Symp.* 19:265–274 (1982); Broach, J. R., In: *The Molecular Biology of the Yeast Saccharotiyces: Lift Cycle and Inheritance*, Cold Spring Harbor Laboratory, Cold Spring Harbor, N.Y., p.445–470 (1981); Broach, *Cell* 28:203–204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper or the like. The selectable marker gcne can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, *Mol. Cell. Biol.* 3:280 (1983), and others. Preferred eukaryotic vectors include PWLNEO, PSV2CAT, POG44, PXT1, pSG, pSVK3, pBPV, pMSG, pSVL (Pharmacia).

Preferred prokaryotic vectors include plasmids such as those capable of replication in *E. coli* such as, for example, pBR322, ColE1, pSC101, pACYC 184, πVX, pQE70, pQE60, pQE9, pBG, pD10, Phage script, psix174, pbmescript SK, pbsks, pNH8A, pNHIBa, pNH18A, pNH46A (SL rare gone), ptrc99a, pKK223-3, pKK233-3, pDR540, pRIT5. Such plasmids are, for example, disclosed by Maniatis, r., et al. (In: *Molecular Cloning, A Laboratorv Manual*, Cold Spring Harbor Press, Cold Spring Harbor, (N.Y. 1982)). Bacillus plasmids include pC194, pC221, pT127, etc. Such plasmids are disclosed by Gryczan, T. (In: *The Molecular Biology of the Bacilli*, Academic Press, (New York 1982), pp. 307–329). Suitable Streptomyces plasmids include pISJ101 (Kendall et al., *J Bacteriol* 169:4177–4183 (1987)), and Streptomyces bacteriophages such as φC31 (Chater et al., In: *Sixyth International Symposium on Actinotmycetales Biology*. Akademiai Kaido, Budapest, Hungary (1986), pp 45–541). Pseudomonas plasmids are reviewed by John et al. (*Rev. Infect. Dis.* 8:693–704 (1986), and Izaki (Jpn. *J. Bacteriol.* 33:729–742 (1978)). However, any other plasmid or vector may be used as long as they are replicable and viable in the host cell.

Once the vector or DNA sequence containing the constructs has been prepared for expression, the DNA constructs may be introduced into an appropriate host. Various techniques may be employed, such as a protoplast fusion, calcium phosphate precipitation, electroporation or other conventional techniques. After the fusion, the cells are grown in media and screened for appropriate activities. Expression of the sequence results in the production othfie tmst2 receptor protein.

Suitable host cells or cell lines may be mammalian cells, such as Chinese hamster ovary cells (CHO; ATCC No. CCL-61), human embryonic kidney (HEK), 293 or 293T cells (ATCC No. CRL-1573), 3T3 cells (ATCC No. CCL-92) mouse neuroblastoma N2A cells (ATCC No. CCL 131), HeLa (ATCC No. CCL-2), mouse L-929 cells (ATCC No. CCL-1), BHK (ATCC No. CCL-10) or HaK (ATCC No. CCL-15) hamster cell lines. The selection of suitable mammalian host cells and methods for transformation, culture, amplification, screening and product production and purification are known in the art. Other suitable mammalian cell lines, are the monkey COS-1 (ATCC No. 1650) and COS-7 (ATCC No. CRL-1651) cell lines, and the CV-1 cell line (ATCC No. CCL-70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene.

Similarly useful as host cells suitable for the present invention are bacterial cells. For example, the various strains of *E. coli* (e.g., HB101 (ATCC No. 33694), DH5α, DH10, and MC1061(ATCC No. 53338)) are well-known as host cells in the field of biotechnology. Various strains of *B. subtilis*, Pseudomonas spp., other Bacillus spp., Streptomyces spp., and the like may also be employed in this method.

Many strains of yeast cells known to those skilled in the art are also available as host cells for expression of the polypeptides of the present invention (e.g. Sacclharomyces, Pichia, Candida, Hansenula, and Torulopsis). (Bitter, G. , *Heterologous Gene Expression in Yeast* in. Berger, S. L. and Kimmel, A. R., 152:673–684, (1987)). Preferred yeast strains include, for example, *Saccharomyces cerevisiae*, which can be transformed readily with DNA either by preparation of spheroplasts or by treatment with alkaline salts such as LiCl. (Itoh, I. et al. J. Bacteriol. 153:163 (1983)). Some proteins expressed in yeast cells are efficiently secreted into the culture medium while others accumulate intracellularly.

Additionally, where desired, insect cell systems may be utilized in the methods of the present invention. Such systems are described for example in Kitts et al. (*Biotechniques*, 14:810–817 (1993)), Lucklow (*Curr. Opin. Biotechiol.*, 4:564–572 (1993)) and Lucklow et al. (*J. Virol.*, 67:4566–4579 (1993)). Preferred insect cells are Sf-9 and Hi5 cells (Invitrogen, Carlsbad, Calif.). Baculovirus vectors based on the *Autographa california* nuclear polyhedrosis virus, which are useful for the introduction of genetic information into insect cells include, but are not limited to pVL1392 or 1393 (Invitrogen).

Transformation or transfection of an expression vector for a tmst2-receptor polypeptide into a selected host cell may be accomplished by methods such as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

One may also use transgenic animals to express glycosylated tmst2 like polypeptides. For example, one may use a transgenic milk-producing animal (a cow or goat, lor example) and obtain the present glycosylated polypeptide in the animal milk. One may also use plants to produce tmst2-receptor polypeptides, however, in general, the glycosylation occurring in plants is different from that produced in mammalian cells, and may result in a glycosylated product which is not suitable for human therapeutic use.

Polypeptide Production

Host cells comprising an tmst2-reccptor expression vector (i.e., transformed or transfected) may be cultured using standard media well known to the skilled artisan.

The media will usually contain all nutrients to allow for the growth and survival of the cells. Suitable media for culturing *E. Coli* cells are for example, Luria Broth (LB) and/or Terrific Broth (TUB). SLutable media for culturing eukaryotic cells are Rosewell Park Memorial Institute 1640 (RPMI 1640), Minimal Essential Medium (MEM), Dulbecco's Modified Eagle Medium (DMEM), all of which may be supplemented with serum and/or growth factors as required by the particular cell line being cultured. A suitable medium for insect cultures is Grace's medium supplemented with yeastolate. lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transfonned. For example, where the selectable marker element is kanamycin resistance, the compound added to the culture medium will be kanamycin. Other compounds for selective growth include ampicillin. tetracycline and neomycin The amount of tmst2-receptor polypeptidc produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays.

If a tmst2-receptor polypeptide has been designed to be secreted from the host cells, the majority of polypeptide may be foulid in the cell culture medium. If however, the tmst2-receptor polypeptide is not secreted from the host cells, it will be present in the cytoplasm and/or the nucleus (for eukaiyotic host cells) or in the cytosol (for bacterial host cells).

For a tmst2-receptor polypeptide situated in the host cell cytoplasm and/or nucleus, (for eukaryotic host cells) or in the cytosol (for bacterial host cells), intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

Purification of a tmst2-receptor polypeptide from solution can be accomplished using a variety of tecmiques. If the polypeptidc has been synthesized such that it contains a tag such as Hexahistidine (tmst2-receptor polypeptide/hexaHis) or other small peptide such as FLAG (Eastman Kodak Co., New Haven, Conn.) or myc (Invitrogen, Carlsbad, Calif.) or the IgG Fc fragment fused at either its carboxyl or amino terminus, it may essentially be purified in a one-step process by passing the solution through an affinity column where the column matrix has a high affinity for the tag or for the polypeptide directly (i.e., a monoclonal antibody specifically recognizing tmst2-receptor polypeptide). For example, polyhistidine binds with great affinity and specificity to nickel, thus an affinity column of nickel (such as the QIAGEN® nickel columns) can be used for purification of tmst2- receptor polypeptide/polyHis. (See for example, Ausubel et al. eds., *Current Protocols in Molecular Biology*, Section 10.11.8, John Wiley & Sons, New York (1993)).

Where a tmst2-receptor polypeptide is prepared without a tag attached, and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machinc/technique, Hoefer Scientific). In some cases, two or more of these techniques may be combined to achieve increased purity.

If a tmst2-receptor polypeptide is produced intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a tmst2-receptor polypeptide has formed inclusion bodies in the cytosol, the inclusion bodies can often bind to the inner and/or outer cellular membranes and thus will be found primarily in the pellet material after centrifugation. The pellet material can then be treated at pH extremes or with chaotropic agent such as a detergent, guanidine, guanidinie derivatives, urea, or urea derivatives in the presence of a reducing agent such as dithiothreitol at alkaline pH or tris carboxyethyl phosphine at acid pH to release, break apart, and solubilize the inclusion bodies. The tmst2-receptor polypeptide in its now soluble form can then be analyzed using gel electrophoresis, immunoprecipitation or the like. If it is desired to isolate the tmst2-receptor polypeptide, isolation may be accomplished using standard methods described herein below and in Marston et al. (*Meth. Enz.*, 182:264–275(1990)).

In some cases, a tmst2-receptor polypeptide may not be biologically active upon isolation. Various methods for "refolding" or converting the polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotope is used at a lower concentration and is not necessarily the same chaotropes as used for the Solubilizationi. In most cases the refolding/oxidatioln solution will also contain a reducing agent or the reducing agent plus its' oxidized form in a specific ratio to generate a particular redox potential allowing for disulfide shufflin(g to occur in the formation of the protein's cysteine bridge(s). Some of the commonly used redox couples include cysteine/cystamine, gilutathione (GSH)/dithiobis GSH, cupric chloride, ditliothreitol(DTT)/ditlianie DTT, 2-mercaptoethanol($\beta$ME)/dithio-$\beta$(ME). A cosolvent may be used to increase the efficiency of the refolding and the more common reagents used for this purpose include glycerol, polyethylene glycol of various molecular weights, arginine and the like.

If inclusion bodies are not formed to a significant degree upon expression of a tmst2-receptor polypeptide, then the polypeptide will be found primarily in the supernatant after centrifugation of the cell homogenate. The polypeptide may be further isolated from the supernatant using methods such as those described herein.

Additionally, the tmst2-receptor polypeptide may be purified through the use of a monoclonal antibody which is capable of specifically recognizing and binding to the tmst2-receptor polypeptide.

Suitable procedures for purification thus include, without limitation, affinity chromatography, immunoaffinity chromatography, ion exchange chromatography, molecular sieve chromatography, High Performance Liquid Chromatography (HPLC), electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

Tmst2-receptor polypeptides, fragments, and/or derivatives thereof may also be prepared by chemical synthesis methods (such as solid phase peptide synthesis) using techniques known in the art such as those set forth by Merrifield et al., (*J. Am. Chem. Soc.*, 85:2149 (1963)), Houghten et al. (*Proc Natl Acat. Sci. USA*, 82:5132 (1985)), and Stewart and Young (*Solid Phase Peptide Sythesis*, Pierce Chemical Co., Rockford, Ill. (1984)). Such polypeptidcs may be synthesized with or without a methionine on the amino terminus. Chemically synthesized tmst2-receptor polypeptides or fragments may be oxidized using methods set forth in these references to form disulfide bridges. Chemically synthesized tmst2-receptor polypeptides, fragments or derivatives are expected to have comparable biological activity to the corresponding tmst2-receptor polypeptides, fragments or derivatives produced recombinanitly or purified from natural sources, and thus may be used interchangeably with recombinant or natural tmst2-receptor polypeptide.

Another means of obtaining tmst2-receptor polypeptide is via purification from biological samples such as source tissues and/or fluids in which the tmst2-receptor polypeptide is naturally found. Such purification can be conducted using methods for. protein purification as described herein. The presence of the tmst2-receptor polypeptide during purification may be monitored using, for example, an antibody prepared against recombinantly produced tmst2-receptor polypeptide or peptide fragments thereof.

A number of additional methods for producing nucleic acids and polypeptides are known in the art, and can be used to produce polypeptides having specificity for tmst2 like. See for example, Roberts et al., *Proc. Natl. Acad. Sci. U.S.A.*, 94:12297–12303 (1997), which describes the production of fusion proteins between an mRNA and its encoded peptide. See also Roberts, *Curr. Opin. Chem. Biol.*, 3:268–273 (1999). Additionally, U.S. Pat. No. 5,824,469 describes methods of obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those which exhibit a predetermined biological function. From that subpopulation, oligonucleotides capable of carrying out the desired biological function are isolated.

U.S. Pat. Nos. 5,763,192, 5,814,476, 5,723,323, and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive IL-17 like protein expression libraries, which can subsequently be used for high throughput phenotypic screening in a variety of assays, such as biochemical assays, cellular assays, and whole organism assays (e.g., plant, mouse, etc.).

Proteins, Polypeptides, Fragments, Variants and Muteins of tmst2:

Polypeptides of the invention include isolated tmst2-receptor polypeptides and polypeptides related thereto including fragments, variants, fusion polypeptides, and derivatives as defined herein above.

Tmst2-receptor fragments of the invention may result from truncations at the amino terminus (with or without a leader sequence), truncations at the carboxy terminus, and/or deletions internal to the polypeptide. Most deletions and insertions, and substitutions in particular, are not expected to produce radical changes in the characteristics of the tmst2-receptor protein. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the tmst2-receptor polypeptide-encoding nucleic acid, expression of the variant nucleic acid in recombinant cell culture, and, optionally, purification from the cell culture, for example, by immunoaffinity adsorption on a polyclonal anti tmst2-receptor antibody column (to absorb the variant by binding it to at least one remaining immune epitope). In preferred embodiments, truncations and/or deletions comprise about 10 amino acids, or about 20 amino acid, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 175 amino acids or 190 amino acids.

Tmst2-receptor polypeptide variants of the invention include one or more amino acid substitutions, additions and/or deletions as compared to SEQ ID NO: 8. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, as defined above, or non-conservative or any combination thereof. More particularly tmst2-receptor variants may comprise the amino acid sequence set out as SEQ ID NO: 8, wherein one or more amino acids from the group consisting of amino acids 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, and 198 is substituted with another amino acid.

Tmst2-receptor-receptor variants may also comprise the amino acid sequence set out as SEQ ID NO.: 8, wherein one or more amino acids from the group consisting of amino acids 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40,41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 14, 75, 76, 77, 78, 79, 80, 81, 82, 83, 84, 85, 86, 87, 88, 89, 90, 91, 92, 93, 94, 95, 96, 97, 98, 99, 100,101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, and 198 is/are deleted, Receptor variants of the secreted form of the tmst-2 receptor (tmst2) are also envisioned within the scope of the invention. Variants of the secreted form of the tmst2-receptor may comprise the amino acid sequence set out as SEQ ID NO: 10, wherein one or more amino acids from the group consisting of amino acids 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, and 180 is/are substituted with another amino acid.

Soluble tmst2-receptor variants may also comprise the amino acid sequence set out as SEQ ID NO: 10, wherein one or more amino acids from the group consisting of amino acids 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 151, 152, 153, 154, 155, 156, 157, 158, 159, 160, 161, 162, 163, 164, 165, 166, 167, 168, 169, 170, 171, 172, 173, 174, 175, 176, 177, 178, 179, and 180 is/are deleted, The variants may also lhave additions of amino acid residues either at the carboxy terminus or at the amino terminus (with or without a leader sequence).

Preferred tmst2-rcccptor polypeptide variants include glycosylation variants wherein the number and/oor type of glycosylation sites has been altered compared to native tmst2-receptor polypeptide. In one embodiment, tmst2-receptor variants comprise a greater or a lesser number of N-linked glycosylation sites. An N-linked glycosylation site is characterized by the sequence: Asn-X-Ser or Thr, where the amino acid residue designated as X may be any type of amino acid except proline. Substitution(s) of amino acid residues to create this sequence provides a potential new site for addition of an N-liniked carbohydrate chain. Alternatively, substitutions to eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

One skilled in the art will be able to determine suitable variants ofthe native tmst2-receptor polypeptide using well known techniques. For example, one may be able to predict suitable areas ofthe molecule that may be changed without destroying biological activity. Also, one skilled in the art will realize that even areas that may be important for biological activity or for stnIcture may be subject to conservative amino acid substitutions without destroying the biological activity or without adversely affecting the polypeptide structure.

For predicting suitable areas of the molecule that may be changed without destroying activity, one skilled in the art may target areas not believed to be important for activity. For example, when similar polypeptides with similar activities from the same species or from other species are known, one skilled in the art may compare the amino acid sequence of tmst2-receptor polypeptide to such similar polypeptides. After making such a comparison, one skilled in the art would be able to determine residues and portions of the molecules that are conserved among similar polypeptides. One skilled in the art would know that changes in areas of the tmst2-receptor molecule that are not conserved would be less likely to adversely affect biological activity and/or stricture. One skilled in the art would also know that, even in relatively conserved regions, one could have likely substituted chemically similar amino acids for the naturally occurring residues while retaining activity (e.g. conservative amino acid residue substitutions).

Also, one skilled in the art may review strmcture-function studies identifying residues in similar polypeptides that are important for activity or structure. In view of such a comparison, one skilled in the art can predict the importance of amino acid residues in tmst2-receptor that correspond to amino acid residues that are important for activity or structure in similar polypeptides. One skilled in the art may opt for chemically similar amino acid substitutions for such predicted important amino acid residues of tmst2-receptor.

If available, one skilled in the art can also analyze the crystal structure and amino acid sequence in relation to that structure in similar polypeptides. In view of that infonnation, one skilled in the art may be able to-predict the alignment of amino acid residues of tmst2-receptor polypeptide with respect to its three dimensional structure. One skilled in the art may choose not to make radical changes to amino acid residues. predicted to be on the surface of the protein, since such residues may be involved in important interactions with other molecules.

Moreover, one skilled in the art could generate test variants containing a single amino acid substitution at each amino acid residue. The variants could be screened using activity assays disclosed in this application. Such variants could be used to gather information about suitable variants. For example, if one discovered that a change to a particular amino acid residue resulted in destroyed activity, variants with such a change would be avoided. In other words, based on information gathered from such experiments, when attempting to find additional acceptable variants, one skilled in the art would have known the amino acids where further substitutions should be avoided either alone or in combination with other mutations.

Tmst2-receptor fusion polypeptides of the invention comprise tmst2-receptor polypeptides, fragments, variants, or derivatives fused to a heterologous peptide(s) or protein(s). Heterologous peptide(s) and protein(s) include, but are not limited to, an epitope to allow for detection and/or isolation of a tmst2-receptor fusion polypeptide, a transmembrane receptor protein or a portion thereof, such as an extracellular domain, or a transmembrane, a ligand or a portion thereof which binds to a transmembrane receptor protein, an enzyme or portion thereof which is catalytically active, a protein or peptide which promotes oligomerization, such as leucine zipper domain, and a protein or peptide which increase stability, such as an immunoglobulin constant region. A tmst2-receptor polypeptide may be fused to itself or to a fragment, variant. or derivative thereof. Fusions may be made either at the amino terminus or at the carboxy terminus of a tmst2-receptor polypeptide, and may be direct with no linker or adapter molecule or may be through a linker or adapter molecule. such as one or more amino acid residues up to about 20 amino acids residues, or up to about 50 amino acid residues. Altcnatively, the tmst2-receptor fusion protein may comprise one or two tmst2-receptor polypeptides covalently linked to one or two TNF-receptor polypeptide(s), or a member of the TNF-receptor family or a cytokinc receptor such as interleukin-1 R (IL-1R) polypeptide. The receptors preferably are produced as fusion proteins using recombinant DNA technology. A linker or adapter molecule may also be designed with a cleavage site for a DNA restriction endonuclease or for proteolytic cleavage to allow for separation and subsequent folding of the fuised moieties.

Also envisioned as a part of the invention are circularly permuted structural analogs of the tmst2-receptor polypeptide.

The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., *Proc. Natl. Acad. Sci. U.S.A.* 76:3218–3222, (1979); Teather & Erfle, *J. Bacteriol.* 172:3837–3841, (1990); Schimming et al., *Eur. J. Biochlem.* 204:13–19, (1992); Yamiuchi and Minamikawa, *FEBS Lett* 260:127–1 30, (1991); MacGregor et al., *FEBS Lett.* 378:263–266, (1996)). The first in vitro application of this type of rearrangement to proteins was described by Goldenberg and Creighton (*J. Mol. Biol.* 165:407–413, (1983)). A new N-temiinus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus, and the new sequence continues with the same sequence as the original until it reaches a point that is at or near the amino acid that was N-terminal to the breakpoint site of the original sequence, this residue forming the new C-terminus of the chain.

This approach has been applied to proteins which range in size from 58 to 462 amino acids (Goldenberg & Creighton, *J. Mol. Biol.* 165:407–413, (19830; Li & Coffino, *Mol. Cell. Biol.* 13:2377–2383, (1993)). The proteins examined have represented a broad range of structural classes, including proteins that contain predominantly a α-helix (interleukin-4; Kreitman et al., *Cytokine* 7:311–318, (1995)), β-sheet (interieukin-1; Horlick et al., *Protein Eng.* 5:427–431, (1992)), or mixtures of the two (yeast phosphoribosyl anthranilate isomerase; Luger et al., *Science* 243:206–210, (1989)).

In a preferred embodiment, a tmst2-receptor polypeptide, fragment, variant and/or derivative is fused to an Fc region of human IgG. In one example, a human IgG hinge, CH2 and CH3 region may be fused at either the N-teniinus or C-terminus of the tmst2-reccptor polypeptides using methods known to the skilled artisan. In another example, a portion of a hinge regions and CH2 and CH3 regions may be fuse. The tmst2-receptor Fc -fusion polypeptide so produce may be purified by use of a Protein A affinity column (Pierce, Rockford, Ill.). In addition, peptide and proteins fused to an Fc region have been found to exhibit a substantially greater half-life in vivo than the unfused counterpart. Also, a fusion to an Fc region allows for dimerization/multimerization of the fusion polypeptide. The Fc region may be naturally occurring Fc region, or may be altered to improve certain qualities such as therapeutic qualities, circulation time, reduce aggregation, etc.

Tmst2-receptor-receptor polypeptide derivatives are also included in the scope of the present invention. Covalent modifications of the tmst2-receptor proteins of the present invention are included within the scope of this invention. Variant tmst2-receptor proteins maybe conveniently prepared by in vitto synthesis. Such modifications may be introduced into the molecule by reacting targeted amino acid residues of the purified or crzde protein with an organic derivatizing agent that is capable of reacting with selected side chains or terminal residues. The resulting covalent derivatives are useful in programs directed at identifying residues important for biological activity.

Cysteinyl residues most commonly are reacted with α-haloacetates (and corresponding amines), Such as chloroacetic acid or chloroacetamide, to give carboxyiethyl or carbocyamidomiiethyl derivatives. Cysteinyl residues also are derivatized by reaction with bromotri fLuoroacetonie, α-bromo-β(5-imidozoyl)propionic acid, chloroacetyl phosphate, N-alkylmalcimides, 3-nitro-2-pyridyl disulfide, methyl 2-pyridyl disulfide, p-chloromercuribenzoate, 2-chloromercuri-4-nitrophenol, orchloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine Epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides ($R^1$) such as 1-cyclohexyl-3-(2-morpholinyl-(4-ethyl) carbodiimide or 1-ethyl-3 (4 azonia 4,4-dimethylpenityl) carbodiimide. Furthermore, aspartyl and glutamyl residues are converted to asparaginyl and glutaminyl residues by reaction with ammonium ions.

Derivatization with bifunctional agents is useful for crosslinking the "tmst2-receptor proteins" to water-insoluble support matrixes or surfaces for use in the method for cleaving the tmst2-receptor protein-fusion polypeptide to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctionial imidoesters, including disuccinimidyl esters such as 3,3'-dithiiobis(succinimidylpropioonate), and bifunctional maleimnides such as bis-N-maleimido-1,8-octane. Derivatizing agents such as methyl-3-[p-azidophenyl)dithio]propioimidate yield photoactivatable intermediates that are capable of forming cross links in the presence of light. Altenatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440, incorporated herein by reference, are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, *Proteins: Structure find Molecule Properties*, W. H. Freeman & Co., San Francisco, pp. 79–86 (1983)), acetylation of the N-terminal amine, and, in some instances, amidation of the C-terminal carboxyl groups. Such derivatives are chemically modified tmst2-receptor polypeptide compositions in which tmst2-receptor polypeptide is linked to a polymer. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. Fhe polymer may be of any molecular weight, and may be branched or unbranched. Icluided within the scope of the tmst2-receptor polypeptide polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

For the acylation reactions, the polymer(s) selected should have a single reactive ester group. For reductive alkylation, the polymer(s) selected should have a single reactive aldehyde group. A preferred reactive aldehyde is polyethylene glycol propionaldehyde, which is water stable, or mono C1–C10 alkoxy or aryloxy derivatives thereof (see U.S. Pat. No. 5,252,714).

Pegylation of tmst2-receptor polypeptides may be carried out by any of the pegylation reactions known in the art, as described for example in the following references: *Focus on Growth Factors* 3: 4–10 (1992); EP 0 154 316; and EP 0 401 384 incorporated herein by reference. Preferably, the pegylation is carried out via an acylation reaction or an alkylation reaction with a reactive polyethylene glycol molecule (or an analogous reactive water-soluble polymer) as described below.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophibic nature, thus creating a water shell or hydration sphere when attached to other proteins or polymer surfaces. PEG is nontoxic, non-immunogenic, and approved by the Food and Drug Administration for internal consumption.

Proteins or enzymes when conjugated to PEG have demonstrated bioactivity, non-anttigenic properties, and decreased clearance rates when administered in animals. F. M. Veronese et al., *Preparation and Properties of Monomethoxypoly(ethyene glyco.)-modified Enzymes for Theraeutic Applications*, in J. M. Harris ed., *Poly(Ethylene Clycol) Chemistry—Biotechnical and Biomedical Applications* 127–36 (1 992), incorporated herein by reference. This is due to the exclusion properties of PEG in preventing recognition by the immune system. In addition, PEG has been widely used in surface modification procedures to decrease protein adsorption and improve blood compatibility. Kim et al., *Ann. N. Y. Acad. Sci.* 516:116–30 (1987); Jacobs et al., *Artif. Organs* 12:500–01 (1988); Park et al.,*J. Poly. Sci*, Part A 29:1725–31 (1991), incorporated herein by reference. Hydrophobic polymer surfaces, such as polyurethanes and polystyrene were modified by the grafting of PEG (MW 3,400) and employed as nonthrombogenic surfaces. In these studies, surface properties (contact angle) were more consistent with hydrophilic surfaces. due to the hydrating effect of PEG. More importantly, protein (albumin and other plasma proteins) adsorption was greatly reduced, resulting from the high chain motility, hydration sphere, and protein exclusion properties of PEG.

PEG (MW 3,4000) was determined as an optimal size in surface immobilization studies, Park et al., *J. Biomed. Mat. Res*. 26:739–45 (1992), while PEG (MW 5,000) was most beneficial in decreasing protein antigenicity. (Veronese et al., In Harris el al., *Poly(Ethylene Glycol) Chemistry— Biotechnical and Biotechnical Applications* 127–36, supra., incorporated herein by reference)

In general, chemical derivatization may be performed under any suitable conditions used to react a biologically active substance with an activated polymer molecule. Methods for preparing pegylated tmst2-receptor polypeptides will generally comprise the steps of (a) reacting the polypeptide with polyethylene glycol (such as a reactive ester or aldehyde derivative of PEG) under conditions whereby tmst2-receptor polypeptide becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

In a preferred embodiment, the tmst2-receptor polypeptide derivative will have a single PEG moiety at the N terminus. See U.S. Pat. No. 8,234,784, herein incorporated by reference.

In another embodiment, tmst2-receptor polypeptides may be chemically coupled to biotin, and the biotin/tmst2 like polypeptide molecules which are cotjugatedc are then allowed to bind to avidin, resulting in tetravalent avidinibiotin/tmst2 like polypeptide molecules. Tmst2 like polypeptides may also be covalently coupled to dinitrophenol (DNP) or trinitropheniol (TNP) and the resulting conjugates precipitated with anti-DNP or anti-TNP-IgM to form decameric conjugates with a valency of 10.

Generally, conditions which may be alleviated or modulated by administration of the present tmst2-receptor polypeptide derivative include those described herein for tmst2-receptor polypeptides. However, the tmst2-receptor polypeptide derivative disclosed herein may have additional activities, enhanced or reduced biological activity, or other characteristics, such as increased or decreased half-life, as compared to the non-derivatized molecules.

Selective Binding Agents

As used herein, the term "selective binding agent" refers to a molecule which has specificity for one or more tmst2-receptor polypeptides. Suitable selective binding agents include, but are not limited to, antibodies and derivatives thereof, polypeptides, antisense oligonucleotides, and small molecules. Suitable selective binding agents may be prepared using methods known in the art. An exemplary tmst2-receptor polypeptide selective binding agent of the present invention is capable of binding a certain portion of the tmst2 like polypeptide thereby inhibiting the binding of the polypeptide to the tmst2 like polypeptide receptor(s).

Selective binding agents such as antibodies and antibody fragments that bind tmst2-receptor polypeptides are within the scope of the present invention. The antibodies may be polyclonal including monospecific polyclonal, monoclonal (MAbs), recombinant, chimeric, humanized such as CDR-, rafted, human, single chain, and/or bispecific, as well as fragments, variants or derivatives thereof. Antibody fragments include those portions of the antibody which bind to an epitope on the tmst2 like polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a tmst2-receptor polypeptide generally are produced in animals (e.g., rabbits or mice) by means of multiple subcutaneous or intraperitoneal injections of tmst2-receptor and an adjuvant. It may be useful to conjugate a tmst2-receptor polypeptide, or a variant, fragment or derivative thereof to a carrier protein that is immunogenic in the species to be immrunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-tmst2-receptor antibody titer.

Monoclonal antibodies directed toward tmst2-receptor polypeptides are produced using any method which provides for the production of antibody molecules by continuous cell lines in culture. Examples of suitable methods for preparing monoclonal antibodies include the hybridoma methods of Kohler, et al., *Nature*, 256: 495–497 (1975), and the human B-cell hybridoma method, Kozbor, *J. Immunol.*, 133: 3001 (1984); Brodeur, et al., *Monoclonal Atitibody Production Techniques and Applications*, pp. 51–63 (Marcel Dekker, Inc., New York, 1987).

Also provided by the invention are hybridoma cell lines which produce monoclonal antibodies reactive with tmst2-receptor polypeptides.

Monoclonal antibodies of the invention may be modified for use as therapeutics. One embodiment is a "chimeric" antibody in which a portion of the heavy and/or light chain is identical with or homologous to corresponding sequence in antibodies derived from a particular species or belonging to a particular antibody class or subclass, while the remainder of the chain(s) is identical with or homologous to corresponding sequence in antibodies derived from another species or belonging to another antibody class or subclass. As included are fragments of such antibodies, so long as they exhibit the desired biological activity (see U.S. Pat. No. 4,816,567; Morrison, et al., *Proc. Natl. Acad. Sci. U.S.A.* 81,6851–6855 (1985)).

In another embodiment, a monoclonal antibody of the invention is a "humanized" antibody. Methods for humanizing non-human antibodies are well known in the art. Generally, a humanized antibody has one or more amino acid residues introduced into it from a source which is non-human. Humanization can be performed following methods known in the art (Jones et al., *Nature*, 321: 522–525 (1986); Riechmann, et al., *Nature*, 332: 323–327 (1988); Verhoeyen et al., *Science*, 239: 1534–1536 (1988)), by substituting rodent complementarity-determiniing regions (CDRs) for the corresponding regions of a human antibody.

Also encompassed by the invention are fully human antibodies which bind tmst2-receptor polypeptides, fragments, variants and/or derivatives. Using transgenic animals (e.g., mice) that are capable of producing a repertoire of human antibodies in the absence of endogenous immunoglobulin production such antibodies are produced by immunizing with a tmst2-receptor antigen (i.e., having at least 6 contiguous amino acids), optionally conjugated to a carrier. See, for example, Jakobovits et al., *Proc. Natl. Acid. Sci. U.S.A.*, 90: 2551–2555 (1993); Jakobovits et al., *Nature*, 362: 255–258 (1993); Bruggermann et al., *Year in Immuno.*, 7:33 (1993). In one method, such transgenic animals are produced by incapacitating the endogenous loci encoding the heavy and light immtnoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human (rather than e.g., murine) amino acid sequences, including variable regions which are immunospecific for these antigens. Sec PCT Application Nos. PCT/US96/05928 and PCT/US93/06926. Additional methods are described in U.S. Pat. No. 5,545,807, PCT application Nos. PCT/US91/245, PCT/GB89/01207, and in EP 546073B1 and EP 546073A1. Human antibodies may also be produced by the expression of recombinant DNA in host cells or by expression in hybridoma cells as described herein.

In an alternate embodiment, human antibodies can also be produced in phage-display libraries (Hoogenboom, el al., *J. Mol.* 1 Biol. 227:381 (1991); Marks, el al., *J. Mol. Biol.* 222:581 (1991). These processes mimic immune selection through the display of antibody repertoires on the surface of filamentous bacteriophage, and subsequent selection of phage by their binding to an antigen of choice. One such technique is described in PCT Application No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials. and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

For diagnostic applications, anti-tmst2-receptor antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, β-galactosidase or horseradish peroxidase. Bayer et al., *Meth. Enz.*, 184: 138–163 (1990).

The anti-tmst2-receptor antibodies of the invention may be employed in any known assay method, such as competitive binding assays, direct and indirect sandwich assays, and immunoprecipitation assays (Sola, *Monoclonal Antibodies: A Manual of Techniques*, pp. 147–158 (CRC Press, Inc., 1987)) for the detection and quantitation of tmst2-receptor polypeptides. The antibodies will bind tmst2-receptor polypeptides with an affinity which is appropriate for the assay method being employed.

The activity of the cell lysate or puri Fied tmst2 receptor protein variant is then screened in a suitable screening assay for the desired characteristic. For example, a change in the binding affinity for a ligand or immunological character of the tmst2 receptor protein, such as affinity for a given antibody, is measured by a competitive type immunoassay. Changes in immuomodulation activity are measured by the appropriate assay. Modifications of such protein properties as redox or thermal stability hydrophobicity, susceptibility to proteolytic degradation or the tendency to aggregate with carriers or into multimers are assayed by methods well known to the ordinarily skilled artisan. Competitive binding assays rely on the ability of a labeled standard (e.g., a tmst2-receptor polypeptide, or an immunologically reactive portion thereof) to compete with the test sample analyte (a tmst2-receptor polypeptide) for binding with a limited amount of antibody. The amount of a tmst2-receptor polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich imuno-assay typically involve the use of two antibodies, each capable of binding to a different immunogenic portion, or epitope, of the protein to be detected and/or quantitated. In a sandwich assay, the test sample analyte is bound by a first antibody which is immobilized on a solid support, and thereafter a second antibody binds to the analyte, thus forming an insoluble three part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbant assay (ELISA), in which case the detectable moiety is an enzyme.

The anti-tmst2-receptor antibodies of the invention also are useful for in vivo imaging. An antibody labeled with a detectable moiety is administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

Selective binding agents of the invention, including anti-tmst2-receptor antibodies. may be used as therapeutics. These therapeutic antibodies are generally agonists or antagonists, in that they either enhance or reduce, respectively, at least one or the biological activities of a tmst2-receptor polypeptide. In one embodiment, antagonist antibodies of the invention are antibodies or binding fragments thereof which are capable of specifically binding to a tmst2-receptor polypeptide, fragment, variant and/or derivative, and which are capable of inhibiting or eliminating the functional activity of a tmst2-receptor polypeptide in vivo or in vitro. In preferred embodiments, an antagonist antibody will inhibit the functional activity of a tmst2-receptor polypeptide at least about 50%, preferably at least about 80%, more preferably 90%, and most preferably 100%. Agonist and antagonist anti-tmst2-receptor antibodies are identified by screening assays described below.

Tmst2-receptor polypeptides can be used to clone tmst2-receptor ligand(s) using an "expression cloning" strategy. Radiolabeled ($^{125}$-Iodine) tmst2-receptor polypeptide or "affinity/activity-tagged" tmst2-receptor like polypeptide (such as an Fc fusion or an alkaline plhosphatase fusion) can be used in binding assays to identify a cell type or a cell line or tissue that expresses tmst2-receptor ligand(s). RNA isolated from such cells or tissues can then be converted to cDNA, cloned into a mammalian expression vector, and transfected into mammalian cells (for example, COS, or 293) to create an expression library. Radiolabeled or tagged tmst2-receptor polypeptide can then be used as an affinity reagent to identify and isolate the subset of cells in this library expressing tmst2-receptor ligand(s). DNA is then isolated from these cells and transfected into mammalian cells to create a secondary expression library in which the fraction of cells expressing tmst2-receptor ligand(s) would be many-fold higher than in the original library. This enrichment process can be repeated iteratively until a single recombinant clone containing an tmst2-receptor ligand is isolated. Isolation of tmst2-receptor ligand(s) is useful for identifying or developing novel agonists and antagonists of the tmst2-receptor signaling pathway. Such agonists and antagonists include tmst2-receptor ligand(s), anti-tmst2-receptor ligand antibodies, small molecules or antisense oligonucleotides.

Diagnostic Kits and Reagents

This invention also contemplates use of tmst2-receptor proteins, fragments thereof, peptides, binding compositions, and their fusion products in a variety of diagnostic kits and methods for detecting the presence of receptors and/or antibodies, or ligands. Typically the kit will have a compartment containing a tmst2-receptor peptide or gene segment or a reagent which recognizes one or the other, e.g., binding reagents.

A kit for determining the binding affinity of a ligand or test compound to the tmst2-receptor would typically comprise a test compound; a labeled compound, for example an antibody having known binding affinity for the protein; or a source of ligand (naturally occurring or recombinant), and a means for separating bound from free labeled compound, such as a solid phase for immobilizing the ligand or receptor. Once compounds are screened, those having suitable binding affinity to the ligand or receptor can be evaluated in suitable biological assays, as are well known in the art, to determine whether they act as agonists or antagonists to the receptor. The availability of recombinant chemokine or receptor polypeptides also provide well defined standards for calibrating such assays or as positive control samples.

A preferred kit for determining the concentration of, for example, tmst2-receptor or ligand in a sample would typically comprise a labeled compound, e.g., antibody, having known binding affinity for the target, a source of ligand or receptor (naturally occurring or recombinant), and a means for separating the bound from free labeled compound, for example, a solid phase for immobilizing the ligand or receptor. Compartments containing reagents, and instructions for use or disposal, will normally be provided.

Antibodies, including antigen binding fragments, specific for the ligand or receptor, or fragments are useful in diagnostic applications to detect the presence of elevated levels of ligand, receptor, and/or its fragments. Such diagnostic assays can employ lysates, live cells, fixed cells, immunofluorescenice, cell cultures, body fluids, and further can involve the detection of antigens related to the ligand or receptor in serum, or the like. Diagnostic assays may be homogeneous (without a separation step between free reagent and antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the primary antibody to a ligand or receptor or to a particular fragment thereof. Similar assays have also been extensively discussed in the literature. (See, e.g., Harlow and Lane, *Antibodies: A Laboratory Manual*, CSH, 1988)

Anti-idiotypic antibodies may have similar uses to diagnose presence of antibodies against a chemokine or receptor, as such may be diagnostic of various abnormal states. For example, overproduction of a chemokine or receptor may result in production of various immunological reactions which may be diagnostic of abnormal physiological states, particularly in various inflammatory or asthma conditions.

Frequently, the reagents for diagnostic assays are supplied in kits, so as to optimize the sensitivity of the assay. For the subject invention, depending upon the nature of the assay, the protocol, and the label, either labeled or unlabeled antibody or labeled chemokine or receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments or containers for each useful reagent. Desirably, the reagents are provided as a dry lyophilized powder, where the reagents may be reconstituted in an aqueous medium providing appropriate concentrations of reagents for performing the assay.

The aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the ligand, test compound, receptor, or antibodies thereto can be labeled either directly or indirectly. Possibilities for direct labeling include label groups: radiolabels such as $^{125}$I, enzyines (U.S. Pat. No. 3,645,090) such as peroxidase and alkaline phosphatase, and fluorescent labels (U.S. Pat. No. 3,940, 475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating bound from the free ligand, or alternatively bound from free test compound. The chemokine or receptor can be immobilized on various matrixes, perhaps with detergents or associated lipids, followed by washing. Suitable matrixes include plastic such as an ELISA plate, filters, and beads. Methods of immobilizing the chemokine or receptor to a matrix include, without limitation, direct adhesion to plastic, use of a capture antibody, chemical coupling, and biotin-avidin. The last step in this approach may involve the precipitation of antigen/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (*Clin. Chem.*,30:1457–1461 (1984)), and the double antibody magnetic particle separation as described in U.S. Pat. No. 4,659,6178, incorporated herein by reference.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Nucleic acid molecules of the invention may be used to map the locations of the tmst2-receptor gene and related genes on chromosomes. Mapping may be done by techniques known in the art, such as PCR amplification, in situ hybridization, and FISH.

This invention is also related to the use of the tmst2-receptor gene as part of a diagnostic assay for detecting diseases or susceptibility to diseases related to the presence of mutated tmst2-receptor gene. Such diseases are related to an abnormal expression of tmst2-receptor, for example, abnonnal cellular proliferation such as tumors and cancers.

Individuals carrying mutations in the human tmst2-receptor gene may be detected at the DNA level by a variety of techniques. Nucleic acids for diagnosis may be obtained from a patient's cells, such as from blood, urine, saliva, tissue biopsy and autopsy material. The gcnomic DNA may be used directly for detection or may be amplified enzymatically by using PCR (Saiki et al., *Nature*, 324:163–166 (1986)) prior to analysis. RNA or cDNA may also be used for the same purpose. As an example, PCR primers complementary to the nucleic acid encoding tmst2-receptor polypeptide can be used to identify and analyze tmst2 receptor mutations. For example, deletions and insertions can be detected by a change in size of the amplified product in comparison to the normal genotype. Point mutations can be identified by hybridizing amplified DNA to radiolabeled tmst2 receptor RNA or alternatively radiolabeled tmst2 receptor antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays, such as RNase and S1 protection or the chemical cleavage method (e.g., Cotton et al., *PNAS, USA*, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length POLYMORPPHISMS (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of tmst2-receptor protein in various tissues since an over-expression of the proteins compared to normal control tissue samples may detect the presence of a disease or susceptibility to a disease, for example, tumors, cerebral malaria and hereditary periodic fever syndromes. Assays used to detect levels of tmst2-receptor protein in a sample derived from a host are well-known to those of skill in the art and include radioimmunoassays, competitive-binding assays, Western Blot analysis, ELISA assays and "sandwich" assay. An ELISA assay (Coligan, et al., *Current Protocols in Immunology*, 1(2), Chapter 6, (1991)) partially comprises preparing an antibody specific to the tmst2-receptor antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g., a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any tmst2-receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to tmst2-receptor. Unattached reporter antibodyis then washed out. Peroxidase substrates are then added to the dish and the amount of color developed in a given time period is a measurement of the amount of tmst2-receptor protein present in a given volume of patient sample when compared against a standard curve.

A competition assay may be employed wherein antibodies specific to tmst2 receptor are attached to a solid support and labeled tmst2-receptor and a sample derived from the host are passed over the solid support and the amount of label detected, for example, by liquid scintillation chromotagraphy, can be correlated to a quantity of tmst2 receptor in the sample. In addition, a "sandwich" immunoassay as described above may also be carried out to quantify the amount of tmst2-receptor in a biological sample.

The sequences ofthe present invention are also valuable for chromosome identification and mapping. The sequence can be specifically targeted to and can hybridize with a particular location on an individual human chromosome. Moreover, there is a current need for identifying, particular sites on the chromosome wherein a gene can be localized. Few chromosome marking reagents based on actual sequence data (repeat POLYMORPHISMS) are presently available for marking chromosomal location. The mapping of DNAs to chromosomes according to the present invention is an important first step in correlating those sequences with genes associated with disease.

Briefly, sequences can be mapped to chromosomes by preparing PCR primiers (preferably 15–25 bp) from the cDNA. Computer analysis of the 3'-untranslated region of the sequence is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map tmst2-receptor to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of genomic clones or clones from which the express sequence tag (EST) was derived, and the longer the better. For example, 2,000 bp is good, 4,000 is better, and more than 4,000 is probably not necessary to get good results a reasonable percentage of the time. For a review of this technique see Verma et al., *Human Chromosomes: A Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man* (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals. then the mutation is likely to be the causative agent of the disease.

With current resolution of physical mapping and genetic mapping techniques, a cDNA precisely localized to a chromosomal region associated with the disease could be on of between 50 and 500 potential causative geties (This assumes 1 megabase mapping resolution and one gene per 20 kb).

The nucleic acid molecule(s) of the present invention are also used as anti-sense inhibitors of tmst2 receptor expression. Such inhibition may be effected by nucleic acid molecules which are complementary to and hybridize to expression control sequences (triple helix fonnation) or to tmst2-receptor miNIA. Anti-sense probes may be designed by available techniques using the sequence of tmst2-receptor disclosed herein. Anti-sense inhibitors provide informnation relating to the decrease or absence of a tmst2-receptor polypeptide in a cell or organism. The nucleic acid molecules of the invention may be used for gene therapy. Nucleic acid molecules which express tmst2-receptor in vivo provide information relating to the effects of the polypeptide in cells or organisms. Tmst2-receptor nucleic acid molecules, fragments, and/or derivatives that do not themselves encode biologically active polypeptides may be useful as hybridization probes in diagnostic assays to test, either qualitatively or quantitatively, for the presence of tmst2 receptor DNA or corresponding RNA in mammalian tissue or bodily fluid samples.

Tmst2-receptor polypeptide fragments, variants, and/or derivatives, whether biologically active or not, are useful for preparing antibodies that bind to an tmst2-receptor polypeptide. The antibodies may be used for in vivo and in vitro diagnostic purposes, such as in labeled form to detect the presence of tmst2-receptor polypeptide in a body fluid or cell sample. The antibodies may bind to an tmst2-receptor polypeptide so as to diminish or block at least one activity characteristic of an tnst2-receptor polypeptide, or may bind to a polypeptide to increase an activity.

Genetically Engineered Non-Human Mammals

The present invention further includes non-human mammals such as mice, rats, rabbits, goats, or sheep in which the gene (or genes) encoding tmst2-receptor polypeptides in which either the native form of the gene(s) for that mammal or a heterologous tmst2-receptor polypeptide gene(s) is (are) over expressed by the mammal, thereby creating a "transgenic" mammal. Such transgenic mammals may be prepared using well known methods such as those described in U.S. Pat. No. 5,489,743 and PCT Publication No. W094/28 122, incorporated herein by reference.

Additionally included within the scope of the present invention are non-human mammals such as mice, rats, rabbits, goats, or sheep in which the gene (or genes) encoding a native tmst2-receptor polypeptide has (have) been disrupted ("knocked out") such that the level of expression of this gene or genes is (are) significantly decreased or completely abolished. Such mammals may be prepared using techniques and methods such as those described in U.S. Pat. No. 5,557,032, incorporated herein by reference.

The present invention further includes non-human mammals in which the promoter for one or more of the tmst2-receptor polypeptides of the present invention is either activated or inactivated (using homologous recombination methods as described below) to alter the level of expression of one or more of the native tmst2-receptor polypeptides.

These non-human mammals may be used for drug candidate screening. The impact of a drug candidate on the mammal may be measured. For example, drug candidates may decrease or increase expression of the tmst2-receptor polypeptide gene. In certain embodiments, the amount of tmst2-receptor polypeptide or a fragment(s) that is produced may be measured after exposure of the mammal to the drug candidate. Addionally. certain embodiments, one may detect the actual impact of the drug candidate on the animal. For example, over expression of a particular gene may result in, or be associated with, a disease or pathological condition. in such cases, one may test a drug candidate's ability to decrease expression of the gene or its ability to prevent or inhibit a pathological condition. In other examples, production of a particular metabolic product such as a fragment of a polypeptide, may result in, or be associated with, a disease or pathological condition. In such cases, one may test a drug candidate's ability to decrease production of such a metabolic product or its ability to prevent or inhibit a pathological condition, Microarray It will be appreciated that DNA microarray technology can be utilized in accordance with the present invention. DNA microarrays are miniature, high density arrays of nucleic acids positioned on a solid support, such as glass. Each cell or element within the array has numerous copies of a single species of DNA which acts as a target for hybridization for its cognate mRNA. In expression profiling using DNA microarray technology, mRNA is first extracted fronm a cell or tissue sample and then converted enzyrnatically to fluorescently labeled cDNA. This material is hybridized to the microarray and unbound cDNA is removed by washing. The expression of discrete genes represented on the array is then visualized by quantitating the amount of labeled cDNA which is specifically bound to each target DNA. In this way, the expression of thousands of genes can be quantitated in a high throughput, parallel manner from a single sample of biological material.

This high throughput expression profiling has a broad range of applications with respect to the tmst2-receptor molecules of the invention, including, but not limited to: the identification and validation of tmst2-receptor disease-related genes as targets for therapeutics; molecular toxicology of tmst2-receptor molecules and inhibitors thereof; stratification of populations and generation of surrogate markers for clinical trials; and enhancing tmst2-receptor related small molecule drug discovery by aiding in the identification of selective compounds in high throughput screens (H TS).

Assaying for Other Modulators of tmst2-Receptor Polypeptide Activity

In some situations, it may be desirable to identify molecules that are modulators, i.e., agonists or antagonists, of the activity of tmst2-receptor polypeptide. Natural or synthetic molecules that modulate tmst2-receptor can be identified using one or more of the screening assays described below. Such molecules may be administered either in an ex vivo manner, or in an in vivo manner by local or iv injection, or by oral delivery, implantation device, or the like.

The following definition is used herein for describing the assays:

"Test molecule(s)" refers to the molccule(s) that is/are under evaluation for the ability to modulates i.e., increase or decrease) the activity of an tmst2-receptor polypeptide. Most commonly, a test molecule will interact directly with an tmst2-receptor polypeptide. However, it is also contemplated that a test molecule may also modulate tmst2-receptor polypeptide activity indirectly, such as by affecting tmst2 like gene expression, or by binding to an tmst2-receptor ligand. In one embodiment, a test molecule will bind to a tmst2-receptor polypeptide with an affinity constant of at least about $10^{-6}$M, preferably about $10^{-8}$M, more preferably about $10^{-9}$M, and even more preferably about $10^{-10}$M.

Methods for identifying compounds which interact with tmst2-receptor polypeptides are encompassed by the invention. In certain embodiments, a tmst2-receptor polypeptide is incubated with a test molecule under conditions which permit the interaction of the test molecule to tmst2-reccptor polypeptide, and the extent of interaction can be measured. The test molecule(s) can be screened in a substantially purified form or in a crude mixture.

Test molecules may be nucleic acid molecules, proteins, peptides, carbohydrates, lipids or small molecular weight organic or inorganic compounds which interacts with tmst2 like polypeptide to regulate its activity. Molecules which regulate tmst2-receptor polypeptide expression include nucleic acids which are complementary to nucleic acids encoding an tmst2-receptor polypeptide, or are complementary to nucleic acids sequences which direct or control the expression of tmst2-receptor polypeptide, and which act as anti-sense regulators of expression. Once a set of test molecules has been identified as interacting with a tmst2-receptor polypeptide, the molecules may be further evaluated for their ability to increase or decrease tmst2-receptor activity.

The measurement of the interaction of test molecules with tmst2-receptor polypeptides may be carried out in several formats, including cell-based binding assays, membrane binding assays, solution-phase assays and immunoassays. In general, test molecules are incubated with a tmst2-receptor polypeptide for a specified period of time and the extent of binding to a tmst2-receptor polypeptide is determined by filtration, electrochemiluminescent (ECL, ORIGEN system by IGEN), cell-based or immunoassays.

Homogenous assay technologies for radioactivity (SPA; Amersham) and time resolved fluorescence (HTRF, Packard) can also be implemented. Binding can be detected by labeling with radioactive isotopes ($^{125}$I,$^{35}$S, $^{3}$H), fluorescent dyes (fluorescein), lanthanides such as Europium ($Eu^{3-}$) chclates or cryptates, orbipyridyl-ruthenium ($Ru^{2-}$) complexes. It is understood that the choice of a labeled probe will depend upon the detection system used. Alternatively, a tmst2-receptor polypeptide may be modified withi an unlabeled epitope tag (e.g., biotin, peptides, His6, myc, Fc) and bound to proteins such as streptavidin, anti-peptide or anti-protein antibodies which have a detectable label as described above.

The interaction of test molecules to tmst2-receptor polypeptides may also be assayed directly using polyclonal or monoclonal antibodies in an immunoassay. Alternatively, modified forms of tmst2-receptor polypeptides containing epitope tags as described herein may be used in solution and immunoassays.

In one embodiment, a tmst2-receptor agonist or antagonist may be a protein, peptide, carbohydrate, lipid or small molecular weight molecule which interacts with tmst2-receptor to regulate its activity. Potential protein antagonists of tmst2-receptor include antibodies which bind to active regions of the polypeptide and inhibit or eliminate at least once activity of tmst2-receptor. Molecules which regulate tmst2-receptor polypeptide expression may include nucleic acids which are complementary to nucleic acids encoding a tmst2-receptor polypeptide, or are complementary to nucleic acids sequences which direct or control expression of polypeptide, and which act as anti-sense regulators of expression.

In the event that tmst2-receptor polypeptides display biological activity through an interaction with a ligand, a variety of in vitro assays may be used to measure binding of a tmst2-receptor polypeptide to the corresponding binding partner (such as a selective binding agent or ligand). These assays may be used to screen test molecules for their ability to increase or decrease the rate and/or the extent of binding of a tmst2-receptor polypeptide to its binding partner. In one assay, a tmst2-receptor polypeptide is immobilized in the bottom of the wells of a microtiter plate. Radiolabeled tmst2-receptor binding partner (for example, iodinated tmst2-receptor binding partner) and the test molecule(s) can then be added either one at a time (in either order) or simultaneously to the wells. After incubation, the wells can be washed and counted, using a scintillation counter for, radioactivity to determine the extent to which the binding partner bound to tmst2 receptor polypeptide. Typically, the molecules will be tested over a range of concentrations, and a series of control wells lacking one or more elements of the test assays can be used for accuracy in the evaluation of the results. An alternative to this method involves reversing the "positions" of the proteins, i.e., immobilizing tmst2-receptor binding partner to the microtiter plate wells, incubating with the test molecule and radiolabeled tmst2-receptor and determining the extent of tmst2-receptor binding (see, for example, Chapter 18 of *Current Protocols in Molecular Biology*, Ausubel et al., eds., John Wiley & Sons, New York, N.Y. (1995)).

As an alternative to radiolabelling, an tmst2-receptor polypeptide or its binding partner may be conjugated to biotin and the presence of biotinylated protein can then be detected using streptavidin linked to an enzyme, such as horseradish peroxidase (HRP) or alkaline phosphatase (AP), that can be detected colorimetrically, or by fluorescent tagging of streptavidin. An antibody directed to an tmst2-receptor polypeptide or to an tmst2-receptor binding partner and is conjugated to biotin may also be used and can be detected after incubation with enzyme-linked streptavidin linked to AP or HRP.

A tmst2-receptor polypeptide and a tmst2-receptor binding partner can also be immobilized by attachment to agarose beads, acrylic beads or other types of such solid phase substrates. The substrate-protein complex can be placed in a solution containing the complementary protein and the test compound; after incubation, the beads can be precipitated by centriftigation, and the amount of binding between an tmst2-receptor polypeptide and its binding partner can be assessed using the methods described herein. Alternatively, the substrate-protein complex can be immobilized in a column and the test molecule and complementary protein are passed through the column. The formation of a complex between an tmst2-receptor polypeptide and its binding partner can then be assessed using any of the techniques set forth herein, i.e., radiolabeling, antibody binding, or the like.

Another in vitro assay that is useful for identifying a test molecule which increase or decrease the formation of a complex between a tmst2-receptor binding protein and a tmst2-receptor binding partner is a surface plasmon resonance detector system such as the Biacore assay system (Uppsula. Sweden). The Biacore system may be carried out using the manufacturer's protocol. This assay essentially involves the covalent binding of either tmst2-receptor or a tmst2-receptor binding partner to a dextran-coated sensor chip which is located in a detector. The test compound and the other complementary protein can then be injected either simultaneously or sequentially into the chamber containing the sensor chip and the amount of complementary protein that binds can be assessed based on the change in molecular mass which is physically associated with the dextran-coated side of the sensor chip; the change in molecular mass can be measured by the detector system.

In some cases, it may be desirable to evaluate two or more test compounds together for their ability to increase or decrease formation of a complex between a tmst2-receptor polypeptide and a tmst2-receptor binding partner complex. In these cases, the assays set forth above can be readily modified by adding such additional test compound(s) either simultaneous with, or subsequent to, the first test compound. The remainder of steps in the assay are as set forth herein.

In vitro assays such as those described above may be used advantageously to screen rapidly large numbers of compounds for effects on complex formatioll by tmst2-receptor and tmst2-receptor binding partner. The assays may be automated to screen compounds generated in phage display, synthetic peptide and chemical synthesis libraries.

Compounds which increase or decrease the formation of a complex between a tmst2-receptor polypeptide and a tmst2-receptor binding partner may also be screened in cell culture using cells and cell lines expressing either tmst2-receptor or tmst2-receptor binding partner. Cells and cell lines may be obtained from any mammal, but preferably will be from human or other primate, canine, or rodent sources. The binding of an tmst2-receptor polypeptidc to cells expressing tmst2-receptor binding partner at the surface is evaluated in the presence or absence of test molecules and the extent of binding may be determined by, for example, flow cytometry using a biotinylated antibody to an tmst2-receptor binding partner. Cell culture assays may be used advantageously to further evaluate compounds that score positive in protein binding assays described herein.

Cell cultures can also be used to screen the impact of a drug candidate. For example, drug candidates may decrease or increase the expression of the tmst2-receptor gene. In certain embodiments, the amount of tmst2-receptor polypeptide that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

A yeast two hybrid system (Chien et al., *Proc. Natl. Acad. Sci. USA*, 88:9578–9583 (1991)) can be used to identify novel polypeptides that bind to, or interact with, tmst2-receptor polypeptides. As an example, hybrid constructs comprising DNA encoding a cytoplasmic domain of an tmst2-receptor polypeptide fused to a yeast GAL4-DNA binding domain may be used as a two-hybrid bait plasmid. Positive clones emerging from the screening may be characterized further to identify interacting proteins.

P38 Inhibitors

A new approach to intervention between the extracellular stimulus and the secretion of IL-I and TNFα from the cell involves blocking signal transduction through inhibition of a kinase which lies on the signal pathway. One example is through inhibition of P-38 (also called "RK" or "SAPK-2", Lee et al., *Nature*, 372:739 (1994)), a known ser/thr kinase (clone reported in Han et al., *Biochimica Biophysica Acta*, 1265:224–227 (1995)). A linear relationship has been shown for effectiveness in a competitive binding assay to P-38, and the same inhibitor diminishing the levels of IL-1 secretion from monocytes following LPS stimulation. Following LPS stimulation of monocytes, the levels of messenger RNA for TNF-a have been shown to increase 100 fold, but the protein levels of TNF-α are increased 10,000 fold. Thus, a considerable amplification of the TNF signaling occurs at the translational level. Following LPS stimulation of monocytes in the presence of a P-38 inhibitor, the levels of mRNA are not affected, but the levels of final TNF protein are dramatically reduced (up to 80–90% depending on the effectiveness of the P-38 inhibitor). Thus, the above experiments lend strong support to the conclusion that inhibition of P-38 leads to diminished translational efficiency. Further evidence that TNFα is under translational control is found in the deletion experiments of Beutler et al. and Lee, wherein segments of 3' untranslated mRNA (3' UTR) are removed resulting in high translational efficiency for TNFα. More importantly, the P-38 inhibitors did not have an effect on the level of TNFα (i.e., translational efficiency) when the appropriate segments of TNFα mRNA are deleted. Thus, the correlative data between the level of binding of inhibitors to P-38 and the diminished IL-1 and TNFα levels following LPS stimulation with the same inhibitors, plus the above biochemical evidence regarding the effect of P-38 inhibitors on translational efficiency of both TNFα and IL-1 make a strong cause and effect relationship. The role of P-38 in the celi is still being delineated; so therefore, other beneficial effects regarding inflammatory diseases or other disease states obtained from its inhibition maybe forthcoming.

Elevated levels of TNFα and/or IL-1 may contribute to the onset, etiology, or exacerbate a number of disease states, including, but not limited to: rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; antiviral therapy including those virses sensitive to TNFα inhibition—HIV-1, HIV-2, HIV-3, cytomegalovirus (CMV), influenza, adenovirtlis, and the herpes viruses including HSV-1, HSV-2, and herpes zoster; muscle degeneration; cachexia; Reiter's syndrome; type II diabetes; bone resorption diseases; graft vs. host reaction; ischemia reperfusion injury; atherosclerosis; brain trauma; Alzheimer's disease; multiple sclerosis; cerebral malaria; sepsis; septic shock; toxic shock syndrome; fever and mylagias due to infection.

Substituted imidazole, pyrrole, pyridine, pyrimidine and the like compounds have been described for use in the treatment of cytokine mediated diseases by inhibition of proinflammatorycytokines, such as IL-1, IL-6, IL-8 and TNF. Substituted imidazoles for use in the treatment of cytokine mediated diseases have been described in U.S. Pat. No. 5,593,992; WO 93/14081; WO 97/18626; WO 96/21452; WO 96/21654; WO 96/40143; WO 97/05878; WO 97/05878; (each of which is incorporated herein by reference in its entirety). Substituted imidazoles for use in the treatment of inflammation has been described in U.S. Pat. No. 3,929,807 (which is incorporated herein by reference in its entirety). Substituted pyrrole compounds for use in the treatment of cytokine mediated diseases have been described in WO 97/05877; WO 97/05878; WO 97/16426; WO 97/16441; and WO 97/16442 (each of which is incorporated herein by reference in its entirety). Substituted aryl and heteroaryl fused pyrrole compounds for use in the treatment of cytokine mediated diseases have been described in WO 98/22457 (which is incorporated herein by reference in its entirety). Substituted pyridine, pyrimidine, pyrimidinone and pyridazine compounds for use in the treatment of cytokine mediated diseases have been described in WO 98/24780; WO 98/24782; WO 99/24404; and WO 99/32448 (each of which is incorporated herein by reference in its entirety).

Internalizing Proteins

The TATprotein sequence (from HIV) can be used to internalize proteins into a cell by targeting the lipid bi-layer component of the cell membrane. See e.g., Falwell et al., *Proc. Natl. Acad. Sci.*, 91: 664–668 (1994). For example, an 11 amino acid sequence (YGRKKRRQRRR; SEQ ID NO: 15) of the HIV TAT protein (termed the "protein transduction domain", or TAT PDT) has been shown to mediate delivery of large bioactive proteins such as β-galactosidase and p27Kip across the cytoplasmic membrane and the nuclear membrane of a cell. See Schwarze et al., *Science*, 285: 1569–1572 (1999); and Nagahara et al., *Nature Medicine*, 4: 1449–1452, (1998). Schwartze et al. (*Science*, 285: 1569–72 (1999)) demonstrated that cultured cells acquired β-gal activity when exposed to a fusion of the TAT PDT and β-galactosidase. Injection of mice with the TAT-β-gal fusion proteins resulted in β-gal expression in a number of tissues, including liver, kidney, lung, heart, and brain tissue.

It will thus be appreciated that the TAT protein sequence may be used to internalize a desired protein or polypeptide into a cell. In the context of the present invention, the TAT protein sequence can be fused to another molecule such as a tmst2-receptor antagonist (i.e.: anti-tmst2-receptor selective binding agent or small molecule) and administered intracellularly to inhibit the activity of the tmst2-receptor molecule. Where desired, the tmst2-receptor protein itself, or a peptide fragment or modified form of tmst2-receptor may be fused to such a protein transducer for administrating to cells using the procedures, described herein.

Cell Source Identification Using tmst2-Receptor Polypeptide

In accordance with certain embodiments of the invention, it may be useful to be able to determine the source of a certain cell type associated with an tmst2-receptor polypeptide. For example, it may be useful to determine the origin of a disease or pathological condition as an aid in selecting an appropriate therapy.

Tmst2-receptor polypeptide is specifically associated with bone marrow associated stromal cells. Thus, if one knows that particular cells produce tmst2-receptor polypeptide or contain nucleic acids that encode tmst2-receptor polypeptide, one will know that such cells are derived from the marrow. According to certain embodiments, it may be useful to be able to deterniine the source of a certain cell type. For example, it may be useful to deteniine the origin of a disease or pathological condition which may aid in selecting appropriate therapy. In certain embodiments, nucleic acid encoding tmst2-receptor polypeptide can be used as a probe to identify bone marrow-derived cells by screening the nucleic acids of the cells with such a probe. In other embodiments, one may use the tmst2-receptor polypeptide to make antibodies that are specific for tmst2-receptor polypeptide. Such antibodies can be used to test for the presence of tmst2-receptor polypeptide in cells, and thus, used to determine if such cells are marrow derived.

Tmst2-receptor-Polypeptide Compositions and Administration

Members of the TNF ligand family have been implicated in mediation of a number of diseases. The pleiotropic nature of the TNF and related ligand family prevents generalization about whether it is beneficial or injurious. It is clear that in some instances, the local effects of TNF and other members of the TNF-ligand family cytokines improve host defense mechanisms by mobilizing substrate, increasing immune cell function, stimulating inflammation and in killing cancer cells. However, in other cases the toxicity of TNF and related cytokines may cause disease by mediating shock, tissue injury, or catabolic injury. There are many diseases wherein members of the TNF ligand family mediated injury-may be treated or ameliorated by the administration of, soluble forms of the receptor or other ligand binding molecules. These diseases include acquired-immunodeficiency syndrome (AIDS), anemia, autoimmune diseases, cachcxia, cancer, cerebral malaria, diabetes mellitus, disseminated intravascular coagulopathy, erythroid sick syndrome, hemorrhagic shock, hepatitis, insulin resistance, leprosy, leukemia, lymphoma. meningitis, multiple sclerosis, myocardial ischaemia, obesity, rejection of transplanted organs, rheumatoid arthritis, septic shock syndromiie, stroke, adult respiratory distress syndrome (ARDS), tuberculosis, and a number of viral diseases.

Pharmaceutical compositions of tmst2-reccptor polypeptides are within the scope of the present invention for prophylactic and therapeutic treatment of humans and animals for indications resulting from abnormal expression of tmst2-receptor or where it is determined that administration of tmst2-receptor polypeptide will result in the amelioration or cure of the indications. Such tmst2-receptor pharmaceutical compositions may comprise a therapeutically effective amount of a tmst2-receptor polypeptide and/or its binding partner, or therapeutically active fragment(s), variant(s), or derivative(s) thereof in admixture with a pharmaceutically or physically acceptable additives and/cr carriers. Suitable formulation materials or pharmaceutically acceptable agents include, but are not limited to, antioxidants, preservatives, colors, flavoring, and diluting agents, emulsifying agents, suspending agents. solvents. fillers, bulking agents, buffers, deliverv vehicles, diluents, excipients, and/or pharmaceutical adjuvants. Typically, a therapeutic compound containing tmst2-receptor polypeptide(s) will be administered in the form of a composition comprising purified polypeptide, fragment(s), variant(s), or derivative(s) in conjunction with one or more physiologically acceptable carriers, excipients, or diluents. For example, a suitable vehicle may be water for injection, physiological solution, or artificial cerebrospinal fluid possibly supplemented with other materials common in compositions for parenteral delivery.

Neutral buffered saline or saline mixed with serum albumin are exemplary appropriate carriers. Preferably, the product is formulated as a lyophilizate usinty appropriate excipients (e.g., sucrose). Other standard carriers, diluents, and excipients may be included as desired. Other exemplary compositions comprise Tris buffer of about pH 7.0–8.5, or acetate buffer of about pH 4.0–5.5, which may further include sorbitol or a suitable substitute therefor. The pH of the solution should also be selected based on the relative solubility of tmst2 at various pHs.

The primary solvent in a composition may be either aqueous or non-aqueous in nature. In addition, the vehicle may contain other formulation materials for modifying or maintaining the pH, osmolarity, viscosity, clarity, color, isotonicity, sterility, stability, rate of dissolution, or odor of the formulation. Similarly, the composition may contain additional formulation materials for modifying or maintaining the rate of release of tmst2-receptor protein, or for promoting the absorption or penetration of tmst2-receptor protein.

Compositions comprising the tmst2-receptor polypeptide compositions can be administered parentally. Alternatively, the compositions may be administered intravenously or subcutaneously. When systemically administered, the therapeutic compositions for use in this invention may be in the form of a pyrogen-free, parentally acceptable aqueous solution. The preparation of such phaniaceutically acceptable protein solutions, with due regard to pH, isotonicity, stability and the like, is within the skill of the art.

Therapeutic formulations of tmst2-receptor polypeptide compositions useful for practicing the present invention may be prepared for storage by mixing the selected composition having the desired degree of purity with optional physiologically acceptable carriers, excipients, or stabilizers (*Remington's Pharmaceutical Sciences*, 18th Edition, A. R. Gennaro, ed., Mack Publishing Company [1990]) in the fom of a lyophilized cake or an aqueous solution.

Acceptable carriers, excipients or stabilizers are nontoxic to recipients and are preferably inert at the dosages and concentrations employed, and include buffers (such as borate, bicarbonate, Trsi-HCl, phosphates, citrates, or other organic acids); antioxidants (such as ascorbic acid, sodium sulfite or hydrogen sulfite); low molecular weight polypeptides; proteins (such as serum albumin, gelatin, or immunoglobulins); hydrophilic polymers (such as polyvinylpyrrolidone); amino acids (such as glycine, glutamine, asparagine, arginine or lysine); fillers; monosaccharides, disaccharides, and other carbohydrates (such as glucose, mannose, or dextrins); chelating agents (such as EDTA); sugar alcohols (such as mannitol or sorbitol); salt-forming counterions (such as sodium); and/or nonionic surfactants (such as Tween, plur-onics or polyethylene glycol (PEG)).

An effective amount of the tmst2-receptor polypeptide(s) composition to be employed therapeutically will depend, for example, upon the therapeutic objectives such as the indication for which the composition is being used, the route of administration (e.g., whether it is administered locally or systemically), and the condition ol the patient (e.g., patient's general health, anaureuesis, age, weight, sex). It Is essential, when detenninilln the therapeutically effective dose, to take into account the quantity of tmst2-receptor or other members of the TNF family of ligand secreted which are responsible for the disease as well as the quantity of endogenous tmst2-receptor. Basically, it can be assumed that for effective treatment of a disease triggered by the secretion of thei cytokine(s), at least the same molar amount of the tmst2-receptor polypeptide(s) is required as quantity of ligand secreted, and possibly a multiple excess might be needed, although less may be needed depending on the nature of the specific ligand involved and the nature of its interaction with tmst2-receptor. Accordingly, it will be necessary for the therapist to titer the dosage and/or in vivi modify the route of administration as required to obtain the optimal therapeutic effect. A typical daily dosage may range from about 0.1 mg/kg to up to 100 mg/kg or more. depending on the factors mentioned above. Typically, a clinician will administer the composition until a dosage is reached that achieves the desired effect. The composition may therefore be administered as a single dose, or as two or more doses (which may or may not contain the same amount of tmst2-receptor polypeptide) over time, or as a continuous infusion via implantation device or catheter.

An effective amount of an tmst2-receptor pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the tmst2-receptor molecule is being used, the route of administration, and the size (body weight, body surface or organ size) and condition (the age and general health) of the patient. Accordingly, the clinician may titer the dosage and modify the route of administration to obtain the optimal therapeutic effect.

The tmst2-receptor polypeptide composition to be used for in vivo administration must be sterile. This is readily accomplished by filtration through sterile filtration membranes. Where the composition is lyophilized, sterilization using these methods may be conducted either prior to or following lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

Once the phanmaceutical composition has been formulated, it may be stored in sterile vials as a solution, suspension, gel, emulsion, solid, or a dehydrated or lyophilized powder. Such fonrulations may be stored either in a ready-to-usc form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

Effective administration forms, such as (I) slow-release fonnulations, (2) inhalant mists, or (3) orally active formulations are also envisioned. Pharmaceutical composition comprising therapeutically effective dose of the tmst2-receptor polypeptide also may be formulated for parenteral administration. Such parenterally administered therapeutic compositions are typically in the form of a pyrogen-free, parenterally acceptable aqueous solution comprising tmst2-receptor in a pharmaceutically acceptable vehicle. The tmst2-receptor pharmaceutical compositions also may include particulate preparations of polymeric compounds such as polylactic acid, polyglycolic acid, etc. or the introduction of tmst2-recсptor into liposomes. Hyaluronic acid may also be used, and this may have the effect of promoting sustained duration in the circulation.

When parenteral administration is contemplated, the therapeutic compositions for use in this invention may be in the form of a pyrogen-free, parenterally acceptable aqueous solution comprising the desired tmst2-receptor molecule in a pharmaceutically acceptable vehicle. A particularly suitable vehicle for parenteral injection is sterile distilled water in which an tmst2-receptor molecule is formulated as a sterile, isotonic solution, properly preserved. Yet another preparation can involve the formulation of the desired molecule with an agent, such as injectable microspheres, bio-erodible particles, polymeric compounds (polylactic acid,polyglycolic acid), or beads, or liposomes, that provides for the controlled or sustained release of the product which may then be delivered as a depot injectioni. Ilyaluronic acid may also be used, and this may have the effect of promoting sustained duration in the circulation. Other suitable means for the introduction of the desired molecule include implantable drug delivery devices.

The preparations of the present invention may include other components, for example parenterally acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Suitable preservatives include, but arenot limited to, benzalkonium chloride, thimerosal, phenethyl alcohol, methylparaben, propylparaben, chlorhexidine, sorbic acid and the like. Hydrogen peroxide may also be used as preservative. Suitable cosolvents are for example glycerin, propylene glycol and polyethylene glycol. Suitable complexing agents are for example caffeine, polyvinylpyrrolidone, beta-cyclodextrin or hydroxypropyl-beta-cyclodextrin. Suitable surfactants or wetting agents include sorbitan esters, polysorbates such as polysorbate 80, tromethamnine, lecithin, cholesterol, tyloxapal and the like. The buffers can be conventional buffers such as borate, citrate, phosphate, bicarbonate, or Tris-HCl.

The formulation components are present in concentration that are acceptable to the site of administration. For example, buffers are used to maintain the composition at physiological pH or at slightly lower pH, typically within a pH range of from about 5 to about 8.

In one embodiment, a pharmaceutical composition may be fonnulated for inhalation. For example, tmst2-receptor may be formulated as a dry powder for inhalation. Tmst2-receptor polypeptide or tmst2-receptor polynucleotide inhalation solutions may also be formulated with a propellant for aerosol delivery. In yet another embodiment, solutions may be nebulized. Pulmonary administration is further disclosed in PCT application No. PCT/US94/001875 which discusses pulmonary deleivery of chemically modified proteins.

It is also contemplated that certain formulations containing tmst2-receptor can be administered orally. The tmst2-receptor which is administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degrad(ation is minimized. Additional agents may be included to facilitate absorption of the receptor polypeptide. Diluents, flavorings, low melting point waxes, vegetable oils, lubricants, suspending agents, tablet disintegrating agents, and binders may also be employed.

Another phanmaceutical composition may involve an effective quantity of tmst2-receptor in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional tmst2-receptor phanracCutical compositions will be evident to those skilled in the art, including formulations involving tmst2-receptor in sustained- or controlled-release delivery fonmulations. Techniques for formulating a variety of other sustained- or controlled-delivery means, such as liposome carriers, bio-erodible microparticles or porous beads and depot injections, are also known to those skilled in the art. See, for example, PCT/US93/00829 which discloses controlled release of porous polymeric microparticles for the delivery of pharmaceutical compositions. Additional examples of sustained-release preparations include semipermeable polymer materials in the form of matrices shaped articles e.g., film or microcapsules.

Regardless of the manner of administration, the specific dose may be calculated according to body weight, body surface area or organ size. Further refinement of the calculations necessary to determinc the appropriate dosage for treatment involving each of the above mentioned fonmulations is routinely made by those of ordinary skill in the art and is within the ambit of tasks routinely performed by them. Appropriate dosages may be ascertained through use of appropriate dose-response data. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

The frequency ofdosin(g will depend upon the pharmacokitnetic parameters of the tmst2-receptor molecule in the fonnulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the composition is in accord with known methods, e.g. oral, injection or infusion by intravenous, intraperitoneal, intracerebral (intraparenchymal), intraventricular, intramuscular, intraocular, intraarterial, or intralesional routes, or by sustained release systems or implantation device which may optionally involve the use of a catheter. Where desired, the compositions may be administered continuously by infusion, bolus injection or by implantation device. Alternatively or additionally, the composition may be administered locally via implantation into the affected area of a membrane, sponge, or other appropriate material on to which tmst2-receptor polypeptide has been absorbed.

One may further administer the present pharmaceutical compositions by pulmonary administration, see, e.g., International Publication No: WO 94/20069, which discloses pulmonary delivery of chemically modified proteins, herein incorporated by reference. For ptilmonary delivery, the particle size should be suitable for delivery to the distal lung. For example, the particle size may be from 1 mm to 5 mm, however, larger particles may be used, for example, if each particle is fairly porous. Alternatively or additionally, the composition may be administered locally via implantation into the affected area of a membrane, sponge, or other appropriate material on to which receptor polypeptide has been absorbed or encapsulated. Where an implantation device is used, the device may be implanted into any suitable tissue or organ, and delivery may be directly through the device via bolus, or via continuous administration, or via catheter using continuous infusion.

Tmst2-receptor polypeptide and/or its binding partner may also be administered In a sustained release formulation or preparation. Suitable polymer compositions preferably have intrinsic and controllable biodegradability so that they persist for about a week to about six months; are non-toxic containing no significant toxic monomers and degrading into non-toxic components; are biocompatible, are chemically compatible with substances to be delivered, and tend not to denature the active substance; are sufficiently porous to allow the incorporation of biologically active molecules and their subsequent liberation from the polymer by diffusion, erosion or a combination thereof; are able to remain at the site of the application by adherence or by geometric factions, such as being fonmed in place or softened and subsequently molded or fonmed into microparticles which are trapped at a desired location; are capable of being delivered by techniques of minimum invasivity such as by catheter, laparoscope or endoscope. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers*, 22: 547–556 (1983)), poly (2-hydroxyethyl-methacrylate) (Langer et al., *J. Biomed. Mater. Res.*, 15: 167–277 (1981) and Langer, *Chem. Tech.*, 12: 98–105 (1982)), ethylene vinyl acetate (Langer et al., supra) or poly-D(−)-3-hydroxybutyric acid. (EP 133,988). Sustained-release compositions also may include liposomes, which can be prepared by any of several methods known in the art (e.g., Eppstein et al., *Proc. Natl. Acad. Sci. USA*, 82: 3688–3692 (1985)1; EP 36,676; EP 88,046; EP 143,949, incorporated herein by reference).

The tmst2-receptor polypeptides, variants, derivatives or fragments thereof, may be employed alone, together, or in combination with other phannaceutical compositions. The tmst2-receptor polypeptides, fragments, variants, and derivatives may be used in combination with cytokines, cytokine inhibitors, growth factors, antibiotics, anti-inflammatories, and/or chemotherapeutic agents as is appropriate for the indication being treated In some cases, it may be desirable to use tmst2-receptor polypeptide compositions in an ex vivo manner. Here, cells, tissues, or organs that have been removed from the patient are exposed to tmst2-receptor polypeptide compositions after which the cells, tissues and/or organs are subsequently implanted back into the patient.

In other cases, a tmst2-receptor polypeptide can be delivered by implalltinlo into patients certain cells that have been genetically engineered, using methods such as those described herein, to express and secrete the polypeptides, fragments, variants, or derivatives. Such cells may be animal or human cells, and may be autologous. heretologous, or xenogeneic. Optionally, the cells may be immortalized. In order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent the destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627, incorporated herein by reference. A system for encapsulating living cells is described in International Publication No: WO 91/10425 (Aebischer et al.). Techniques for formulating a variety of other sustained or controlled delivery means, such as liposome carriers, bio-erodible particles or beads, are also known to those in the art, and are described, for example, in U.S. Pat. No. 5,653,975, incorporated herein by reference. The cells, with or without encapsulation, may be implanted into suitable body tissues or organs of the patient.

As discussed above, it may be desirable to treat isolated cell populations such as stem cells, lymphocytes, red blood cells, chondrocytes, neurons, and the like; add as appropriate with one or more tmst2-receptor polypeptides, variants, derivatives and/or fragments. This can be accomplished by exposing the isolated cells to the polypeptide, variant, derivative, or fragment directly, where it is in a form that is perrneable to the cell membrane.

The present invention relates to improved methods for both the in vitro production of therapeutic proteins and for the production and delivery of therapeutic proteins by gene therapy.

Additional embodiments ofthe present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally silent tmst2-reccptor gyene, or an under expressed gene, and thereby produce a cell which expresses therapeutically efficacious amounts of tmst2-receptor polypeptides.

Homologous Recombination

It is further envisioned that tmst2-receptor protein may be produced by homologous recombination, or with recombinant production methods utilizing control elements introduced into cells already containing DNA encoding tmst2-receptor. For example, homologous recombination methods may be used to modify a cell that contains a normally transcriptionally silent tmst2-receptor gene, or an under expressed gene, and thereby produce a cell which expresses therapeutically efficacious amounts of tmst2-receptor. Homologous recombination is a technique originally developed for targeting genes to induce or correct mutations in transcriptionally active genes (Kucherlapati, *Prog. in Nucl. Acid Res. and Mol. Biol.*, 36:301, (1989)). The basic technique was developed as a method for introducing specific mutations into specific regions of the mammalian genoine (Thomas et al., *Cell*, 44:419–428, (1986); Thomas and Capecchi, *Cell*, 51:503–512, (1987); Doetschman et al., *Proc. Natl. Acad. Sci U.S.A.*, 85:8583–8587, (1988)) or to correct specific mutations within defective genes (Doetschman et al., *Nature*, 330:576–578, (1987)). Exemplary homologous recombination techniques are described in U.S. Pat. No. 5,272,071, EP Publication No: 9193051, EP Publication No. 505 500; PCT/US90/07642, International Publication No: WO 91/09955, incorporated herein by reference.

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA throLugh shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA which may interact with or control the expression of a tmst2-receptor polypeptide, e.g., flanking sequences. For example, a promoter/enhancer element, a suppresser, or an exogenous transcription modulatory element is inserted in the genome of the intended host cell in proximity and orientation sufficient to influence the transcription of DNA encoding the desired tmst2-receptor polypeptide. The control element controls a portion of the DNA present in the host cell genome. Thus, the expression of tmst2-receptor polyepetide may be achieved not by transfection of DNA that encodes the tmst2-receptor gene itself, but rather by the usc of targeting DNA (containing regions of homology with the endogenous gene of interest) coupled with DNA regulatory segments that provide the endogenous gene sequence with recognizable signals for transcription of a tmst2-receptor protein.

In an exemplary method, expression of a desired targeted gene in a cell (i.e., a desired endogenous cellular gene) is altered via homologous recombination into the cellular genome at a preselected site, by the introduction of DNA which includes at least a regulatory sequence, an exon and a splice donor site. These components are introduced into the chromosomal (genomic) DNA in such a manner that this, in effect, results in the production of a new transcription unit (in which the regulatory sequence, the exon and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is noirnally silent (unexpressed) in the cell as obtained, as well as increasing expression of a gene which is not expressed at physiologically significant levels in the cell as obtained. The embodiments further encompass changing the pattern of regulation or induction Such that it is different from the pattern of regulation or induction that occurs in the cell as obtained, and reducing (including eliminating) expression of a gene which is expressed in the cell as obtained.

One method by which homologous recombination can be used to increase, or cause, tmst2-receptor polypeptide production from a cell's endogenous tmst2-receptor gene involves first using homologous recombination to place a recombination sequence from a site-specific recombination system (e.g., Cre/loxP, FLP/FRT) (Sauer, *Curr. Opin. Biotech.*, 5:521–527, (1994); Sauer, *Meth. Enz.*, 225:890–900, (1993)) upstream (that is, 5' to) of the cell's endogenous genomic tmst2-receptor polypeptide coding region. A plasmid containing a recombination site homologous to the site that was placed just upstream of the genomic tmst2-receptor polypeptide coding region is introduced into the modified cell line along with the appropriate recombinase enzyme. This recombinase causes the plasmid to integrate, via the plasmid's recombination site, into the recombination site located just upstream of the genomic tmst2-receptor polypeptide coding region in the cell line (Baubonis and Saner, *Nucleic Acids Res.*, 21:2025–2029, (1993); O'Gorman et al., *Science*, 251:1351–1355, (1991)). Any flanking sequences known to increase transcription (e.g., enhancer/promoter, intron, translational enhancer), if properly positioned in this plasmid, would integrate in such a manner as to create a new or modified transcriptional unit resulting in de novo or increased tmst2-receptor polypeptide production from the cell's endogenous tmst2-receptor gene.

A further method to use the cell line in which the site specific recombination sequence had been placed just upstream of the cell's endogenous genomic tmst2-receptor polypeptide coding region is to use homologous recombination to introduce a second recombination site elsewhere in the cell line's genome. The appropriate recombinase enzyme is then introduced into the two-recombination-site cell line, causing a recombination event (deletion, inversion, translocation) (Sauer, *Curr. Opin. Biotech.*, sluprci, 1994; Saner, *Meth. Enz.*, supra, 1993) that would create a new or modified transcriptional unit resulting in de novo or increased tmst2-receptor polypeptide production from the cell's endogenous tmst2-receptor gene.

An additional approach for increasing, or causing, the expression of tmst2-receptor polypeptide from a cell's endogenous tmst2-receptor gene involves increasing, or causing, the expression of a gene or genes (e.g., transcription factors) and/or decreasing the expression of a gene or genes (e.g., transcriptional repressors) in a mariner which results in de novo or increased tmst2-receptor polypeptide production from the cell's endogenous tmst2-receptor gene. This method includes the introduction of a non-naturally occulTing polypeptide (e.g., a polypeptide comprising a site specific DNA binding domain fused to a transcriptional factor domain) into the cell such that de novo or increased tmst2 like polypeptide production from the cell's endogenous tmst2 like gene results.

The present invention further relates to DNA constructs useful in the method of altering expression of a target gene. In certain embodiments, the exemplary DNA constructs comprise: (a) one or more targeting sequences; (b) a regulatory sequence; (c) an exon; and (d) an unpaired splice-donor site. The targeting sequence in the DNA construct directs the integration of elements (a)–(d) into a target gene in a cell such that the elements (b)–(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)–(f) such that the elements of (b)–(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon. If the sequence of a particular gene is known, such as the nucleic acid sequence of tmst2-receptor presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA. The present invention, therefore, includes nuclCeotides encoding a tmst2-receptor molecule, which nucleotides may be used as targeting sequences.

Tmst2-receptor Cell Therapy and Geiie Therapy

Tmst2-receptor cell therapy. e.g., the implantation of cells producing tmst2-receptor, is also contemplated by the present invention. This embodiment would involves implanting cells capable of synthesizing and secreting a biologically active form of the soluble tmst2-receptor. Such soluble tmst2-receptor-producing cells can be cells that are natural producers of tmst2-receptor polypeptides or may be recombinant cells whose ability to produce tmst2-receptor has been augmented by transformation with a gene encoding the desired tmst2-receptor molecule or with a gene augmenting the expression of tmst2-receptor. Such a modification may be accomplished by means of a vector suitable for delivering the gene as well as promoting its expression and secretion. In order to minimize a potential immunological reaction in patients being administered a tmst2-receptor polypeptide, as may occur with the administration of a polypeptide of a foreign species, it is preferred that the natural cells producing tmst2-receptor be of human origin and produce human tmst2-receptor polypeptides. Likewise, it is preferred that the recombinant cells producing tmst2-receptor polypeptidesbe transformed with an expression vector containing a gene encoding a human tmst2-receptor polyepeptides.

Implanted cells may be encapsulated to avoid infiltration of surrounding tissue. Human or non-human animal cells may be implanted in patients in biocompatible, semipermeable polymeric enclosures or membranes that allow release of tmst2-receptor but that prevent destruction of the cells by the patient's immune system or by other detrimental factors from the surrounding tissue. Alternatively, the patient's own cells, transformed to produce tmst2-receptor ex vivo, may be implanted directly into the patient without such encapsulation.

Techniques for the encapsulation of living cells are known in the art, and the preparation of the encapsulated cells and their implantation in patients may be routinely accomplished. For example, Baetge et al. PCT/US94/09299 describes membrane capsules containing genetically engineered cells for the effective delivery of biologically active molecules. The capsules encapsulate cell transfected with recombinant DNA molecules comprising DNA sequences coding for biologically active molecules operatively linked to promoters that are not subject to down regulation in vivo upon implantation into a mammalian host. The capsules are biocompatible and are easily retrievable. The devices provide for the delivery of the molecules from living cells to specific sites within a recipient. See U.S. Pat. Nos. 4,892,538, 5,011,472, and 5,106,627, incorporated herein by reference. A system for encapsulating living cells is described in Aebischer et (it. (WO 91/1042, WO 91/10470); Winn et al., *Exper. Neurol.*, 113:322–329, 1991, Aebisclher et al., *Exper. Neurol.*, 111:269–275, 1991; and Tresco et al., *ASAIO*, 38:17–23, 1992.

In vivo and in vitro gene therapy delivery of tmst2-receptor is also encompassed by the present invention. In vivo gene therapy may be accomplished by introducing the gene encoding tmst2-receptor into cells via local injection of a polyucleotide molecule or other appropriate delivery vectors. (Hefti, *J. Neurobiology,*. 25:1418–1435, 1994). For example, a polynucleotide molecule encoding tmst2-receptor may be contained in an adeno-associated virus vector for delivery to the targeted cells (e.g., Johnson, International Publication No. WO 95/34670; International Application No. PCT/US95/07178). The recombinant adeno-associated virus (AAV) genome typically contains AAV inverted terminal repeats flanking a DNA sequence encoding tmst2-receptor operably linked to functional promoter and polyadenylation sequences.

Alternative viral vectors include, but are not limited to, retrovirus, adenovirus, herpes simplex virus and papilloma virus vectors. U.S. Pat. No. 5,672,344 (issued Sep. 30, 1997, Kelley et al., University of Michigan) describes an in vivo viral-mediated gene transfer system involving a recombinant neurotrophic HSV-1 vector. U.S. Pat. No. 5,399,346 (issued Mar. 21, 1995, Anderson et al., Department of Health and Human Services) provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (issued May 20, 1997, Woo et al., Baylor College of Medicine) involving adenoviral vectors; U.S. Pat. No. 5,672,510 (issued Sep. 30, 1997, Eglitis et al., *Genetic Therapy, Inc.*) involving retroviral vectors; and U.S. Pat. No. 5,635,399 (issued Jun. 3, 1997, Kriegler et al., *Chiron Corporation*) involving retroviral vectors expressing cytokines.

Nonviral delivery methods include, but are not limited to, liposome-mediated transfer, naked DNA delivery (direct injection), receptor-mediated transfer (ligand-DNA complex), electroporation, calcium phosphate precipitation and microparticle bombardment (e.g, gene gun). Gene therapy materials and methods may also include inducible promoters, tissue-specific enhancer-promoters. DNA sequences designed for site-specific integration, DNA sequences capable of providing a selective advantage over the parent cell, labels to identify transfonined cells, negative selection systems and expression control systems (safety measures), cell-specitic binding agents (for cell targetsin), cell-specific internalization factors, transcription factors to enhance expression by a vector as well as methods of vector manufacture. Such additional methods and materials for the practice of gene therapy techniques are described in U.S. Pat. No. 4,970,154 involving electroporation techniques; WO 9640958 involving, nuclear ligands; U.S. Pat. No. 5,679,559 describing a lipoprotein-contianing system for gene deleivery; U.S. Pat. No. 5,676,954 involving liposome carriers; U.S. Pat. No. 5,593,875 concerning methods for calcium phosphate transfection; and U.S. Pat. No. 4,945,050 wherein biologically active particles are propelled at cells at a speed whereby the particles penetrate the surface of the cells and become incorporated into the interior of the cells.

In yet other embodiments, regulatory elements can be included for the controlled expression of the tmst2-receptor gene in the target cell. Such elements are turned on in response to an appropriate effector. In this way, a therapeutic polypeptide can be expressed when desired. One conventional control means involves the use of small molecule dimerizers or rapalogs (as described in W09641865 (PCT/US96/099486); WO9731898 (PCT/US97/03137) and WO9731899 (PCT/US95/03157)) used to dimerize chimeric proteins which contain a small molecule-binding domain and a domain capable of initiating biological process, such as a DNA-binding protein or transcriptional activation protein. The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain which results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See, *Science,* 287:816–817, and 826–830 (2000).

Other suitable control means or gene switches include, but are not limited to, the following systems. Mifepristone (RU486) is used asa progesterone antagonist. Thie binding of a modified progesterone receptor ligand-binding domain to the progesterone antagonist activates transcription by forming a dimer of two transcription factors which then pass into the nucleus to bind DNA. The ligand binding domain is modified to eliminate the ability of the receptor to bind to the natural ligand. The modified steroid hormone receptor system is further described in U.S. Pat. No. 5,364,791; WO9640911, and WO9710337.

Yet another control system uses ecdysone (a fniit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain/DNA-binding domain/ligand-binding domain to initiate transcription. The ecdysone system is further described in U.S. Pat. No. 5,514,578; WO9738117; WO9637609; and WO9303162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758; 5,650,298 and 5,654,168.

It is also contemplated that tmst2-receptor gene therapy or cell therapy can further include the delivery of a second protein. For example, the host cell may be modified to express and release soluble forms of both tmst2-receptor and TNF-α, or tmst2-receptor and IL-1R. Alternatively, the tmst2-receptor and TNF-α, or tmst2-receptor and IL-1R, may be expressed in and released from separate cells. Such cells may be separately introduced into the patient or the cells may be contained in a single implantable device, such as the encapsulating membrane described above.

One manner in which g,ene therapy can be applied is to use the tmst2-receptor gene (either genomic DNA, cDNA, and/or synthetic DNA encoding a tmst2-receptor polypeptide, or a fragment, variant, or derivative thereof) which may be operably linked to a constitutive or inducible promoter to form a "gene therapy DNA construct". The promoter may be homologous or heterologous to the endogenous tmst2-receptor gene, provided that it is active in the cell or tissue type into which the construct will be inserted. Other components of the gene therapy DNA construct may optionally include, as required, DNA molecules designed for site-specific integration (e.g., endogenous flanking sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting) cell-specific internalization factors, and transcription factors to enhance expression by a vector as well as factors to enable vector manufacture.

This gene therapy DNA construct can then be introduced into the patient's cells (either er vivo or in vivo). One means for introducing the gene therapy DNA construct is via viral vectors. Suitable viral vectors typically used in gene therapy for delivery of gene therapy DNA constructs include, without limitation, adenovirus, adeno-associated virus, herpes simplex virus, lentivirus, papilloma virus, and retrovirus vectors. Some of these vectors, such as retroviral vectors, will deliver the gene therapy DNA construct to the chromosomal DNA of the patient's cells, and the gene therapy DNA construct can integrate into the chromosomal DNA; other vectors will function as episomes and the gene therapy DNA construct will remain in the cytoplasm. The use of gene therapy vectors is described, for example, in U.S. Pat. Nos. 5,672,344; 5,399,346; 5,631,236; and 5,635,399, incorporated herein by reference.

Alternative means to deliver gene therapy DNA constructs to a patient's cells without the use of viral vectors include, without limitation, liposome-mediated transfer, direct injection of naked DNA, receptor-mediated transfer (ligand-DNA complex), electroporation, calcium phosphate precipitation, and microparticle bombardment (e.g., "gene gun"). See U.S. Pat. No. 4,970,154; International Application No. WO 96/40958; U.S. Pat. No. 5,679,559; U.S. Pat. No. 5,676,954; and U.S. Pat. No. 5,593,875, incorporated herein by reference.

Another means to increase endogenous tmst2-receptor polypeptide expression in a ccil via gene therapy is to insert one or more enhancer elements into the tmst2-receptor polypeptide promoter, where the enhancer clement(s) can serve to increase transcriptional activity of the tmst2-receptor polypeptides gene. The enhancer element(s) used will be selected based on the tissue in which one desires to activate the gene(s); enhancer elements known to confer promoter activation in that tissue will be selected. For example, if a tmst2-receptor polypeptide is to be "turned on" in T-cells, the lck promoter enhancer element may be used. Here, the functional portion of the transcriptional element to be added may be inserted into a fragment of DNA containing the tmst2-receptor polypeptide promoter (and optionally vector, 5' and/or 3' flanking sequence, etc.) using standard cloning techniques. This construct, known as a "homologous recombination construct", can then be introduced into the desired cells either ex vivo or in vivo.

Gene therapy also can be used to decrease tmst2-receptor polypeptide expression where desired by modifying the nucleotide sequence of the endogenous promoter(s). Such modification is typically accomplished via homologous recombination methods. For example, a DNA molecule containing all or a portion of the promoter of the tmst2-receptor gene(s) selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing transcription of the corresponding tmst2-receptor gene. The deletion of the TATA box or transcription activator binding site in the promoter may be accomplished by generating a DNA construct comprising all or the relevant portion of the tmst2-receptor polypeptide promoter(s) (from the same or a related species as the tmst2-receptor gene(s) to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter seyncnt that has been modified. The construct may be introduced into the appropriate cells (either ex vivo or in vivo) either directly or via a viral vector as described herein. Typically, the integration of the construct into the genornic DNA of the cells will be via homologous recoinbination, where the 5' and 3' DNA sequences in the promoter construct can serve to help integrate the modified promoter region via hybridization to the endogenotis chromosomal DNA.

Other gene therapy methods may also be employed where it is desirable to inhibit the activity of one or more tmst2-receptor polypeptides. For example, antisense DNA or RNA molecules, whlilch hanvC a sequence that is complementary to at least a portion of the selected tmst2-reccptor polypeptide gene(s) can be introduced into the cell. Typically, each such antisense molecule will be complementary to the start site (5' end) of each selected tmst2-receptor gene. When the antisense molecule then hybridizes to the corresponding tmst2-receptor mRNA, translation of this mRNA is prevented or reduced. Antisence inhibitors provide infomiation relating to the decrease or absence of tmst2-receptor polypeptides in a cell or organism.

Alternatively, gene therapy may be employed to create a dominant-negative inhibitor of one or more tmst2-receptor polypeptides. In this situation, the DNA encoding a mutant full length or truncated polypeptide of each selected tmst2-receptor polypeptide can be prepared and introduced into the cells of a patient using either viral or non-viral methods as described herein. Each such mutant is typically designed to compete with endogenous polypeptide in its biological role.

In addition, an tmst2-receptor polypeptidc, whether biologically active or not, may be used as an immunogen, that is, the polypeptide contains at least one epitope to which antibodies may be raised. Selective binding agents that bind to an tmst2-receptor polypeptide (as described herein) may be used for in vivo and in vitro diagnostic purposes, including, but not limited to, use in labeled form to detect the presence of tmst2-receptor polypeptide in a body fluid or cell sample. The antibodies may also be used to prevent, treat, or diagnose a number of diseases and disorders, including those recited herein. The antibodies may bind to an tmst2-receptor polypeptide so as to diminish or block at least one activity characteristic of an tmst2 like polypeptide, or may bind to a polypeptide to increase at least one activity characteristic of an tmst2-i-eceptor polypeptide (including by increasing the pharmnacokinetics of the tmst2-receptor polypeptide).

Additional Uses of tmst2 like Nucleic Acids and Polypeptides

Nucleic acid molecules ofthe present invention (including those that do not themselves encode biologically active polypeptides) may be used to map the locations of the tmst2-receptor gene and related genes on chromosomes. Mapping may be done by techniques known in the art. such as PCR amplification and in situ hybridization.

Tmst2 like nucleic acid molecules (including those that do not themselves encode biologically active polypeptides), may be useful as hybridization probes in diagnostic assays to test, either qualitatively or quantitatively, for the presence of an tmst2 like DNA or corresponding RNA in mammalian tissue or bodily fluid samples.

The tmst2 like polypeptides may be used (simultaneously or sequentially) in combination with one or more cytokines, growth factors, antibiotics, anti-inflammatories, and/or chemotherapeutic agents as is appropriate for the indication being treated.

The following examples are intended for illustration purposes only, and should not be construed as limiting the scope of the invention in any way.

EXAMPLE 1

Isolation of Murine tmst2-Receptor Gene Using ΔkFGF-Signal Trap Method

Secretion signal trap method is a novel way to clone 5' ends of cDNAs encoding secreted proteins from a random cDNA library. Generally, signal trapping relies on the secretion of a reporter polypeptide by signal sequences present in a cDNA library. The secreted reporter polypeptide may be detected by a variety of assays based upon growth selection, enzyiatic activity or immune reactivity. (See U.S. Pat. No. 5,536,637; Klein et al., *Proc. Natl. Acad. Sci. USA*, 93:7108–7113 (1996); Imai et al., *J. Biol. Chem.*, 271:21514–21521 (1996)). Published PCT application No. WO 96/409904 describes signal trap cloning by selection for growth-factor dependent cell lines and is incorporated here in by reference.

In the instant case, a novel method for trapping signal sequence DNA from cDNA libraries was utilized to isolate and identify novel secreted proteins, including tmst2-receptor polypeptide. In the instant case a signal trap vector kFGF7 containing a DNA molecule encoding a reporter polypeptide that lacked a functional 5'-signal sequences was utilized in generating a cDNA library from a desired cell source. Secretion of the reporter polypeptide is indicative of the presence of functional signal sequence and may be detected by a variety of methods including growth under certain conditions, enzyme activity or immune reactivity. Significantly, the molecule of the present invention, tmst2-receptor polypeptide, was identified utilizing the method described below of selecting signal sequences in mammalian cells (NIH 3T3 cells) by using a reporter polypeptide (kFGF) which stimulated the growth of host cells.

Murine tmst2 cDNA was isolated from a mouse bone marrow stromal cell line cDNA library that was made using the signal trap kFGF7 vector, ΔkFGF7L, as previously described. Briefly, polyA⁺ RNA was prepared from mouse bone marrow stromal cell line using a commercially available RNA extraction kit (Trizol, LTI) and mRNA purification kit (Dynabeads, Dynal). The cDNA library was made according to the protocol of SuperScript Plasmid System for cDNA synthesis and Plasmid Cloning (GIBCO/BRL, Cat. No. 18248-013) with some modification. To make cDNA with random 3' ends followed by a Not I site, the oligonucleotide 1360-38 (SEQ ID NO: 1) was made and used as the primer for first strand cDNA synthesis.

1360-38 GGAAGGAAAAAAGCGGCCGCAA- CANNNNNNNN SEQ ID NO: 1

PolyA⁺ RNA (3 µg) and 400 ng of the primer was used in the first strand reaction. After second strand synthesis using published procedures, Sal I adapter ligation, and Not I digestion, double stranded cDNA was size selected by gel electrophoresis through 1.2% low melting agarose. Gel section containing DNA in the 200 to 800 bp range was excised and melted for 10 minutes at 70° C. DNA was recovered by extraction with phenol chloroform, followed by ethanol precipitation. The recovered cDNA was ligated into vector DkFGF7L previously digested with SalI and NotI; ligation positioned the cDNA fragments adjacent the kFGF gene lacking the 5'-signal peptide sequence. Ligation was carried out overnight at room temperature in a 20 µl reaction containing 50 ng vector DNA, 16 ng cDNA, 1× ligase buffer, and 1 ml of T4 ligase. The ligated DNA was precipitated and introduced into *E.coli* by electroporation as described in the protocol.

The isolation and identification of novel cDNAs using kFGF signal trapping method was based on the observation that NIH/3T3 cells transfected with kFGF signal trap vectors containing test DNA fragments and signal sequences continued to orow and form colonies in selection medium while NIH/3T3 cells transfected with empty vectors or untransfected NIH/3T3 cells did not grow in the selection medium.

Plasmid DNA from the cDNA library was prepared in pools of 50,000 colony forming units (cfu) each. *E. coli* transformed with a cDNA library in the ΔkFGF7L signal trap vector were plated on 150 mm LB agar plates with 100 µg/ml ampicillin and incubated at 37° C. ovenight. About 50,000 colony forming units (cfu) from agar plates were pooled into 50 ml LB in a 250 ml flask. The bacteria were grown for 3 hours with agitation, and pelleted by centrifugation at 4000 rpm for 10 minutes in 50 ml conical tubes. Ten pools were prepared. Plasmid DNA was isolated from the pools using QIAGEN maxi prep.

Plasmid DNA was introduced into NIH 3T3 cells by the standard calcium phosphate transfection as previously described (Sambrook et at, supra). Briefly, 100 ng of each cDNA library pool was used to transfect about 200,000 cells in one 35 mm plate. After 24 hours, the cells from one 35 mm plate were split into five 100 mm plates and grown in normal medium for one day followed by low serum medium for 13 days. About 2500 colonies grew from transfected cells after the two week incubation in the selection medium. These colonies were then analyzed for novel genes that encoded secreted polypeptides as described below.

To each 100 mm tissue culture plate was added 2 ml of trypsin-EDTA followed by incubation at 37° for 5 minutes. Thecells in the colonies were released from the surface of the plate by gentle swirling. Cells were transferred to 50 ml conical tubes with 2 ml of FCS to stop the trypsin activity. Tubes were centrifiged at 1000 rpm for 5 minutes to pellet the cells. The supernatant was discarded.

Cells equal or less than 1 gram were lysed with 20 ml of TRIzol reagent (BRL), homogenized for 30 seconds, and extracted with 4 ml of chloroform. The tubes were centrifuged at 4000 rpm for 3( minutes and the aqueous phase was transferred to a new tube. RNA was precipitated by adding 10 ml isopropanol, mixing, and centrifuging, for 30 minutes at 4200 rpm. The RNA pellet was washed with 10 ml of 70% ethanol, dried briefly, and resuspended in 0.5 ml TE buffer. Total RNA from each of six experiments (approximately 15,000 NIH-3T3 colonies) was used to prepare polyA⁺ RNA using a commercially available mRNA purification kit (Dynal). The cDNA inserts of the plasmid transcripts were rescued by RI-PCR. A SuperScript preamplification system (BRL) was used to synthesize first strand cDNA. For each reaction representing one of six experiments, 1 µg polyA⁺ RNA, 1 µl (2 mM) vector-specific primer 1605-21 (SEQ ID NO: 2), and water were combined in a total volume of 12 µl.

1605-21 5'AATCCGATGCCCACGTTGCAGTA 3' SEQ ID NO: 2

The mixture was incubated at 70° C. for 10 minutes and transferred to 50° C. A premixture was prepared containing 2.0 µl 10×buffer, 2.0 µl of 25 mM MgCl$_2$, 1.0 µl 10 mM dNTPs, and 2.0 µl 0.1 M dithreitol was added. The reaction was started by the addition of 1.0 ml reverse transcriptase and incubated at 50° C. for one hour. The reaction was stopped by incubation at 70° C. for 15 minutes. The RNA was digested with 1 µl Rnase H at 37° C. for 20 minutes.

PCR was perfomied with Pfu polymerase (Perkin Elmer). In a total volume of 100 µl, 2 µl first strand reaction, 1×Pfu buffer, 0.4 µM each of primers 1239-08 (SEQ ID NO: 3) and 1605-22 (SEQ ID NO: 4), 0.2 mM dNTPs, 5% DMSO, and 1.0 µl Pfu polymerase were added.

1239-08: 5' AAAATCTTAGACCGACGACTGTGTTT 3' SEQ ID NO: 3

1605-22: 5' GAGTCTCCGCAGCCTTTTGAGG SEQ ID NO: 4

The sample was heated at 95° C. for 1 minute, and amplified for 30 cycles. Each cycle includes: 95° C. for 30 seconds, 66° C. for 45 seconds, 72° C. for 2 minutes. The reaction was incubated at 70° C. for 10 minutes at the end.

PCR DNA fragments were extracted once with phenol/chloroform (50/50) and ethanol precipitated. The DNA was then digested with NotI and SalI and small fragments and PCR primers were removed by using a QIAGEN PCR purification kit (QIAGEN). A signal trap library was constructed by ligating the DNA fragments into XhoI and Not I digested vector, pcDNA3.(-) containing the placental alkaline phosphatase gene. Each ligation included 10 ng PCR fragments, 50 ng vector, 1×ligase buffer, and 0.5 µl T4 DNA ligase in a total volume of 10 µl. The ligation was carried at 16° C. overnight. The ligated DNA was precipitated by adding 5 µl tRNA, 10 µl water, 12.5 µl 7.5 M NH$^4$AC, 70 µl ethanol (–20° C.), and centrifuged for 20 minutes. The pellet was washed with 0.5 ml 70% ethanol (–20° C.), and resuspended in 5 µl water. For each of the six ligation reactions, 8 µl was used to transform 100 µl of E. coli DH10B cells by electroporation. A total of 36 million cfu was obtained.

One clone, tmst2-00004-d1, was found to contain a 412 nucleotide insert (SEQ ID NO: 5) encoding the amino terminal 133 amino acids (SEQ ID NO: 6) of the full-length protein including the signal peptide.

EXAMPLE 2

DNA Encoding Full Length Mouse tmst2 Receptor

A cDNA encoding the full length mouse tmst2 receptor was constructed by combining two sequences. The first sequence was the original signal trap clone. The second sequence was obtained by screening a cDNA library from the bone marrow stromal cell line, using the 412 bp signal trap clone as a probe, following standard colony hybridization procedure (Sambrook el al.). The longest clone obtained from the screen encoded the full length protein except for the five amino terminal amino acids. The clone also included 16 nucleotides of 3' untranslated region (3' UTR) followed by a poly A stretch. An alternative downstream poly A addition signal was deduced from additional poly-adenylated 3' UTR sequence obtained by 3' RACE using a Marathon cDNA library from a seven day seven mouse embryo (Clontech). The full-length sequence (SEQ ID NO: 7) includes an open reading franme of 594 nucleotides encoding a primary translation product of 198 amino acids (SEQ ID NO: 8) having a predicted size of approximately 20 kD. The deduced protein sequence has a predicted amino terminal signal peptide and a carboxy terminal transmembrane domain followed by a dibasic stop transfer signal. Comparison of the deduced amino acid sequence (SEQ ID NO. 8) and predicted disulfide linkage structure of tmst2 with those of other members of the TNF-receptor gene family reveals that tmst2 is most closely related to ymkz5 (a novel UNF receptor cloned at Amgen), FAS and TNFR-1.

Alternative polyadenylation sites yield 3' UTR's of either 16 or 26 nucleotides. The longer 3' UTR harbors a repeated ATTT sequence. This motif has been implicated in RNA stability and translational control, suggesting that tmst2 expression may be under control of external stimuli. The 3' RACE clones also showed the existence of a splice variant (SEQ ID NO: 9) in which a 45 bp alternative exon is inserted between nucleotides 523 and 524 of the "transmembrane" full length sequence (SEQ ID NO: 7). The inserted sequence causes translational termination before the transmembrane domain and the resultingvariant protein (SEQ ID NO: 10) is predicted to be secreted.

EXAMPLE 3

Tissue Specific Expression of tmst2-Receptor

Tissue specific expression patterns of tmst2-receptor gene was investigated by Northern blot analysis and itn situ hybridization using a $^{32}$P-labeled PCR product as a probe to detect the presence of tmst2-receptor transcript in various tissues.

Cytoplasmic and poly-A$^+$ RNA were isolated from various cell lines and tissues using standard techniques [Sambrook, J. et al, Molecular Cloning, Cold Spring Harbor Laboratory Press, New York (1989)]. Cells/tissues were lysed with 20 ml of TRIzol reagent (BRL), homogenized for 30 seconds, and extracted with 4 ml of chloroform. The tubes were centrifuged at 4000 rpm for 30 minutes and the aqueous phase was transferred to a new tube. RNA was precipitated by adding 10 ml isopropanol, mixing, and centrifuging for 30 minutes at 4200 rpm. The RNA pellet was washed with 10 ml of 70% ethanol, dried briefly, and resuspended in 0.5 ml TE buffer. Poly A$^+$ RNA was prepared by using a commercially available mRNA purification kit (Dynal).

After elution of poly A$^+$ RNA from the column in 750 µl of TE buffer, the sample was then ethanol precipitated by adding 40 µl sample buffer and 1 ml ethanol at –70° C. overnight. Poly A$^+$ RNA was then fractionated using formaldehyde/agarose gel electrophioresis system as previously described and transferred. Following electrophoresis, the gel was processed and the .RNA transferred to a nylon membrane. See Sambrook et al. Supra. Commercially available RNA blots (Clontech) were also used. Northern blots were then prehybridized in 20 ml of prehybridization solution containing 5×SSPE, 50% fomarnide, 5×Denhardt's solution, 0.5% SDS and 100 mg/mil denatured salmon spenn DNA for 2–4 hours at 42° C. The blots were then hybridized in 20 ml of hybridization solution containing 6×SSPE, 50% formamide, 5×Denhardt's solution, 0.5% SDS, 100 µg/ml denatured salmon sperm DNA. Approximately 5 ng/ml of random primed, $^{32}$P-labeled (RadPrime Kit, GIBCO) tmst2-00004-d1 cDNA was used as a probe. The blots were hybridized for 18–24 hours at 42° C. The blots were then washed in 2×SSC, 0.1 % SDS at 42° C. The blots were then exposed to x-ray films for three days at 80° C.

Northern blot analysis revealed that tmst2 gene is expressed in early (7 day) embryo's, NIH-3T3 cells, and bone marrow stromal cells. Low level tmst2 transcripts were also detected in 7-day embryos, and in adult heart, lungs, small intestines and kidneys by in situ hybridization.

In situ hybridization analysis is carried out to detect the presence and distribution of mRNA in different tissues. Iz situ hybridization is carried out as previously described. See Sambrook et al., supra. Briefly, a panel of normal embryonic (E8.5 through E15.5) and adult mouse tissues are fixed in zinc-formalin fixative, embedded in paraffin, and sectioned to generate 5 μm thin sections. Following sectioning and prior to in situ hybridization, tissue sections were permeabilized with 0.2 M HCl, followed by digestion with Proteinasc K. The sections are acetylated with triethanolamine and acetic anhydride. Sections are hybridized overnight at 55° C. with a $^{32}$P-labeled riboprobe corresponding to the full length mouse cDNA that was generated using the standard protocols was for example pGEM vectors having RNA polyncrase transcription initiation sites. Excess probe is removed by RNase digestion followed by a series of washes in buffer with decreasing salt concentrations followed by a high stringent wash in 0.1×SSC at 55° C. The sections are then processed for autoradiography. The sections are dipped in Kodak NTB2 photographic emulsion, and kept a 4° C. for approximately 2–3 weeks. The sections are then developed and counterstained with hematoxilyn and eosin. Sections were examined using darkficld and transmitted light microscopy for tissue morphololy and hybridization signals.

EXAMPLE 4

Production of tmst2-Receptor Polypeptides

A. Expression of tmst2-Receptor Polypeptide in Bacteria

PCR may be used to amplify template DNA sequences encoding an tmst2-receptor polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary vector, such as pAMG21 containing the lux promoter and a gene encodingi kanamycin resistance is digested with BamHI and NdcI for directional cloning of inserted DNA. The ligated mixture is transformed into E. coli host strain 393 by electroporation and transformants selected for kanamycin resistance. Plasmid DNA from selected colonies is isolated and subjected to DNA sequencing to confirm the presence of the insert.

Transformed host cells are incubated in 2XYT medium containing 30 μg/ml kanamycin at 30° C. prior to induction. Gene expression can then be induced by addition of N-(3-oxohexanoyl)-d1-homoserine lactone to a final concentration of 30 ng/ml followed by incubation at either 30° C. or 37° C. for six hours. Expression of tmst2-receptor polypeptide is evaluated by centrifugation of the culture, resuspension and lysis of the bacterial pellets, and analysis of host cell proteins by SDS-polyacrylamide gel electrophoresis.

According to the protocol above, secreted tmst2 (SEQ ID NO: 10) was produced in E. coli. The purified protein of approximately 20 kD was then used for biological studies and antibody production.

Inclusion bodies containing tmst2-receptor polypeptide are purified as follows: Bacterial cells are pelleted by centrifugation and resuspended in water. The cell suspension is lysed by sonication and pelleted by centrifugation at 195,000×g for 5 to 10 minutes. The supernatant is discarded and the pellet washed and transferred to a homogenizer. The pellet is homo,enized in 5 ml. of a Percoll solution (75% liquid Percoll. 0.15 M NaCl) until uniformly suspended and then diluted and centrifuged at 21,600×g for 30 minutes. Gradient fractions containing the inclusion bodies are recovered and pooled. The isolated inclusion bodies are analyzed by SDS-PAGE.

B. Expression of tmst2-Receptor Polypeptide in Mammalian Cells

A cDNA fragment encoding the 171 amino terminal residues of tmst2 was prepared using PCR. Briefly, the tmst2 cDNA region was amplified using primers 2086'-39 and 2086-41 corresponding to the 5' and 3'-ends of the cDNA.

2086-39 CATACTAGTTCCACCATGTTTGGCTTCT-TCTGCAGCTTGGT SEQ ID NO: 11

2086-41 TTGTCGACATTTGAAACAGATGAACTG-CACACA SEQ ID NO: 12

The resulting fragment was digested with SpeI and Sal I, and ligated into the XbaI and SalI sites of pDSRaFc plasmid vector containing a DNA insert encoding the human Fc region. The resulting fusion gene was confirmed by DNA sequencing (SEQ ID NO: 13). The deduced amino acid sequence of the tmst2-Fc fusion protein is set out in SEQ ID NO: 14.

The expression constrict was transfected into CHOD-AM1 cells by calcium phosphate method as previously described (Ausubel et al., *Curr. Prot. Mol. Biol.* 1, 9.11–9.13, 1994) and transfected cells were selected in dialyzed serum in the absence of HT supplement. Individual colonies were expanded and conditioned medium was tested for fusion protein production by Western analysis. A 55 kD band representing the fusion protein was observed at varying levels. One clone producing approximately I mg of Fc-fusion protein per liter was adapted to suspension growth and used for large-scale production.

EXAMPLE 5

Production of Anti-tmst2-receptor Antibodies

Antibodies to tmst2-receptor polypeptides may be obtained by immunization with purified protein or with tmst2-receptor peptides produced by biological or chemical synthesis. Substantially pure tmst2 protein or polypeptide may be isolated from trans fcted cells as described in Example 4. Concentration of protein in the final preparation may be adjusted, for example, by concentration oni an amicon filter device, to the level of a few micrograms/ml. Monoclonal or polyclonal antibodies to the protein can then be prepared by any of the procedures known in the art for generating antibodies such as those described in Hudson and Bay, "Practical Immunology, Second Edition", Blackwell Scientific Publications.

A. Anti-tmst2-receptor Monoclonal Antibody Production

Monoclonal antibody to epitope of any of the peptides identified and isolated as described can be prepared from murine hybridomas according to the classical method of Kohler, G. and Milstein, C., *Nature* 256:495 (1975) or derivative methods thereof. Briefly, a mouse is repetitively inoculated with a few micrograms of the selected protein over a period of a few weeks. The mouse is then sacrificed, and the antibody producing cells of the spleen isolated. The spleen cells are fused by means of polyethylene glycol with mouse myeloma cells such as NS-1 cells, and the excess unfused cells destroyed by growth of the system on selective media comprising hypoxanthine; aminopterin; thynidine (HAT media). The successfully fused cells are diluted and aliquots of the dilution placed in wells of a microtiter plate where growth of the culture is continued. After selection, tissue culture supernatants are taken from each fusion well and tested for tmst2-receptor antibody production by EIA. Selected positive clones can be expanded and their monoclonal antibody product harvested for use. Detailed procedures for monoclonal antibody production are described in Davis, L. et al. *Basic Methods in Molecular Biology, Section 21-2*, Elsevier, New York, N.Y.

B. Polyclonal Anti-tmst2 Receptor Antibody Production

Polyclonal antiserum containing antibodies to heterogenous epitopes of a single protein can be prepared by immunizing suitable animals with the expressed protein described above, which can be unmodified or modified to enhance immunogenicity. Effective polyclonal antibody production is affected by many factors related both to the antigen and the host species. For example, small molecules tend to be less immunogenic than large molecules and may require the use of carriers or adjuvants. Also, lost animals vary in response to site of inoculations and dose, with both inadequate or excessive doses of antigen resulting in low titer antisera. Small doses (ng levels) of antigen administered at multiple intradermal sites appear to be most reliable. An effective immunization protocol for rabbits can be found in Vaitukaitis, J. et al. *J. Clin. Endocrinol. Metab.* 33: 988–991 (1971).

Booster injections can be given at regrular intervals, and antiserum harvested when antibody titer thereof as determined semi-quantitativcly, (or example, by double immunodiffosion in agar against known concentrations of the antigen, begin to fall. See, for example, Ouchterlony, O. et al., Chap. 19 in: *Handbook of Experimental Immunology* ed. D. Weir, Blackwell (1973). Plateau concentration of antibody is usually in the range of 0.1 to 0.2 mg/ml of serim (about 12 um). Affinity of the antisera for the antigen is determined by preparing competitive binding curves, as described, for example, by Fisher, D., Chapt. 42 in; *Manual of Clinical Immunology*, 2d Ed. (Rose and Friedman, eds.) Amer. Soc. For Microbiol., Washington, D.C. (1980).

Three rabbits were immunized with tmst2 protein produced in *E. coli*. Test bleeds show that the serum of all rabbits will immunoprecipitate the tmst2 protein as well as detect it on Western blots.

Alteniative procedures for obtaining anti-tmst2-receptor antibodies may also bc employed, such as immunization of transgenic mice harboring human Ig loci for production of fully human antibodies, and screening of synthetic antibody libraries, such as those generated by mutagenesis of an antibody variable domain.

EXAMPLE 6

Biological Activity of tmst2-Receptor Polypeptide

Secreted tmst2 receptor (SEQ ID NO. 10) was expressed in *E.coli* as described above and tested in vitro for the ability to bild to and neutralize the activity of members of the TNF-related ligand family.

At 10 mg/ml and 100 mg/ml, secreted murine tmst2 blocked apoptosis in Jurkat cells induced by murine TRAIL protein. However, secreted murine tmst2 failed to block apoptosis in Jurkat cells when induced by either human TRAIL or by human FAS ligand. These results indicate that secreted murine tmst2 is biologically active and may be involved in regulating the activity of members of the TNF family including 1TRAIL.

EXAMPLE 7

Functional Analysis of the Role of tmst2-Receptor

To determine the functional role of tmst2 in vivo, the tmst2 gene is either over expressed in the germ line of animals or inactivated in the germ line to mammals by homologous recombination. Animals in which the gene is over expressed under the regulatory control of exogenous or endogenous promoter elements are known as transgenic animals. Animals in which an endogenous gene has been inactivated by homologous recombination are also known as "knockout" animals. Exemplary mammals include rabbits and rodent species such as mice.

Transgenic animals allow for the determination of the effect(s) of over expression or inappropriate expression of the tmst2-receptor on development and disease processes. tmst2-receptor-receptor transglenic animals can also serve as a model system to test compounds that can modulate receptor activity.

The "knockout" animals allow for the determination of the role of tmst2 in embryonic development, and in immune and proliferative responses. The role of tmst2 in development, and in immune and proliferative response is determined by analysis the effect(s) of gene knockout on the development of the embryo as well as on the development and differentiation of various organs and tissues such as the immune system in these animals. (as determined by FACS analysis ofcell populations at different stages of development).

In addition to tmst2 "knockout" mammals, double and triple "knockout" of tmst2 and one or two related genes are contemplated.

EXAMPLE 8 tmst2-receptor-Related Genes

Southern analysis of mouse genomic DNA was carried out using standard hybridization conditions and final washes at 0.1×SSC, 0.1% SDS at 42° C. After digestion with each of the following enzyines: EcoRI, BamHI, PstI, HindIII and EcoRV, three restriction fragments were shown to hybridize to a tmst2 cDNA probe. This observation suggested the existence of one or more genes related to tmst2, and the EcoRI fragments of 7.5, 6.0 and 4.5 kB were cloned in a bacteriophage 1 vector. The cloned genomic sequences related to tmst2 are used to identify human homologs.

EXAMPLE 9

Binding Analysis of TNF Ligand Family Members with tmst2-Receptor

Binding studies were performed to determine if various TNF ligand family members are ligands for the tmst2-receptor. The only TNF ligand which bound to the tmst2-receptor was murine TRAIL. The binding studies, based on surface plasmon resonance, were carried out with the automated, high throughput Biacore 2000 system at 25° C. according to the manufacturer's instructions (Biacore, Uppsula, Sweden) as follows:

The receptor was immobilized on a CM5 research grade amine coupling chip (Biacore) by placing 40 µg/ml of recombinant tmst-2 receptor diluted in HEPES buffered saline (HBS-P; Biacore) at pH 4.5 on the chip. The ligands were diluted in HBS-P buffer containing 10 µg/ml BSA and 4 mg/ml dextran to block nonspecific binding sites. The ligand samples were injected over the receptors at concentrations ranging from 2 nM to 100 nM. The chips were regenerated between ligand injections by washing 2 times for 3 minutes in 25 mM CAPS, 1 M NaCl pH 10.5.

The TNF ligands tested were: human nag TRAIL,(amino acids 95–281; Genbank accession no. AAC50332), murine nag TRAIL (amino acids 99–29, Genbank accession no. NP 033451), murine Fc TRAIL, human OPGL ligand (amino acids 159–318), murine OPGL ligand (amino acids 159–316) human TNFα (amino acids 82–233, Genbank accession no. CAA26669), murine TNFα (amino acids 82–233, Genbank accession no. CAA68530). The extracellular and transmembrane portions of the ligands were recombinantly expressed in *E.coli*. Specifically, the denoted amino acids for each ligand indicate the portion of the ligand expressed recombinantly. Additionally, commercially available human Fas ligand (Alexis Biochemicals, San Diego, Calif.) was also tested. Human DR5Fc, a known TRAIL receptor, was used as a control.

Results of the assay were determined by detecting the change in mass on the chip as measured by changes in light absorption on the chip indicated as resonance units. The tmst2-receptor only bound to muriine TRAIL, which was bioactive in cell culture assays. The species specific binding suggests that tmst2 polypeptide may function as a TRAIL decoy receptor.

Similar species specific bindings to TRAIL was demonstrated for ynkz5, a novel transmembrane TNF receptor. cloned by Amgen, which is closely linked to tmst2 in the murine genome. Primary sequences homology comparisons indicate that both tmst2 and ymkz5 are most closely related to FAS and TNFR-1 which are not functionally similar. Therefore, the characterization of the murine genes, tmst2 and ymkz5, may aid in the discovery of human TRAIL decoy receptors based on functionality and not solely based on primary sequence homology.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. An isolated nucleic acid molecule comprising a nucleotide sequence selected from the group consisting of:
   (a) the nucleotide sequence as set forth in SEQ ID NOS: 7 or 9;
   (b) a nucleotide sequence encoding the polypeptide as set forth in SEQ ID NOS: 8 or 10;
   (c) a nucleotide sequence complementary to (a) or (b).

2. A vector comprising the nucleic acid molecule of claim 1.

3. A host cell comprising the vector of claim 2.

4. The host cell of claimed that is a eukaryotic cell.

5. The host cell of claim 3 that is a prokaryotic cell.

6. A process of producing a tmst2-receptor polypeptide comprising culturing the host cell of claim 3 under suitable conditions to express the polypeptide, and optionally isolating the polypeptide from the culture.

7. The process of claim 6 wherein the nucleic acid molecule comprises promoter DNA other than the promoter DNA for the native tmst2-receptor polypeptide operatively linked to the DNA encoding the tmst2-receptor polypeptide.

8. A composition comprising a nucleic acid molecule of claim 1 and a carrier.

9. A composition of claim 8 wherein said nucleic acid molecule is contained in a viral vector.

10. A viral vector comprising a nucleic acid molecule of claim 1.

11. An isolated nucleic acid molecule comprising a nucleic acid sequence that is at least 92% identical to the sequence of the nucleic acid molecule of claim 1 and encodes a polypeptide that is capable of binding TNF ligand TRAIL.

12. An isolated nucleic acid molecule comprising a nucleic acid sequence that is at least 92% identical to the nucleic acid mnolecule of claim 1 and encodes a polypeptide that inhibits apoptosis.

13. An isolated nucleic acid molecule that encodes a polypeptide that is capable of binding TNF ligand TRAIL and hybridizes to the complement of the nucleic acid molecule of claim 1 under the following stringent conditions: a final wash of 0.015 M sodium chloride and 0.0015 M sodium citrate at 65–68° C.

14. An isolated nucleic acid molecule that encodes a polypeptide that inhibits apoptosis and hybridizes to the complement of the nucleic acid molecule of claim 1 under the following stringent conditions: a final wash of 0.015 M sodium chloride and 0.0015 M sodium citrate at 65–68° C.

15. An isolated polynucleotide comprising a nucleic acid sequence that is at least 92% identical to the sequence of the nucleic acid molecule of claim 1 and encodes a polypeptide that is a TNF-receptor family nmber capable of binding TRAIL.

16. An isolated nucleic acid molecule that encodes a polypeptide that is a TNF-receptor family member capable of binding TRAIL and hybridizes to the complement of the nucleic acid molecule of claim 1 under the following stringent conditions: a final wash of 0.015 M sodium chloride and 0.0015 M sodium citrate at 65–68° C.

17. A fusion polypeptide comprising an amino acid sequence encoded by the nucleic acid sequence of any one of claims 1, 11, 12, 13, 14, 15, and 16, fused to a heterologous amino acid sequence.

18. The fusion polypeptide of claim 17 wherein the heterologous amino acid sequence is an IgG constant domain or fragment thereof.

19. A diagnostic reagent comprising a nucleic acid molecule of any one of claims 1, 11, 12, 13, 14, 15, and 16, wherein the nucleic acid molecule is detectably labeled.

20. A diagnostic reagent comprising a polynucleotide that is detectably labeled and is complementary to a nucleic acid molecule according to any one of claims 1, 11, 12, 13, 14, 15, and 16.

* * * * *

UNITED STATES PATENT AND TRADEMARK OFFICE
CERTIFICATE OF CORRECTION

PATENT NO. : 6,627,199 B1
DATED : September 30, 2003
INVENTOR(S) : Chris Saris

It is certified that error appears in the above-identified patent and that said Letters Patent is hereby corrected as shown below:

Title page,
Item [57], ABSTRACT, delete "receptor", and insert -- receptor --.

Column 1,
Line 15, delete "super genie", and insert -- supergene --.

Column 3,
Line 4, delete "B-lynphocyte", and insert -- B-lymphocyte --.

Column 8,
Line 42, delete "7-methylguaninic", and insert -- 7-methylguanine --.
Line 43, delete "5-metihoxyamino-methyl-2-thiouracil", and insert
-- 5methoxyamino-methyl-2-thiouracil --.

Column 9,
Line 15, delete "introni", and insert -- intron --.
Line 45, delete "fonnulation", and insert -- formulation --.

Column 10,
Line 3, delete "Gralham", and insert -- Graham --.
Line 12, delete "transfonned", and insert -- transformed --.

Column 11,
Line 58, delete "receptor", and insert -- receptor --.
Line 65, delete "polypeptidc", and insert -- polypeptide --.

Column 12,
Line 17, delete "ortholog,s", and insert -- orthologs --.
Line 44, delete "tenn", and insert -- term --.
Line 45, delete "teni", and insert -- term --.

Column 13,
Line 13, delete "T herefore,", and insert -- Therefore, --.
Line 15, delete "twvo", and insert -- two --.
Line 36, delete 1st reference to "used,".

Column 14,
Line 11, delete 1st reference to ""moderatety-stfngent"".

UNITED STATES PATENT AND TRADEMARK OFFICE
CERTIFICATE OF CORRECTION

PATENT NO. : 6,627,199 B1
DATED : September 30, 2003
INVENTOR(S) : Chris Saris

It is certified that error appears in the above-identified patent and that said Letters Patent is hereby corrected as shown below:

Column 16,
Line 35, delete deteniine", and insert -- determine --.

Column 17,
Line 23, delete "luither", and insert -- further --.
Line 48, delete "thireading", and insert -- threading --.
Line 63, delete "vlwhercin", and insert -- wherein --.

Column 18,
Line 5, delete "occurting)", and insert -- occurring) --.
Line 43, delete "Lisin", and insert -- using --.

Column 19,
Line 41, delete "mutltimerization", and insert -- multimerization --.

Column 20,
Line 18, delete "Usitig", and insert -- using --.
Lines 32-33, delete "Proteint Sequtence", and insert -- Protein Sequence --.

Column 21,
Line 26, delete "gYenerally,", and insert -- generally, --.
Line 40, delete "infornation", and insert -- information --.
Line 40, delete "fromt", and insert -- from --.

Column 22,
Line 10, delete "influenicing", and insert -- influencing --.
Line 33, delete "fonn", and insert -- form --.

Column 23,
Line 13, delete "polyierase", and insert -- polymerase --.
Line 33, delete "lengtth", and insert -- length --.
Line 39, delete "methionilne", and insert -- methionine --.

Column 24,
Line 12, delete "glycosylationi", and insert -- glycosylation --.
Line 61, delete "althougLh", and insert -- although --.

UNITED STATES PATENT AND TRADEMARK OFFICE
CERTIFICATE OF CORRECTION

PATENT NO. : 6,627,199 B1
DATED : September 30, 2003
INVENTOR(S) : Chris Saris

It is certified that error appears in the above-identified patent and that said Letters Patent is hereby corrected as shown below:

Column 25,
Line 6, delete "eukarvotic", and insert -- eukaryotic --.
Line 8, delete "sequneces", and insert -- sequences --.
Line 22, delete "endogenoLs", and insert -- endogenous --.

Column 26,
Line 18, delete "g,enes", and insert -- genes --.
Line 25, delete "thymidile", and insert -- thymidine --.
Line 27, delete "tranisformants", and insert -- transformants --.
Line 32, delete "thes", and insert -- the --.
Line 55, delete "heterologotis", and insert -- heterologous --.

Column 27,
Line 40, delete "tmst2-reccptor uene,", and insert -- tmst2-receptor gene, --.

Column 28,
Line 14, delete "reccptor", and insert -- receptor --.

Column 30,
Line 20, delete "case", and insert -- ease --.
Line 35, delete "CLO-K1", and insert -- CHO-K1 --.
Line 67, delete "procaiyotic", and insert -- procaryotic --.

Column 31,
Line 2, delete "Pseudoinonas", and insert -- Pseudomonas --.
Line 2, delete "Set Tatia", and insert -- Serratia --..
Line 13, delete "Pseudomonia", and insert -- Pseudomonas --.
Line 45, delete "replicaitioni", and insert -- replication --.

Column 32,
Line 47, delete "r.,", and insert -- T., --.
Line 55, delete "Sixyth", and insert -- Sixth --.

Column 33,
Line 2, delete "othfie", and insert -- of the --.
Line 33, delete "Sacciharomyces", and insert -- Saccharomyces --.
Line 66, delete "lor", and insert -- for --.

UNITED STATES PATENT AND TRADEMARK OFFICE
CERTIFICATE OF CORRECTION

PATENT NO. : 6,627,199 B1
DATED : September 30, 2003
INVENTOR(S) : Chris Saris

It is certified that error appears in the above-identified patent and that said Letters Patent is hereby corrected as shown below:

Column 34,
Line 13, delete "SLutable", and insert -- Suitable --.
Line 26, delete "transfonned.", and insert -- transformed. --.
Line 39, delete "foulid", and insert -- found --.
Line 42, delete "eukaiyotic", and insert -- eukaryotic --.
Line 54, delete "tecmiques", and insert -- techniques --.

Column 35,
Line 47, delete "Solubilizationi.", and insert -- solubilization. --.
Line 48, delete "refolding/oxidatioln", and insert -- refolding/oxidation --.
Line 51, delete "shufflin(g", and insert -- shuffling --.
Line 53, delete "gilutathione", and insert -- glutathione --.
Lines 54-55, delete "ditliothretol(DTT)?ditlianie", and insert -- dithiothreitol(DTT)/ dithiane --.

Column 39,
Line 2, delete "and/oor", and insert -- and/or --.
Line 11, delete "N-liniked", and insert -- N-linked --.
Line 24, delete "stnlcture", and insert -- structure --.
Line 40, delete "stricture.", and insert -- structure --.
Line 46, delete "strmcture-function", and insert -- structure-function --.
Line 57, delete "infonnation", and insert -- information --.

Column 40,
Line 58, delete "N-temiinus", and insert -- N-terminus --.

Column 41,
Line 16, delete "N-teniinus", and insert -- N-terminus --.
Line 35, delete "vitto", and insert -- vitro --.
Line 37, delete "crzde", and insert -- crude --.
Line 44, delete "carboxyiethyl", and insert -- ca rboxymethyl --.
Line 45, delete "carbocyamidomiiethyol", and insert -- carbocyamidomethyl --.
Line 46, delete "bromotri fLuoroacetonic", and insert -- bromotrifluoroacetone --.
Line 48, delete "N-alkylmalcimides", and insert -- N-alkylmaleimides --.

Column 42,
Line 33, delete "maleimnides", and insert -- maleimides --.
Line 52, delete "find", and insert -- and --.
Line 65, delete "Fhe", and insert -- The --.
Line 66, delete "Icluided", and insert -- Included --.

UNITED STATES PATENT AND TRADEMARK OFFICE
CERTIFICATE OF CORRECTION

PATENT NO. : 6,627,199 B1
DATED : September 30, 2003
INVENTOR(S) : Chris Saris

It is certified that error appears in the above-identified patent and that said Letters Patent is hereby corrected as shown below:

Column 43,
Line 18, delete "carnied", and insert -- carried --.
Line 43, delete "non-anttigenic", and insert -- non-antigenic --.
Line 46, delete "(ethyene", and insert -- (ethylene --.
Line 47, delete "Theraeutic", and insert -- Therapeutic --.
Line 48, delete "Clycol", and insert -- Glycol --.
Line 66, delete "(MW 3,4000)", and insert -- (MW 3,400) --.

Column 44,
Line 26, delete "cotjugatedc", and insert -- conjugated --.
Line 28, delete "avid in ibiotin/tmst2", and insert -- avid in/biotin/tmst2 --.
Lines 59-60, delete "fragmcnts", and insert -- fragments --.

Column 45,
Line 7, delete "immrunized", and insert -- immunized --.
Line 20, delete "Atitibody", and insert -- Antibody --.
Line 48, delete "determiniing", and insert -- determining --.
Line 63, delete "immtnoglobulin", and insert -- immunoglobulin --.

Column 46,
Line 52, delete "puri Fied", and insert -- purified --.

Column 47,
Line 36, delete "or", and insert -- of --.
Line 53, delete "plhosphatase", and insert -- phosphatase --.

Column 48,
Line 11, delete "diaginostic", and insert -- diagnostic --.
Line 45, delete "immunofluorscenice", and insert -- immunofluorescence --.

Column 49,
Line 24, delete "enzyines", and insert -- enzymes --.

Column 50,
Line 4, delete "abnonnal", and insert -- abnormal --.

Column 51,
Line 38, delete "primiers", and insert -- primers --.

UNITED STATES PATENT AND TRADEMARK OFFICE
CERTIFICATE OF CORRECTION

PATENT NO. : 6,627,199 B1
DATED : September 30, 2003
INVENTOR(S) : Chris Saris

It is certified that error appears in the above-identified patent and that said Letters Patent is hereby corrected as shown below:

Column 52,
Line 23, delete "geties", and insert -- genes --.
Line 29, delete "fonnation", and insert -- formation --.
Line 30, delete "miNIA", and insert -- mRNA --.

Column 54,
Line 56, delete "chclates", and insert -- chelates --.
Line 56, delete "(Ru2$^-$)", and insert -- (Ru2$^+$) --.
Line 60, delete "withi", and insert -- with --.

Column 55,
Line 61, delete "centriftigation", and insert -- centrifugation --.

Column 56,
Line 31, delete "formatioll", and insert -- formation --.
Line 42, delete "polypeptidc", and insert -- polypeptide --.

Column 57,
Line 45, delete "celi", and insert -- cell --.
Line 58, delete "adenovirtlis", and insert -- adenovirus --.

Column 59,
Line 1, delete "deterniine", and insert -- determine --.
Line 2, delete "deteniine", and insert -- determine --.
Line 30, delete "cachcxia", and insert -- cachexia --.
Line 36, delete "syndromiie", and insert -- syndrome --.
Line 50, delete "and/cr", and insert -- and/or --.
Line 55, delete "deliverv", and insert -- delivery --.
Line 67, delete "usinty", and insert -- using --.

Column 60,
Line 24, delete "phaniaceutically", and insert -- pharmaceutically --.
Line 33, delete "fom", and insert -- form --.
Line 38, delete "Trsi-HC1", and insert -- Tris-HC1 --.
Line 56, delete "ol", and insert -- of --.
Line 58, delete "detenninilln", and insert -- determining --.
Line 63, delete "thei", and insert -- the --.

UNITED STATES PATENT AND TRADEMARK OFFICE
CERTIFICATE OF CORRECTION

PATENT NO. : 6,627,199 B1
DATED : September 30, 2003
INVENTOR(S) : Chris Saris

It is certified that error appears in the above-identified patent and that said Letters Patent is hereby corrected as shown below:

Column 61,
Line 3, delete "vivi", and insert -- vivo --.
Line 38, delete "pharmaceutical", and insert -- pharmaceutical --.
Line 41, delete "fonrulations", and insert -- formulations --.
Line 42, delete "usc", and insert -- use --.
Line 52, delete "fonnulations", and insert -- formulations --.

Column 62,
Line 12, delete "injections", and insert -- injection --.
Line 12, delete "Ilyaluronic", and insert -- Hyaluronic --.
Line 43, delete "fonnulated", and insert -- formulated --.
Line 50, delete "deleivery", and insert -- delivery --.
Line 59, delete "degrad(ation", and insert -- degradation --.
Line 64, delete "pharmaceutical", and insert -- pharmaceutical --.

Column 63,
Line 7, delete "phanracCutical", and insert -- pharmaceutical --.
Lines 10 and 24-25, delete "formulations", and insert -- formulations --.
Line 34, delete "ofdosin(g", and insert -- of dosing --.
Line 36, delete "fonnulation", and insert -- formulation --.
Line 64, delete "ptilmonary", and insert -- pulmonary --.

Column 64,
Lines 23 and 24, delete "formed", and insert -- formed --.
Line 39, delete "(1985)1;", and insert -- (1985)]; --.
Line 43, delete "phannaceutical", and insert -- pharmaceutical --.
Line 56, delete "implalltinlo", and insert -- implanting --.

Column 65,
Line 36, delete "gyene", and insert -- gene --.
Line 55, delete "genoine", and insert -- genome --.

Column 66,
Line 9, delete "throLugh", and insert -- through --.
Line 49, delete "noirnally", and insert -- normally --.

Column 67,
Lines 8 and 25, delete "Saner", and insert -- Sauer --.
Line 24, delete "sluprci", and insert -- supra --.
Line 34, delete "mariner", and insert -- manner --.
Lines 37-38, delete "occulTing", and insert -- occurring --.

UNITED STATES PATENT AND TRADEMARK OFFICE
CERTIFICATE OF CORRECTION

PATENT NO.     : 6,627,199 B1
DATED          : September 30, 2003
INVENTOR(S)    : Chris Saris It is certified that error appears in the above-identified patent and that said Letters Patent is hereby corrected as shown below:

Column 68,
Line 8, delete "nuclCeotides", and insert -- nucleotides --.
Line 10, delete "Geiie", and insert -- Gene --.
Line 60, delete "(it.", and insert -- al. --.

Column 69,
Line 40, delete "transfonined", and insert -- transformed --.
Line 42, delete "cell-specitic", and insert -- cell-specific --.
Line 42, delete "targetsin", and insert -- targeting --.
Line 49, delete "contianing", and insert -- containing --.
Line 50, delete "deleivery", and insert -- delivery --.

Column 70,
Line 27, delete "fniit", and insert -- fruit --.

Column 71,
Line 9, delete "er vivo", and insert -- ex vivo --.
Line 35, delete "ccil", and insert -- cell --.
Line 37, delete "clement(s)", and insert -- element(s) --.

Column 72,
Line 11, delete "seyncnt", and insert -- segment --.
Line 14, delete "genornic", and insert -- genomic --.
Line 15, delete "recoinbination", and insert -- recombination --.
Line 18 delete "endogenotis", and insert -- endogenous --.
Line 22, delete "whlilch hanvC", and insert -- which have --.
Line 23, delete "reccptor", and insert -- receptor --.
Line 29, delete "Antisence", and insert -- Antisense --.
Line 29, delete "infomiation", and insert -- information --.
Line 54, delete "tmst2-i-eceptor", and insert -- tmst2-receptor --.

Column 73,
Line 23, delete "enzyiatic", and insert -- enzymatic --.

Column 74,
Line 5, delete "fragmients", and insert -- fragments --.
Line 15, delete "orow", and insert -- grow --.
Line 50, delete "3(", and insert -- 30 --.
Line 59, delete "RI-PCR", and insert -- RT-PCRt --.

UNITED STATES PATENT AND TRADEMARK OFFICE
CERTIFICATE OF CORRECTION

PATENT NO. : 6,627,199 B1
DATED : September 30, 2003
INVENTOR(S) : Chris Saris

It is certified that error appears in the above-identified patent and that said Letters Patent is hereby corrected as shown below:

Column 75,
Line 8, delete "performied", and insert -- performed --.
Line 33, delete "$NH^4$ AC,", and insert -- $NH_4$ AC, --.

Column 76,
Line 4, delete "UNF", and insert -- TNF --.
Line 24, delete "itn", and insert -- in --.
Line 46, delete "electrophioresis", and insert -- electrophoresis --.
Line 52, delete "fomarnide", and insert -- formamide --.
Line 53, delete "spenn", and insert -- sperm --.

Column 77,
Line 2, delete "Iz", and insert -- In --.
Lines 9-10, delete "Proteinasc K", and insert -- Proteinase K --.
Line 11, delete "$^{32}$P-labelcd", and insert -- $^{32}$P-labeled --.
Line 14, delete "polyncrase", and insert -- polymerase --.
Line 22 delete "darkficld", and insert -- darkfield --.
Line 23, delete "morphololy", and insert -- morphology --.
Line 37, delete "Ndcl", and insert -- Ndel --.
Line 62, delete "homo,enized", and insert -- homogenized --.

Column 78,
Line 18, delete "constrict", and insert -- construct --.
Line 36, delete "trans fcted", and insert -- transfected --.
Line 38, delete "oni", and insert -- on --.
Line 57, delete "thynidine", and insert -- thymidine --.

Column 79,
Line 10, delete "lost", and insert -- host --.
Line 18, delete "regrular", and insert -- regular --.
Line 20, delete "semi-quantitativcly", and insert -- semi-quantitatively --.
Line 20, delete "(or", and insert -- for --.
Lines 20-21, delete "immunodiffosion", and insert -- immunodiffusion --.
Line 35, delete "Alteniative", and insert -- Alternative --.
Line 41, delete "bild", and insert -- bind --.
Line 56, delete "1TRAIL", and insert--TRAIL --.

Column 80,
Line 8, delete "transglenic", and insert -- transgenic --.
Line 32, delete "enzyines", and insert -- enzymes --.
Lines 62 and 64, delete "nag", and insert -- flag --.

UNITED STATES PATENT AND TRADEMARK OFFICE
CERTIFICATE OF CORRECTION

PATENT NO. : 6,627,199 B1
DATED : September 30, 2003
INVENTOR(S) : Chris Saris

It is certified that error appears in the above-identified patent and that said Letters Patent is hereby corrected as shown below:

Column 82,
Line 2, delete "ynkz5", and insert -- ymkz5 --.
Line 2, delete "transmembranc", and insert -- transmembrane --.

Column 97,
Line 34, delete "claimed that", and insert -- claim 3 --.
Line 58, delete "mnolecule", and insert -- molecule --.

Column 98,
Line 36, delete "nmber", and insert -- member --.
Line 53, delete "nucleic acid molecule", and insert -- polynucleotide --.

Signed and Sealed this

Twenty-first Day of September, 2004

JON W. DUDAS
*Director of the United States Patent and Trademark Office*

SEQUENCE LISTING

```
<160> NUMBER OF SEQ ID NOS: 15

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: (25)..(33)
<223> OTHER INFORMATION: N = A or T or G  or C
<223> OTHER INFORMATION: Primer 1360-38

<400> SEQUENCE: 1
ggaaggaaaa aagcggccgc aacannnnnn nnn                                   33

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: primer
<223> OTHER INFORMATION: Primer 1605-21

<400> SEQUENCE: 2
aatccgatgc ccacgttgca gta                                              23

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: primer
<223> OTHER INFORMATION: Primer 1239-08

<400> SEQUENCE: 3
aaaatcttag accgacgact gtgttt                                           26

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: primer
<223> OTHER INFORMATION: Primer 1605-22

<400> SEQUENCE: 4
gagtctccgc agccttttga gg                                               22
```

-continued

```
<210> SEQ ID NO 5
<211> LENGTH: 412
<212> TYPE: DNA
<213> ORGANISM: Mus musculus
<220> FEATURE:
<221> NAME/KEY: CDS
<222> LOCATION: (13)..(411)
<223> OTHER INFORMATION: tmst2 00004-d1

<400> SEQUENCE: 5
ttgcactcgg cc atg ttt ggc ttc ttc tgc agc ttg gtg tcc agt ctg agt        51
              Met Phe Gly Phe Phe Cys Ser Leu Val Ser Ser Leu Ser
                1               5                  10 cgc tgg ttc ctt tgg cgg cgg ctg ctg ctg ctg ctg ctg ctg ctg              99
Arg Trp Phe Leu Trp Arg Arg Leu Leu Leu Leu Leu Leu Leu Leu
 15                  20                  25 ctg aat ctg ccc ttg cag gta aaa ttt gct atg cta gaa tta cac tcc         147
Leu Asn Leu Pro Leu Gln Val Lys Phe Ala Met Leu Glu Leu His Ser
 30                  35                  40                  45 ttc aaa tgt ccc gct ggt gaa tac tgg tct aaa gac gtc tgt tgc aag         195
Phe Lys Cys Pro Ala Gly Glu Tyr Trp Ser Lys Asp Val Cys Cys Lys
                 50                  55                  60 aac tgt tct gca ggt aca ttt gtc aag gcg ccc tgc gaa atc ccc cat         243
Asn Cys Ser Ala Gly Thr Phe Val Lys Ala Pro Cys Glu Ile Pro His
 65                  70                  75 act caa gga caa tgt gag aag tgt cac cca gga aca ttc aca gag aaa         291
Thr Gln Gly Gln Cys Glu Lys Cys His Pro Gly Thr Phe Thr Glu Lys
         80                  85                  90 gat aat tac ctg gat gct tgt ata ctt tgc tcc acc tgt gat aaa gat         339
Asp Asn Tyr Leu Asp Ala Cys Ile Leu Cys Ser Thr Cys Asp Lys Asp
 95                  100                 105 cag gaa atg gtg gcc gac tgc tca gcc acc agt gac cgg aaa tgc cag         387
Gln Glu Met Val Ala Asp Cys Ser Ala Thr Ser Asp Arg Lys Cys Gln
110                 115                 120                 125 tgc cga aca ggt ctt tac tac tat g                                       412
Cys Arg Thr Gly Leu Tyr Tyr Tyr
                130

<210> SEQ ID NO 6
<211> LENGTH: 133
<212> TYPE: PRT
<213> ORGANISM: Mus musculus

<400> SEQUENCE: 6

Met Phe Gly Phe Phe Cys Ser Leu Val Ser Ser Leu Ser Arg Trp Phe
  1               5                  10                  15

Leu Trp Arg Arg Leu Leu Leu Leu Leu Leu Leu Leu Asn Leu
             20                  25                  30

Pro Leu Gln Val Lys Phe Ala Met Leu Glu Leu His Ser Phe Lys Cys
         35                  40                  45

Pro Ala Gly Glu Tyr Trp Ser Lys Asp Val Cys Cys Lys Asn Cys Ser
     50                  55                  60

Ala Gly Thr Phe Val Lys Ala Pro Cys Glu Ile Pro His Thr Gln Gly
 65                  70                  75                  80

Gln Cys Glu Lys Cys His Pro Gly Thr Phe Thr Glu Lys Asp Asn Tyr
             85                  90                  95

Leu Asp Ala Cys Ile Leu Cys Ser Thr Cys Asp Lys Asp Gln Glu Met
         100                 105                 110

Val Ala Asp Cys Ser Ala Thr Ser Asp Arg Lys Cys Gln Cys Arg Thr
```

```
              115                 120                 125
Gly Leu Tyr Tyr Tyr
    130

<210> SEQ ID NO 7
<211> LENGTH: 1550
<212> TYPE: DNA
<213> ORGANISM: Mus musculus
<220> FEATURE:
<221> NAME/KEY: CDS
<222> LOCATION: (13)..(606)
<223> OTHER INFORMATION: mouse tmst2

<400> SEQUENCE: 7
ttgcactcgg cc atg ttt ggc ttc ttc tgc agc ttg gtg tcc agt ctg agt      51
              Met Phe Gly Phe Phe Cys Ser Leu Val Ser Ser Leu Ser
                1               5                  10 cgc tgg ttc ctt tgg cgg cgg ctg ctg ctg ctg ctg ctg ctg ctg            99
Arg Trp Phe Leu Trp Arg Arg Leu Leu Leu Leu Leu Leu Leu Leu
 15                  20                  25 ctg aat ctg ccc ttg cag gta aaa ttt gct atg cta gaa tta cac tcc       147
Leu Asn Leu Pro Leu Gln Val Lys Phe Ala Met Leu Glu Leu His Ser
 30                  35                  40                  45 ttc aaa tgt ccc gct ggt gaa tac tgg tct aaa gac gtc tgt tgc aag       195
Phe Lys Cys Pro Ala Gly Glu Tyr Trp Ser Lys Asp Val Cys Cys Lys
                 50                  55                  60 aac tgt tct gca ggt aca ttt gtc aag gcg ccc tgc gaa atc ccc cat       243
Asn Cys Ser Ala Gly Thr Phe Val Lys Ala Pro Cys Glu Ile Pro His
             65                  70                  75 act caa gga caa tgt gag aag tgt cac cca gga aca ttc aca gag aaa       291
Thr Gln Gly Gln Cys Glu Lys Cys His Pro Gly Thr Phe Thr Glu Lys
         80                  85                  90 gat aat tac ctg gat gct tgt ata ctt tgc tcc acc tgt gat aaa gat       339
Asp Asn Tyr Leu Asp Ala Cys Ile Leu Cys Ser Thr Cys Asp Lys Asp
         95                 100                 105 cag gaa atg gtg gcc gac tgc tca gcc acc agt gac cgg aaa tgc cag       387
Gln Glu Met Val Ala Asp Cys Ser Ala Thr Ser Asp Arg Lys Cys Gln
110                 115                 120                 125 tgc cga aca ggt ctt tac tac tat gac cca aaa ttt cca gaa tcg tgc       435
Cys Arg Thr Gly Leu Tyr Tyr Tyr Asp Pro Lys Phe Pro Glu Ser Cys
                130                 135                 140 cgc cca tgt acc aag tgt ccc caa gga atc cct gtc ctc cag gaa tgc       483
Arg Pro Cys Thr Lys Cys Pro Gln Gly Ile Pro Val Leu Gln Glu Cys
            145                 150                 155 aac tcc aca gct aac act gtg tgc agt tca tct gtt tca aat ccc aga       531
Asn Ser Thr Ala Asn Thr Val Cys Ser Ser Ser Val Ser Asn Pro Arg
        160                 165                 170 aac cgg ctg ttc cta ctg tta tca cct ttg agt gtg cta att gtg tcc       579
Asn Arg Leu Phe Leu Leu Leu Ser Pro Leu Ser Val Leu Ile Val Ser
    175                 180                 185 gtt gtt gtc ttc cgt atc ata aga aga taaggttct acagatgttt              626
Val Val Val Phe Arg Ile Ile Arg Arg
190                 195 tcttagcttc cttttattgc tatgaagtga tactatggag gcaactcttt tattttattt     686
attttatttt attttttaat gtcttgaact tgatttgaag accaggctgg cctcaaaatc     746
acagagatcc agactaagac aactctaata agggaaacat ttaattggga ctggcttaca     806
gtttcggacg ttttgtccat gattatcata gtgggaagca tggcagcatc taagcagaca     866
tgatgttgga gaaggagctg agatttctgc atcttgatct gcaagcaata aaaggagact     926
```

| | |
|---|---|
| gtgtgccaca ctatacacag cttgaacata ggagacctca aagcctgtcc ccacagtgac | 986 |
| aaacttcctc caacaaggtc atacctccta ataataccat ttcttatgag gcaagcattc | 1046 |
| aaacacatga gtctatgagg gccaaaccaa ttcaaaccac acaggttaa caattgccct | 1106 |
| ctgcagctct ctggtggagg ccctccttga gagtaagtaa caatttagat gaaggcaagt | 1166 |
| cctggtatca ggtccaaaag aaactcagga tgaatggtcc actgtggttc ctattaacat | 1226 |
| actgaagaac atgacctcac cttacacgtc tccacctcac tgacttccct tcccctagct | 1286 |
| tctcattccc aggtaaccct gccatttttt ggtaatgtgc cttcttggtt cttcctctcc | 1346 |
| tttccccctc tcttctggtc cttacttctc ttcctctccc actctccacc agcctcctct | 1406 |
| taaggcctga atcagtctgt aggtcatgtt taatctacta ctttctctct gctctggact | 1466 |
| catccagatg tctctggctg agctctccct cctatctaca ataaaaccct tcccctaac | 1526 |
| cagaaatgca aaaaaaaaaa aaaa | 1550 |

```
<210> SEQ ID NO 8
<211> LENGTH: 198
<212> TYPE: PRT
<213> ORGANISM: Mus musculus

<400> SEQUENCE: 8

Met Phe Gly Phe Phe Cys Ser Leu Val Ser Ser Leu Ser Arg Trp Phe
  1               5                  10                  15

Leu Trp Arg Arg Leu Leu Leu Leu Leu Leu Leu Leu Leu Leu Asn Leu
             20                  25                  30

Pro Leu Gln Val Lys Phe Ala Met Leu Glu Leu His Ser Phe Lys Cys
         35                  40                  45

Pro Ala Gly Glu Tyr Trp Ser Lys Asp Val Cys Cys Lys Asn Cys Ser
     50                  55                  60

Ala Gly Thr Phe Val Lys Ala Pro Cys Glu Ile Pro His Thr Gln Gly
 65                  70                  75                  80

Gln Cys Glu Lys Cys His Pro Gly Thr Phe Thr Glu Lys Asp Asn Tyr
                 85                  90                  95

Leu Asp Ala Cys Ile Leu Cys Ser Thr Cys Asp Lys Asp Gln Glu Met
            100                 105                 110

Val Ala Asp Cys Ser Ala Thr Ser Asp Arg Lys Cys Gln Cys Arg Thr
        115                 120                 125

Gly Leu Tyr Tyr Tyr Asp Pro Lys Phe Pro Glu Ser Cys Arg Pro Cys
    130                 135                 140

Thr Lys Cys Pro Gln Gly Ile Pro Val Leu Gln Glu Cys Asn Ser Thr
145                 150                 155                 160

Ala Asn Thr Val Cys Ser Ser Val Ser Asn Pro Arg Asn Arg Leu
                165                 170                 175

Phe Leu Leu Leu Ser Pro Leu Ser Val Leu Ile Val Ser Val Val Val
            180                 185                 190

Phe Arg Ile Ile Arg Arg
        195

<210> SEQ ID NO 9
<211> LENGTH: 702
<212> TYPE: DNA
<213> ORGANISM: Mus musculus
<220> FEATURE:
<221> NAME/KEY: CDS
<222> LOCATION: (13)..(552)
<223> OTHER INFORMATION: Primer 2086-39
```

-continued

<400> SEQUENCE: 9

```
ttgcactcgg cc atg ttt ggc ttc ttc tgc agc ttg gtg tcc agt ctg agt         51
              Met Phe Gly Phe Phe Cys Ser Leu Val Ser Ser Leu Ser
                1               5                  10 cgc tgg ttc ctt tgg cgg cgg ctg ctg ctg ctg ctg ctg ctg ctg                99
Arg Trp Phe Leu Trp Arg Arg Leu Leu Leu Leu Leu Leu Leu Leu
 15                  20                  25 ctg aat ctg ccc ttg cag gta aaa ttt gct atg cta gaa tta cac tcc           147
Leu Asn Leu Pro Leu Gln Val Lys Phe Ala Met Leu Glu Leu His Ser
 30                  35                  40                  45 ttc aaa tgt ccc gct ggt gaa tac tgg tct aaa gac gtc tgt tgc aag           195
Phe Lys Cys Pro Ala Gly Glu Tyr Trp Ser Lys Asp Val Cys Cys Lys
                 50                  55                  60 aac tgt tct gca ggt aca ttt gtc aag gcg ccc tgc gaa atc ccc cat           243
Asn Cys Ser Ala Gly Thr Phe Val Lys Ala Pro Cys Glu Ile Pro His
             65                  70                  75 act caa gga caa tgt gag aag tgt cac cca gga aca ttc aca gag aaa           291
Thr Gln Gly Gln Cys Glu Lys Cys His Pro Gly Thr Phe Thr Glu Lys
         80                  85                  90 gat aat tac ctg gat gct tgt ata ctt tgc tcc acc tgt gat aaa gat           339
Asp Asn Tyr Leu Asp Ala Cys Ile Leu Cys Ser Thr Cys Asp Lys Asp
 95                 100                 105 cag gaa atg gtg gcc gac tgc tca gcc acc agt gac cgg aaa tgc cag           387
Gln Glu Met Val Ala Asp Cys Ser Ala Thr Ser Asp Arg Lys Cys Gln
110                 115                 120                 125 tgc cga aca ggt ctt tac tac tat gac cca aaa ttt cca gaa tcg tgc           435
Cys Arg Thr Gly Leu Tyr Tyr Tyr Asp Pro Lys Phe Pro Glu Ser Cys
                130                 135                 140 cgc cca tgt acc aag tgt ccc caa gga atc cct gtc ctc cag gaa tgc           483
Arg Pro Cys Thr Lys Cys Pro Gln Gly Ile Pro Val Leu Gln Glu Cys
             145                 150                 155 aac tcc aca gct aac act gtg tgc agt tca tct gtt tca aga aga tct           531
Asn Ser Thr Ala Asn Thr Val Cys Ser Ser Ser Val Ser Arg Arg Ser
         160                 165                 170 gcc tca gtg gcc tgg cct atc tgaatggttc acagagatcc cagaaaccgg             582
Ala Ser Val Ala Trp Pro Ile
     175                 180 ctgttcctac tgttatcacc tttgagtgtg ctaattgtgt ccgttgttgt cttccgtatc         642
ataagaagat aaaggttcta cagatgtttt cttagcttcc ttttattgct atgaagtgat         702

<210> SEQ ID NO 10
<211> LENGTH: 180
<212> TYPE: PRT
<213> ORGANISM: Mus musculus

<400> SEQUENCE: 10

Met Phe Gly Phe Phe Cys Ser Leu Val Ser Ser Leu Ser Arg Trp Phe
  1               5                  10                  15

Leu Trp Arg Arg Leu Leu Leu Leu Leu Leu Leu Leu Asn Leu
             20                  25                  30

Pro Leu Gln Val Lys Phe Ala Met Leu Glu Leu His Ser Phe Lys Cys
         35                  40                  45

Pro Ala Gly Glu Tyr Trp Ser Lys Asp Val Cys Cys Lys Asn Cys Ser
     50                  55                  60

Ala Gly Thr Phe Val Lys Ala Pro Cys Glu Ile Pro His Thr Gln Gly
 65                  70                  75                  80

Gln Cys Glu Lys Cys His Pro Gly Thr Phe Thr Glu Lys Asp Asn Tyr
                 85                  90                  95
```

-continued

```
Leu Asp Ala Cys Ile Leu Cys Ser Thr Cys Asp Lys Asp Gln Glu Met
            100                 105                 110

Val Ala Asp Cys Ser Ala Thr Ser Asp Arg Lys Cys Gln Cys Arg Thr
        115                 120                 125

Gly Leu Tyr Tyr Tyr Asp Pro Lys Phe Pro Glu Ser Cys Arg Pro Cys
    130                 135                 140

Thr Lys Cys Pro Gln Gly Ile Pro Val Leu Gln Glu Cys Asn Ser Thr
145                 150                 155                 160

Ala Asn Thr Val Cys Ser Ser Ser Val Ser Arg Arg Ser Ala Ser Val
                165                 170                 175

Ala Trp Pro Ile
            180
```

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: primer
<223> OTHER INFORMATION: Primer 2038-41

<400> SEQUENCE: 11
catactagtt ccaccatgtt tggcttcttc tgcagcttgg t                          41

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: primer
<223> OTHER INFORMATION: tmst2-Ig fusion protein

<400> SEQUENCE: 12
ttgtcgacat ttgaaacaga tgaactgcac aca                                   33

<210> SEQ ID NO 13
<211> LENGTH: 1200
<212> TYPE: DNA
<213> ORGANISM: Artificial Sequence
<220> FEATURE:
<223> OTHER INFORMATION: Description of Artificial Sequence: Fusion
      protein consisting of Mus musculus sequences and Immunoglobulin
      sequences
<221> NAME/KEY: CDS
<222> LOCATION: (1)..(1194)

<400> SEQUENCE: 13

```
atg ttt ggc ttc ttc tgc agc ttg gtg tcc agt ctg agt cgc tgg ttc        48
Met Phe Gly Phe Phe Cys Ser Leu Val Ser Ser Leu Ser Arg Trp Phe
  1               5                  10                  15 ctt tgg cgg cgg ctg ctg ctg ctg ctg ctg ctg ctg ctg aat ctg             96
Leu Trp Arg Arg Leu Leu Leu Leu Leu Leu Leu Leu Leu Asn Leu
                20                  25                  30 ccc ttg cag gta aaa ttt gct atg cta gaa tta cac tcc ttc aaa tgt        144
Pro Leu Gln Val Lys Phe Ala Met Leu Glu Leu His Ser Phe Lys Cys
            35                  40                  45 ccc gct ggt gaa tac tgg tct aaa gac gtc tgt gca aag aac tgt tct        192
Pro Ala Gly Glu Tyr Trp Ser Lys Asp Val Cys Cys Lys Asn Cys Ser
        50                  55                  60 gca ggt aca ttt gtc aag gcg ccc tgc gaa atc ccc cat act caa gga        240
Ala Gly Thr Phe Val Lys Ala Pro Cys Glu Ile Pro His Thr Gln Gly
 65                  70                  75                  80
```

-continued

| | |
|---|---|
| caa tgt gag aag tgt cac cca gga aca ttc aca gag aaa gat aat tac<br>Gln Cys Glu Lys Cys His Pro Gly Thr Phe Thr Glu Lys Asp Asn Tyr<br>                     85                    90                    95 | 288 |
| ctg gat gct tgt ata ctt tgc tcc acc tgt gat aaa gat cag gaa atg<br>Leu Asp Ala Cys Ile Leu Cys Ser Thr Cys Asp Lys Asp Gln Glu Met<br>                 100                   105                 110 | 336 |
| gtg gcc gac tgc tca gcc acc agt gac cgg aaa tgc cag tgc cga aca<br>Val Ala Asp Cys Ser Ala Thr Ser Asp Arg Lys Cys Gln Cys Arg Thr<br>           115                    120                   125 | 384 |
| ggt ctt tac tac tat gac cca aaa ttt cca gaa tcg tgc cgc cca tgt<br>Gly Leu Tyr Tyr Tyr Asp Pro Lys Phe Pro Glu Ser Cys Arg Pro Cys<br>130                    135                   140 | 432 |
| acc aag tgt ccc caa gga atc cct gtc ctc cag gaa tgc aac tcc aca<br>Thr Lys Cys Pro Gln Gly Ile Pro Val Leu Gln Glu Cys Asn Ser Thr<br>145                    150                   155                 160 | 480 |
| gct aac act gtg tgc agt tca tct gtt tca aat gtc gac act cac aca<br>Ala Asn Thr Val Cys Ser Ser Ser Val Ser Asn Val Asp Thr His Thr<br>                 165                   170                 175 | 528 |
| tgc cca ccg tgc cca gca cct gaa ctc ctg ggg gga ccg tca gtc ttc<br>Cys Pro Pro Cys Pro Ala Pro Glu Leu Leu Gly Gly Pro Ser Val Phe<br>           180                    185                   190 | 576 |
| ctc ttc ccc cca aaa ccc aag gac acc ctc atg atc tcc cgg acc cct<br>Leu Phe Pro Pro Lys Pro Lys Asp Thr Leu Met Ile Ser Arg Thr Pro<br>           195                    200                   205 | 624 |
| gag gtc aca tgc gtg gtg gtg gac gtg agc cac gaa gac cct gag gtc<br>Glu Val Thr Cys Val Val Val Asp Val Ser His Glu Asp Pro Glu Val<br>210                    215                   220 | 672 |
| aag ttc aac tgg tac gtg gac ggc gtg gag gtg cat aat gcc aag aca<br>Lys Phe Asn Trp Tyr Val Asp Gly Val Glu Val His Asn Ala Lys Thr<br>225                    230                   235                 240 | 720 |
| aag ccg cgg gag gag cag tac aac agc acg tac cgt gtg gtc agc gtc<br>Lys Pro Arg Glu Glu Gln Tyr Asn Ser Thr Tyr Arg Val Val Ser Val<br>                 245                   250                 255 | 768 |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys<br>           260                    265                   270 | 816 |
| aag gtc tcc aac aaa gcc ctc cca gcc ccc atc gag aaa acc atc tcc<br>Lys Val Ser Asn Lys Ala Leu Pro Ala Pro Ile Glu Lys Thr Ile Ser<br>           275                    280                   285 | 864 |
| aaa gcc aaa ggg cag ccc cga gaa cca cag gtg tac acc ctg ccc cca<br>Lys Ala Lys Gly Gln Pro Arg Glu Pro Gln Val Tyr Thr Leu Pro Pro<br>290                    295                   300 | 912 |
| tcc cgg gat gag ctg acc aag aac cag gtc agc ctg acc tgc ctg gtc<br>Ser Arg Asp Glu Leu Thr Lys Asn Gln Val Ser Leu Thr Cys Leu Val<br>305                    310                   315                 320 | 960 |
| aaa ggc ttc tat ccc agc gac atc gcc gtg gag tgg gag agc aat ggg<br>Lys Gly Phe Tyr Pro Ser Asp Ile Ala Val Glu Trp Glu Ser Asn Gly<br>                 325                   330                 335 | 1008 |
| cag ccg gag aac aac tac aag acc acg cct ccc gtg ctg gac tcc gac<br>Gln Pro Glu Asn Asn Tyr Lys Thr Thr Pro Pro Val Leu Asp Ser Asp<br>           340                    345                   350 | 1056 |
| ggc tcc ttc ttc ctc tac agc aag ctc acc gtg gac aag agc agg tgg<br>Gly Ser Phe Phe Leu Tyr Ser Lys Leu Thr Val Asp Lys Ser Arg Trp<br>                 355                   360                 365 | 1104 |
| cag cag ggg aac gtc ttc tca tgc tcc gtg atg cat gag gct ctg cac<br>Gln Gln Gly Asn Val Phe Ser Cys Ser Val Met His Glu Ala Leu His<br>370                    375                   380 | 1152 |
| aac cac tac acg cag aag agc ctc tcc ctg tct ccg ggt aaa tgataa<br>Asn His Tyr Thr Gln Lys Ser Leu Ser Leu Ser Pro Gly Lys<br>385                    390                   395 | 1200 |

```
<210> SEQ ID NO 14
<211> LENGTH: 398
<212> TYPE: PRT
<213> ORGANISM: Artificial Sequence
<220> FEATURE:
<223> OTHER INFORMATION: Description of Artificial Sequence: Fusion
      protein consisting of Mus musculus sequences and Immunoglobulin
      sequences

<400> SEQUENCE: 14

Met Phe Gly Phe Phe Cys Ser Leu Val Ser Leu Ser Arg Trp Phe
  1               5                  10                  15

Leu Trp Arg Arg Leu Leu Leu Leu Leu Leu Leu Leu Leu Asn Leu
                 20                  25                  30

Pro Leu Gln Val Lys Phe Ala Met Leu Glu Leu His Ser Phe Lys Cys
                 35                  40                  45

Pro Ala Gly Glu Tyr Trp Ser Lys Asp Val Cys Cys Lys Asn Cys Ser
 50                  55                  60

Ala Gly Thr Phe Val Lys Ala Pro Cys Glu Ile Pro His Thr Gln Gly
 65                  70                  75                  80

Gln Cys Glu Lys Cys His Pro Gly Thr Phe Thr Glu Lys Asp Asn Tyr
                 85                  90                  95

Leu Asp Ala Cys Ile Leu Cys Ser Thr Cys Asp Lys Asp Gln Glu Met
                100                 105                 110

Val Ala Asp Cys Ser Ala Thr Ser Asp Arg Lys Cys Gln Cys Arg Thr
                115                 120                 125

Gly Leu Tyr Tyr Tyr Asp Pro Lys Phe Pro Glu Ser Cys Arg Pro Cys
130                 135                 140

Thr Lys Cys Pro Gln Gly Ile Pro Val Leu Gln Glu Cys Asn Ser Thr
145                 150                 155                 160

Ala Asn Thr Val Cys Ser Ser Val Ser Asn Val Asp Thr His His Thr
                165                 170                 175

Cys Pro Pro Cys Pro Ala Pro Glu Leu Leu Gly Gly Pro Ser Val Phe
                180                 185                 190

Leu Phe Pro Pro Lys Pro Lys Asp Thr Leu Met Ile Ser Arg Thr Pro
                195                 200                 205

Glu Val Thr Cys Val Val Val Asp Val Ser His Glu Asp Pro Glu Val
210                 215                 220

Lys Phe Asn Trp Tyr Val Asp Gly Val Glu Val His Asn Ala Lys Thr
225                 230                 235                 240

Lys Pro Arg Glu Glu Gln Tyr Asn Ser Thr Tyr Arg Val Val Ser Val
                245                 250                 255

Leu Thr Val Leu His Gln Asp Trp Leu Asn Gly Lys Glu Tyr Lys Cys
                260                 265                 270

Lys Val Ser Asn Lys Ala Leu Pro Ala Pro Ile Glu Lys Thr Ile Ser
                275                 280                 285

Lys Ala Lys Gly Gln Pro Arg Glu Pro Gln Val Tyr Thr Leu Pro Pro
                290                 295                 300

Ser Arg Asp Glu Leu Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
                340                 345                 350
```

-continued

```
Gly Ser Phe Phe Leu Tyr Ser Lys Leu Thr Val Asp Lys Ser Arg Trp
            355                 360                 365

Gln Gln Gly Asn Val Phe Ser Cys Ser Val Met His Glu Ala Leu His
        370                 375                 380

Asn His Tyr Thr Gln Lys Ser Leu Ser Leu Ser Pro Gly Lys
385                 390                 395

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: peptide

<400> SEQUENCE: 15

Tyr Gly Arg Lys Lys Arg Arg Gln Arg Arg Arg
  1               5                  10
```